(12) United States Patent
Monroe et al.

(10) Patent No.: US 8,859,503 B2
(45) Date of Patent: Oct. 14, 2014

(54) METHODS AND COMPOSITIONS TARGETING VIRAL AND CELLULAR ITAM MOTIFS, AND USE OF SAME IN IDENTIFYING COMPOUNDS WITH THERAPEUTIC ACTIVITY

(75) Inventors: John G Monroe, Philadelphia, PA (US); Elad Katz, Manchester (GB); Ramachandran Murali, Swarthmore, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 396 days.

(21) Appl. No.: 12/332,183

(22) Filed: Dec. 10, 2008

(65) Prior Publication Data

US 2009/0258032 A1 Oct. 15, 2009

Related U.S. Application Data

(63) Continuation of application No. 11/332,472, filed on Jan. 17, 2006, now abandoned.

(60) Provisional application No. 60/643,906, filed on Jan. 14, 2005, provisional application No. 60/649,900, filed on Feb. 4, 2005.

(51) Int. Cl.
*A61K 38/00* (2006.01)
*A61K 38/17* (2006.01)

(52) U.S. Cl.
CPC .................................. *A61K 38/1709* (2013.01)
USPC ....................................................... 514/19.3

(58) Field of Classification Search
None
See application file for complete search history.

(56) References Cited

U.S. PATENT DOCUMENTS

| | | | | |
|---|---|---|---|---|
| 6,670,466 | B1* | 12/2003 | Garry | 536/23.72 |
| 7,166,707 | B2* | 1/2007 | Feige | 530/350 |
| 2003/0113828 | A1* | 6/2003 | Ginsberg et al. | 435/15 |
| 2007/0003522 | A1* | 1/2007 | Albritton | 424/93.2 |

OTHER PUBLICATIONS

Lederman, De Martino, Daugherty, Foeldvari, Yellin, Cleary, Berkowitz, Lowy, Braunstein, Mark, and Chess. A single amino acid substitution in a common African allele of the CD4 molecule ablates binding of the monoclonal antibody, OKT4. Molecular Immunology, 1991. vol. 28, pp. 1171-1181.*
Li Yamashiro, Tseng, Chang, and Ferrara. Beta-endorphin omission analogs: dissociation of immunoreactivity from other biological activities. Proceedings of the National Academy of Sciences, 1980. vol. 77, pp. 3211-3214.*
Sela and Zisman. Different roles of D-amino acids in immune phenomena. FASEB Journal, 1997. vol. 11, pp. 449-456.*
Burzyn D et al, Toll-like receptor 4-dependent activation of dendritic cells by a retrovirus. J Virol. Jan. 2004;78(2):576-84.
Dzuris JL et al, Expression of mouse mammary tumor virus envelope protein does not prevent superinfection in vivo or in vitro. Virology. Oct. 25, 1999;263(2):418-26.
Pui JC et al, Notch1 expression in early lymphopoiesis influences B versus T lineage determination. Immunity Sep. 1999;11(3):299-308.
Burgess et al., "Possible dissociation of the heparin-binding mitogenic activities of heparin binding (acidic fibroblast) growth factor-1 from its receptor-binding activities by site-directed mutagenesis of a single lysine residue", Journal of Cell Biology, 1990, vol. 111, pp. 2129-2138.
Lazar et al., "Transforming growth factor a: mutation of aspartic acid 47 and leucine 48 results in different biological activities", Molecular and Cellular Biology, 1988, vol. 8, pp. 1247-1252.
Gura et al., "Systems for identifying new drugs are often faulty", Science 1997, vol. 278, pp. 1041-1042.
MSNBC News Services, "Mixed results on new cancer drug", Nov. 9, 2000.

* cited by examiner

*Primary Examiner* — Sheela J Huff
(74) *Attorney, Agent, or Firm* — Mark S. Cohen; Pearl Cohen Zedek Latzer Baratz LLP

(57) ABSTRACT

This invention provides methods of treating, reducing the incidence of, and inhibiting metastasis formation of carcinomas, sarcomas, Epstein-Barr virus-induced malignancies, B cell proliferative disorders, and mast cell activation disorders, comprising administering to a subject a compound that inhibits an interaction of a first protein and an immunoreceptor tyrosine-based activation motif (ITAM) of a second protein, and screening methods for identifying ITAM-inhibitory compounds and peptides. This invention also provides peptides that inhibit signaling by ITAMs.

11 Claims, 21 Drawing Sheets

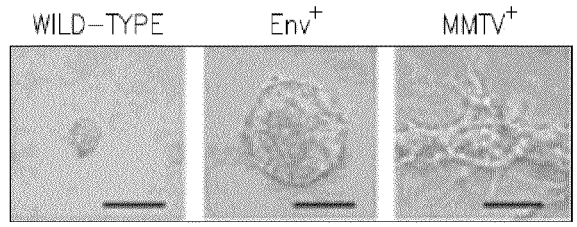
Figure 3A
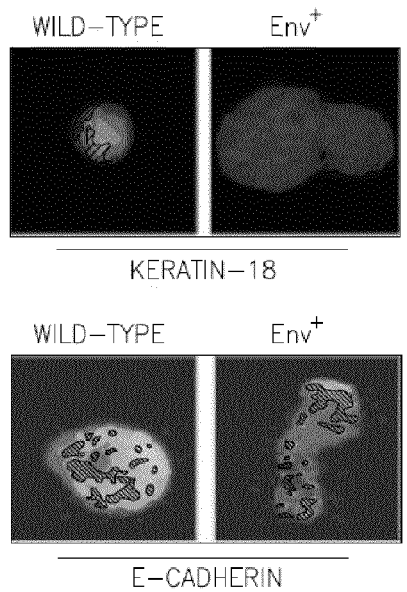
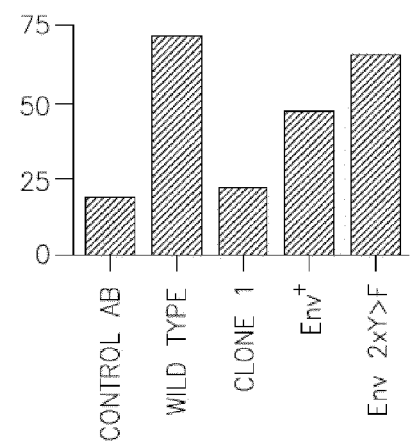
Figure 3B
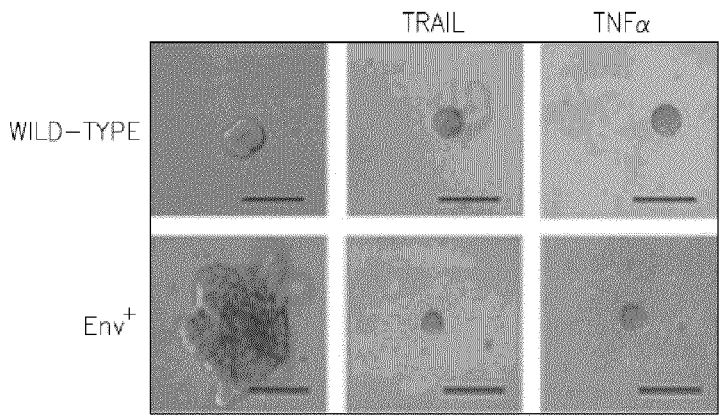
Figure 3C
Figure 3

Figure 12A-B

METHODS AND COMPOSITIONS TARGETING VIRAL AND CELLULAR ITAM MOTIFS, AND USE OF SAME IN IDENTIFYING COMPOUNDS WITH THERAPEUTIC ACTIVITY

CROSS REFERENCE TO RELATED APPLICATIONS

This application is a Continuation of U.S. patent application Ser. No. 11/332,472, filed Jan. 17, 2006 now abandoned, which claims priority of U.S. Provisional Application Ser. Nos. 60/643,906, filed Jan. 14, 2005, and 60/649,900, filed Feb. 4, 2005, all which are incorporated herein by reference in their entirety.

STATEMENT REGARDING FEDERALLY SPONSORED RESEARCH OR DEVELOPMENT

The invention described herein was supported in whole or in part by grants from The National Institutes of Health (Grant Numbers P01-CA093615, R01-AI43620, R01-CA087609, R01-CA073746, RO1-AI32592, and CA09140) and the Department of Defense (Grant Numbers DMAD17-00-1-0249 and W81XWH-04-1-0435). The government has certain rights in the invention.

FIELD OF INVENTION

This invention provides methods of treating, reducing the incidence of, and inhibiting metastasis formation of carcinomas, sarcomas, Epstein-Barr virus-induced malignancies, B cell proliferative disorders, and mast cell activation disorders, comprising administering to a subject a compound that inhibits an interaction of a first protein and an immunoreceptor tyrosine-based activation motif (ITAM) of a second protein, and screening methods for identifying ITAM-inhibitory compounds and peptides. This invention also provides peptides that inhibit signaling by ITAMs.

BACKGROUND OF THE INVENTION

Oncogenic viruses such as Epstein-Barr virus (EBV) and Kaposi sarcoma-associated herpesvirus (KSHV) are associated with a number of malignancies, such as Kaposi sarcoma, Burkitt's lymphoma, Hodgkin's lymphoma, post-transplant lymphoproliferative disease, and the epithelial cell malignancy nasopharyngeal carcinoma (NPC). Methods for treating these and similar malignancies are urgently needed.

In addition, a variety of immune cell activation diseases and disorders (e.g. B cell proliferative diseases and disorders and mast cell activation diseases and disorders) cause significant morbidity and mortality in the human population. Methods for treating such diseases and disorders are also urgently needed.

SUMMARY OF THE INVENTION

This invention provides methods of treating, reducing the incidence of, and inhibiting metastasis formation of carcinomas, sarcomas, Epstein-Barr virus-induced malignancies, B cell proliferative disorders, and mast cell activation disorders, comprising administering to a subject a compound that inhibits an interaction of a first protein and an immunoreceptor tyrosine-based activation motif (ITAM) of a second protein, and screening methods for identifying ITAM-inhibitory compounds and peptides. This invention also provides peptides that inhibit signaling by ITAMs.

In one embodiment, the present invention provides a method of treating a carcinoma in a subject, comprising administering to the subject a compound that inhibits an interaction of a first protein and an ITAM of a second protein, thereby treating a carcinoma in a subject.

In another embodiment, the present invention provides a method of reducing an incidence of a carcinoma in a subject, comprising administering to the subject a compound that inhibits an interaction of a first protein and an ITAM of a second protein, thereby reducing an incidence of a carcinoma in a subject.

In another embodiment, the present invention provides a method of inhibiting a formation of a metastasis of a carcinoma in a subject, comprising administering to the subject a compound that inhibits an interaction of a first protein and an ITAM of a second protein, thereby inhibiting a formation of a metastasis of a carcinoma in a subject.

In another embodiment, the present invention provides a method of treating a sarcoma in a subject, comprising administering to the subject a compound that inhibits an interaction of a first protein and an ITAM of a second protein, thereby treating a sarcoma in a subject.

In another embodiment, the present invention provides a method of reducing an incidence of a sarcoma in a subject, comprising administering to the subject a compound that inhibits an interaction of a first protein and an ITAM of a second protein, thereby reducing an incidence of a sarcoma in a subject.

In another embodiment, the present invention provides a method of inhibiting a formation of a metastasis of a sarcoma in a subject, comprising administering to the subject a compound that inhibits an interaction of a first protein and an ITAM of a second protein, thereby inhibiting a formation of a metastasis of a sarcoma in a subject.

In another embodiment, the present invention provides a method of treating an Epstein-Barr virus-induced malignancy in a subject, comprising administering to the subject a compound that inhibits an interaction of a first protein and an ITAM of a second protein, thereby treating an Epstein-Barr virus-induced malignancy in a subject.

In another embodiment, the present invention provides a method of reducing an incidence of an Epstein-Barr virus-induced malignancy in a subject, comprising administering to the subject a compound that inhibits an interaction of a first protein and an ITAM of a second protein, thereby reducing an incidence of an Epstein-Barr virus-induced malignancy in a subject.

In another embodiment, the present invention provides a method of inhibiting a formation of a metastasis of an Epstein-Barr virus-induced malignancy in a subject, comprising administering to the subject a compound that inhibits an interaction of a first protein and an ITAM of a second protein, thereby inhibiting a formation of a metastasis of an Epstein-Barr virus-induced malignancy in a subject.

In another embodiment, the present invention provides a method of treating a B cell proliferative disorder in a subject, comprising administering to the subject a compound that inhibits an interaction of a first protein and an ITAM of a second protein, thereby treating a B cell proliferative disorder in a subject.

In another embodiment, the present invention provides a method of reducing an incidence of a B cell proliferative disorder in a subject, comprising administering to the subject a compound that inhibits an interaction of a first protein and an ITAM of a second protein, thereby reducing an incidence of a pathological immune cell activation in a subject.

In another embodiment, the present invention provides a method of treating a mast cell activation disorder in a subject, comprising administering to the subject a compound that inhibits an interaction of a first protein and an ITAM of a second protein, thereby treating a mast cell activation disorder in a subject.

In another embodiment, the present invention provides a method of reducing an incidence of a mast cell activation disorder in a subject, comprising administering to the subject a compound that inhibits an interaction of a first protein and an ITAM of a second protein, thereby reducing an incidence of a mast cell activation disorder in a subject.

BRIEF DESCRIPTION OF THE FIGURES

FIG. 3. Expression of MMTV Env in murine mammary epithelial cells is sufficient for cell transformation. (A) Representative images of three-dimensional cultures, on Matrigel® cushions, of un-transfected ("wild-type") and unmutated envelope-transfected ("$Env^+$") NMuMG cells at day 6 of culture are depicted. Bars, 50 Mm. (B) Left panel: Keratin-18 staining of un-transfected and unmutated envelope-transfected NMuMG cells at day 6. Keratin-18 is in the bright area shaded in diagonal lines; nuclear staining (DAPI) is in the unmarked, bright area. Right panel: E-cadherin surface expression, as quantified by flow cytometry, is reduced in two-dimensional cultures of unmutated envelope-transfected and MMTV+ ("clone 1") NMuMG cells. (C) Un-transfected ("wild-type") and unmutated envelope-transfected ("$Env^+$") cultures were treated 17 h before imaging with either normal assay media, 1 µg/ml TRAIL, or 100 nM TNF. Induction of apoptosis was confirmed by TUNEL assays.

DETAILED DESCRIPTION OF THE INVENTION

Figure 1:
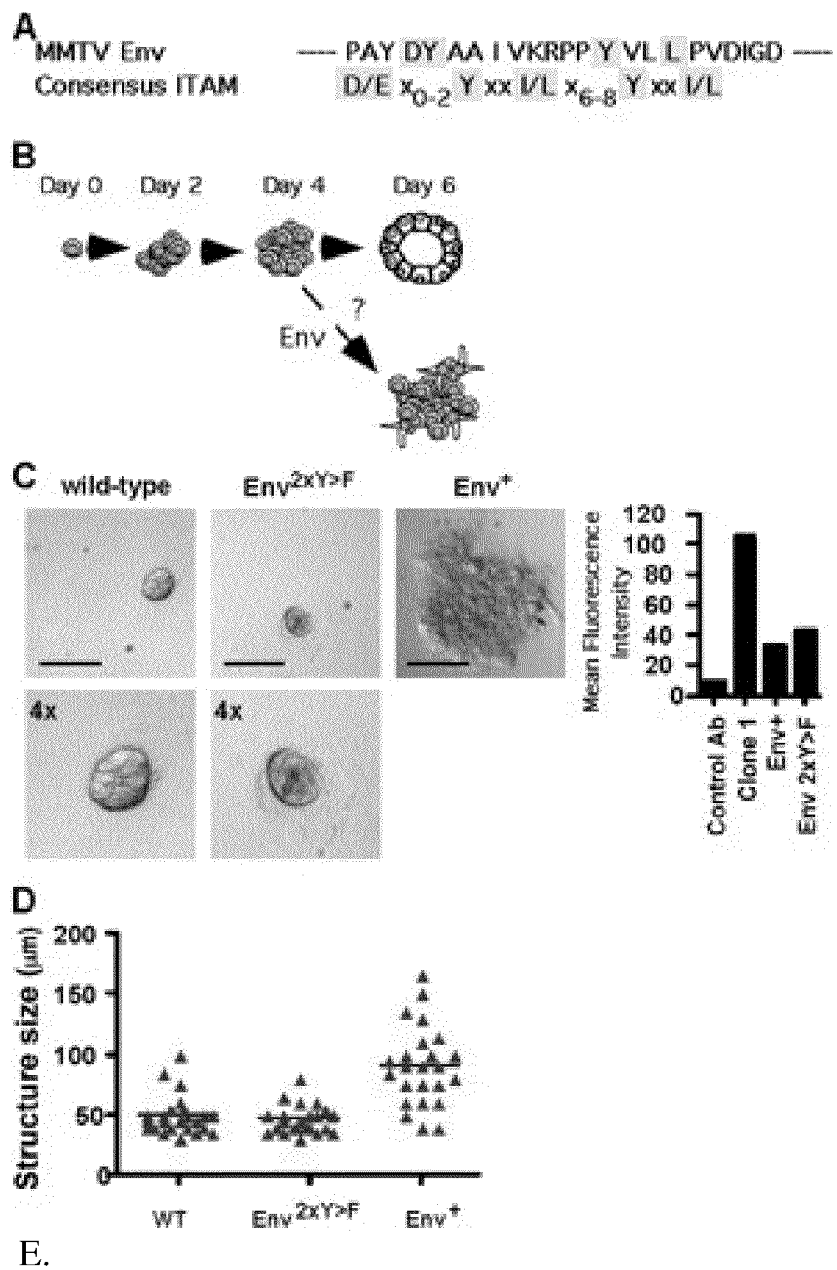
FIG. 1: Contribution of ITAM domain in MMTV Env to cell transformation. (A) Schematic comparison of the ITAM in MMTV Env (SEQ ID NO: 99) and consensus ITAM sequence (SEQ ID NO: 10). Conserved residues are shaded. (B) Development of mammary epithelial cell acinar structures on Matrigel. (C) Left panel: Representative images of three-dimensional cultures of un-transfected ("wild-type"), mutated envelope-transfected ("$Env^{2xY>F}$"), and unmutated envelope-transfected ("$Env^+$") NMuMG cells at day 6 of culture. For WT and $Env^{2xY>F}$, images are also depicted at a magnification of 4. Note polarized structures with hollow lumen in both cell types. Bars, 50 µm. Right panel: Mean fluorescence intensity of Env expression in the transfected cells. "Clone 1" refers to the MMTV+NMuMG cells. (D) Quantification of structure size in a representative experiment. (E) Representative images of three-dimensional cultures of un-transfected ("wild-type"), unmutated envelope-transfected ("$Env^+$"), and MMTV infected NMuMG cells at day 6 of culture. Black bars represent the median for each culture. Surface expression of MMTV SU (gp52) is depicted for mutated envelope-transfected and un-mutated envelope-transfected NMuMG cells. Normal goat IgG was used as the control antibody.
Figure 1:
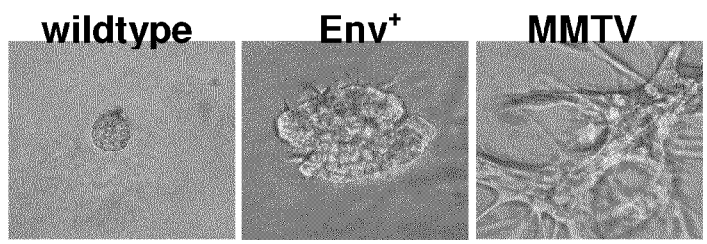

This invention provides methods of treating, reducing the incidence of, and inhibiting metastasis formation of carcinomas, sarcomas, Epstein-Barr virus-induced malignancies, B cell proliferative disorders, and mast cell activation disorders, comprising administering to a subject a compound that inhibits an interaction of a first protein and an immunoreceptor tyrosine-based activation motif (ITAM) of a second protein, and screening methods for identifying ITAM-inhibitory compounds and peptides. This invention also provides peptides that inhibit signaling by ITAMs.

In one embodiment, the present invention provides a method of treating a carcinoma in a subject, comprising administering to the subject a compound that inhibits an interaction of a first protein and an ITAM of a second protein, thereby treating a carcinoma in a subject. In one embodiment of methods and compositions of the present invention, the interaction between the first protein and the ITAM is an intracellular interaction.

In another embodiment, the present invention provides a method of reducing an incidence of a carcinoma in a subject, comprising administering to the subject a compound that inhibits an interaction of a first protein and an ITAM of a second protein, thereby reducing an incidence of a carcinoma in a subject.

In another embodiment, the present invention provides a method of inhibiting a formation of a metastasis of a carcinoma in a subject, comprising administering to the subject a compound that inhibits an interaction of a first protein and an ITAM of a second protein, thereby inhibiting a formation of a metastasis of a carcinoma in a subject.

In another embodiment, the present invention provides a method of reducing an invasiveness of a metastasis of a carcinoma in a subject, comprising administering to the subject a compound that inhibits an interaction of a first protein and an ITAM of a second protein, thereby reducing an invasiveness of a metastasis of a carcinoma in a subject.

In another embodiment, the present invention provides a method of reversing a malignant transformation of a carcinoma in a subject, comprising administering to the subject a compound that inhibits an interaction of a first protein and an ITAM of a second protein, thereby reversing a malignant transformation of a carcinoma in a subject.

As provided herein (Examples 1-4), findings of the present invention show that expression of a protein containing a viral ITAM, but not a mutant-ITAM-containing protein, is capable of transformation of epithelial cells, as shown by multiple assays. Activity of cellular signaling molecules that associated with the ITAM (e.g. Syk kinase) was necessary for the transformation to occur. These findings show that blocking association of a viral ITAM with cellular molecules and blocking viral ITAM-mediated signaling are effective strategies for preventing and reducing the incidence of malignant transformation. In addition, testing of a peptide of the present invention showed that ITAM association-blocking peptides can not only prevent, but also reverse transformation of epithelial cells, and thus can be used to treat existing carcinomas (Examples 5-6).

In addition, the findings of the present invention show that expression of a viral ITAM-containing protein increases invasiveness of epithelial cells, an indication of metastatic properties (Example 4). Thus, blocking association of an ITAM with cellular molecules blocking ITAM-mediated signaling are effective strategies for inhibiting metastases and reducing invasiveness of carcinoma cells.

Expression of a protein containing a cellular ITAM is also capable of transformation of epithelial cells (Examples 16-19). Thus, blocking association of a cellular ITAM with cellular molecules and blocking cellular ITAM-mediated signaling are effective strategies for preventing and reducing the incidence of carcinoma malignant transformation, treating carcinomas, inhibiting metastases, and reducing invasiveness of carcinoma cells.

Moreover, the present invention provides methods of modifying peptides of the present invention and identifying further improved peptides using models of carcinoma, both primary tumors and metastases (Examples 8-9); or, in another embodiment, using 3-dimensional culture assays of ITAM-containing protein-transfected cells (e.g. as described in Example 21); or, in another embodiment, using colony formation assays (e.g. as described in Example 22); or, in another embodiment, using ITAM co-IP assays (e.g. as described in Example 23); or, in another embodiment, using ability to abrogate or reduce EMT (e.g. as described in Example 24); or, in another embodiment, using ability to abrogate or reduce sensitivity to apoptosis (e.g. as described in Example 25); or, in another embodiment, using ability to abrogate or reduce phosphorylation of an ITAM-containing protein (e.g. as described in Example 29). These methods facilitate, in another embodiment, selection of further improved ITAM-inhibitory peptides.

"ITAMs" are, in one embodiment, motifs found in immune cells and some viral proteins, characterized by 2 YXXL/I (SEQ ID No: 11) sequences. The ITAM-containing protein (i.e. the "second protein") targeted by methods and compositions of the present invention is, in another embodiment, a viral protein. In another embodiment, the ITAM-containing protein is a cellular protein. In another embodiment, the ITAM or ITAM motif is a viral ITAM or ITAM motif. In another embodiment, the ITAM or ITAM motif is a cellular ITAM or ITAM motif.

In another embodiment, "ITAM" refers to a protein motif that functions as a docking site for SH2-containing signaling proteins involved in linking receptor-initiated signals to downstream cellular responses. In another embodiment, "ITAM" refers to a protein motif that interacts with proteins from Syk/Zap-70 family tyrosine kinases. In another embodiment, the ITAM motif interacts with Src family tyrosine kinases. In another embodiment, the ITAM motif interacts with both Syk/Zap-70 family tyrosine kinases and Src family tyrosine kinases. In another embodiment, one or more residues of the ITAM motif are phosphorylated by a Src family kinase. In another embodiment, the phosphorylation leads to Src-homology 2 (SH2)-mediated docking and activation of Syk family kinases. In another embodiment, adaptor molecules other than Syk kinases are recruited following phosphorylation of the ITAM motif. Each possibility represents a separate embodiment of the present invention.

"Viral ITAM" refers, in another embodiment, to an ITAM that is present on a viral protein. In another embodiment, the term refers to an ITAM that is expressed by a cell in response to a viral infection. "Cellular ITAM" refers, in another embodiment, to an ITAM that is present on a cellular protein. Each possibility represents a separate embodiment of the present invention.

In another embodiment, the ITAM has the sequence PAYD YAAIIVKRPPYVLLPVDIGD (SEQ ID No: 1). In another embodiment, the ITAM is homologous to SEQ ID No: 1. In another embodiment, the ITAM has the sequence (D/E)X$_7$(D/E)X$_2$YX$_2$LX$_7$YX$_2$(L/I), wherein X is any amino acid (SEQ ID No: 3). In another embodiment, the ITAM has the sequence (D/E)X$_8$(D/E)X$_2$YX$_2$LX$_{12}$YX$_2$(L/I) (SEQ ID No: 4). In another embodiment, the ITAM has the sequence (D/E)X$_{7-8}$(D/E)X$_2$YX$_2$LX$_7$YX$_2$(L/I) (SEQ ID No: 5). In another embodiment, the ITAM has the sequence (D/E)X$_{7-8}$(D/E)X$_2$YX$_2$LX$_{12}$YX$_2$(L/I) (SEQ ID No: 6). In another embodiment, the ITAM has the sequence (D/E)X$_7$(D/E)X$_2$YX$_2$LX$_{7-12}$YX$_2$(L/I) (SEQ ID No: 7). In another embodiment, the ITAM has the sequence (D/E)X$_8$(D/E)X$_2$YX$_2$LX$_{7-12}$YX$_2$(L/I) (SEQ ID No: 8). In another embodiment, the ITAM has the sequence YX$_2$(I/L)(X$_{6-8}$)YX$_2$(I/L) (SEQ ID No: 9). In another embodiment, the ITAM has the sequence (D/E)X$_{0-2}$YXX(L/I)X$_{6-8}$YXX(L/I) (SEQ ID No: 10). In another embodiment, the ITAM has the sequence (D/E)X$_{0-2}$YAAIX$_{6-8}$YVLL (SEQ ID No: 12). In another embodiment, the ITAM has the sequence (D/E)YAAIX$_{6-8}$YVLL (SEQ ID No: 13). In another embodiment, the ITAM has the sequence (D/E)X$_{0-2}$YAAIX$_6$YVLL (SEQ ID No: 14). In another embodiment, the ITAM has the sequence (D/E)YAAIX$_6$YVLL (SEQ ID No: 15). In another embodiment, the ITAM has the sequence (D/E)X$_{7-8}$(D/E)X$_{0-2}$YXX(L/I)X$_{6-8}$YXX(L/I) (SEQ ID No: 16). In another embodiment, the ITAM has the sequence (D/E)X$_{7-8}$(D/E)X$_{0-2}$YXXLX$_{6-8}$YXX(L/I) (SEQ ID No: 17). In another embodiment, the ITAM has the sequence DMPDDYEDENLYEGLNLDDCSMYEDI (SEQ ID No: 18). In another embodiment, the ITAM is homologous to SEQ ID No: 18. In another embodiment, the ITAM has the sequence (D/E)X$_{7-8}$(D/E)X$_{0-2}$YEGLX$_{6-8}$YEDI (SEQ ID No: 19). In another embodiment, the ITAM has the sequence (D/E)X$_7$(D/E)X$_2$YEGLX$_{6-8}$YEDI (SEQ ID No: 20). In another embodiment, the ITAM has the sequence (D/E)X$_{7-8}$(D/E)X$_2$YEGLX$_7$YEDI (SEQ ID No: 21). In another embodiment, the ITAM has the sequence (D/E)X$_7$(D/E)X$_2$YEGLX$_7$YEDI (SEQ ID No: 22). In another embodiment, the ITAM has the sequence EKFGVDMPDDYEDENLYEGLNLDDCSMYEDI (SEQ ID No: 23). In another embodiment, the ITAM is homologous to SEQ ID No: 23. In another embodiment, the ITAM has the sequence (D/E)X$_{7-8}$(D/E)X$_{0-2}$YEDEX$_{7-16}$YEDI (SEQ ID No: 24). In another embodiment, the ITAM has the sequence (D/E)X$_{9-10}$(D/E)X$_{0-1}$YEDEX$_{13}$YEDI (SEQ ID No: 25). In another embodiment, the ITAM has the sequence (D/E)X$_{7-8}$(D/E)X$_{0-2}$YEDEX$_2$YEGLX$_7$YEDI (SEQ ID No: 26). In another embodiment, the ITAM has the sequence (D/E)X$_{9-10}$(D/E)X$_{0-1}$YEDEX$_2$YEGLX$_7$YEDI (SEQ ID No: 27). In another embodiment, the ITAM has the sequence DKDDGKAGMEEDHTYEGLNIDQTATYEDI (SEQ ID No: 28). In another embodiment, the ITAM is homologous to SEQ ID No: 28. In another embodiment, the ITAM has the sequence (D/E)X$_{7-8}$(D/E)X$_{0-2}$YEGLX$_{6-8}$YEDI (SEQ ID No: 29). In another embodiment, the ITAM has the sequence (D/E)X$_{7-8}$(D/E)X$_2$YEGLX$_{6-8}$YEDI (SEQ ID No: 30). In another embodiment, the ITAM has the sequence (D/E)X$_{7-8}$(D/E)X$_{0-2}$YEGLX$_7$YEDI (SEQ ID No: 31). In another embodiment, the ITAM has the sequence (D/E)X$_{7-8}$(D/E)X$_2$YEGLX$_7$YEDI (SEQ ID No: 32). In another embodiment, the ITAM has the sequence SSCRLTNCLDSSAYVYAAIIVLMPPYVLL (SEQ ID No: 36). In another embodiment, the ITAM is homologous to SEQ ID No: 36. In another embodiment, the ITAM has the sequence (D/E)X$_5$YAAIX$_6$YVLL (SEQ ID No: 37). In another embodiment, the ITAM has the sequence RLTNCLDSSAYDYAAIIVKRPPYVLL (SEQ ID No: 38). In another embodiment, the ITAM is homologous to SEQ ID No: 38. In another embodiment, the ITAM has the sequence (D/E)X$_4$DYAAIX$_6$YVLL (SEQ ID No: 39). In another embodiment, the ITAM has the sequence DSSAYDYAAIIVKRPPYVLL (SEQ ID No: 40). In another embodiment, the ITAM is homologous to SEQ ID No: 40. In another embodiment, the ITAM has the sequence DX$_4$DYAAIX$_6$YVLL (SEQ ID No: 41). In another embodiment, the ITAM has the sequence PYDAEDGGDGGPYQPLRGQDPNQLYARL (SEQ ID No: 90). In another embodiment, the ITAM is homologous to SEQ ID No: 90. In another embodiment, the ITAM has the sequence GPYQPLRGQDPNQLYARLGGGGGNGTLPPPPYSPQRETSLHLYEEI (SEQ ID No: 91). In another embodiment, the ITAM is homologous to SEQ ID No: 91. In another embodiment, the ITAM has the sequence EDPYWGNGDRHSDYQPLGTQDQSLYLGL (SEQ ID No: 92). In another embodiment, the ITAM is homologous to SEQ ID No: 92. In another embodiment, the ITAM has the sequence PPYEDLDWGNGDRHSDYQPLGNQDPSLYLGL (SEQ ID No: 93). In another embodiment, the ITAM is homologous to SEQ ID No: 93. In another embodiment, the ITAM has the sequence YDAPSHRPPSYGGSGGYATLGQQEPSLYAGL (SEQ ID No: 94). In another embodiment, the ITAM is homologous to SEQ ID No: 94. In another embodiment, the ITAM has the sequence DRDGDPVPPDYDAPSHRPPSYGGSGGYATLGQQEPSLYAGL (SEQ ID No: 95). In another embodiment, the ITAM is homologous to SEQ ID No: 95. In another embodiment, the ITAM has the sequence LSKLTALVAVATWFAELMTYLVLPSANNIIVLSLLVAAEGIQSIYLLV (SEQ ID No: 96). In another embodiment, the ITAM is homologous to SEQ ID No: 96. In another embodiment, the ITAM has the sequence ESNEEPPPPYEDPYWGNGDRHSDYQPLGTQDQSLYLGL (SEQ ID No: 97). In another embodiment, the ITAM is homologous to SEQ ID No: 97. In another embodiment, the ITAM has the sequence EDSDWGNGDRHSDYQPLGNQDPSLYLGL (SEQ ID No: 98). In another embodiment, the ITAM is homologous to SEQ ID No: 98. In other embodiments, the ITAM has any of the ITAM sequences found in GenBank Accession Numbers AA086793-AA086822, inclusive, AAD53747-AAD53750, inclusive, Q9QGQ3-Q9QGQ6, inclusive, AAL50731-AAL50751, inclusive, AAK94430-AAK94430, inclusive, Q9WHI0-Q9WHI4, inclusive, Q9WHH8-Q9WHH9, inclusive, and AAD30529-AAD30535, inclusive. In other embodiments, the ITAM is homologous to any of the ITAM sequences found in the above GenBank Accession Numbers. In other embodiments, the ITAM has any of the ITAM sequences enumerated in the Examples herein. In another embodiment, the ITAM has any other ITAM sequence known in the art. Each possibility represents a separate embodiment of the present invention.

In another embodiment, more than one of the above ITAM sequences or ITAM motifs are targeted, inhibited, or blocked by a method of the present invention. In another embodiment, two ITAM sequences are targeted, inhibited, or blocked. In another embodiment, three ITAM sequences are targeted, inhibited, or blocked. In another embodiment, four ITAM sequences are targeted, inhibited, or blocked. In another embodiment, more than four ITAM sequences are targeted, inhibited, or blocked. Each possibility represents a separate embodiment of the present invention.

In another embodiment of methods and compositions of the present invention, the protein that interacts with the ITAM (i.e. the "first protein") is a cellular protein. In another embodiment, the protein is a signaling protein. In another embodiment, the protein is a tyrosine kinase. In another embodiment, the protein is a tyrosine kinase substrate. In another embodiment, the protein is a signaling protein. In another embodiment, the protein is a viral protein that acts as a signaling protein, tyrosine kinase, or tyrosine kinase substrate in eukaryotic cells. In another embodiment, the protein is any other type of protein known in the art. Each possibility represents a separate embodiment of the present invention.

The carcinoma that is the target of methods and compositions of the present invention is, in another embodiment, a breast cell carcinoma. In another embodiment, the carcinoma is an epithelial cell malignancy. In another embodiment, the carcinoma is a mammary epithelial cell malignancy. In other embodiments, the carcinoma is a ductal carcinoma (e.g. infiltrating ductal carcinoma) squamous cell carcinoma, squamous epithelial carcinoma, lobular carcinoma (e.g. of the breast), adenocarcinoma (e.g. an endometroid adenocarcinoma), small cell carcinoma, carcinoma of the vulva, renal cell carcinoma, non-small cell lung carcinoma, soft-tissue carcinoma, basal cell carcinoma, buccal cell carcinoma, thyroid/follicular carcinoma, sebaceous gland carcinoma, adrenal carcinoma, transitional cell carcinoma, urothelial carcinoma, fibrolamellar carcinoma, or hepatocellular carcinoma. In another embodiment, the carcinoma is any other carcinoma or type of carcinoma known in the art. Each possibility represents a separate embodiment of the present invention.

In another embodiment, the present invention provides a method of treating a sarcoma in a subject, comprising administering to the subject a compound that inhibits an interaction of a first protein and an ITAM of a second protein, thereby treating a sarcoma in a subject.

In another embodiment, the present invention provides a method of reducing an incidence of a sarcoma in a subject, comprising administering to the subject a compound that inhibits an interaction of a first protein and an ITAM of a second protein, thereby reducing an incidence of a sarcoma in a subject.

In another embodiment, the present invention provides a method of inhibiting a formation of a metastasis of a sarcoma in a subject, comprising administering to the subject a compound that inhibits an interaction of a first protein and an ITAM of a second protein, thereby inhibiting a formation of a metastasis of a sarcoma in a subject.

In another embodiment, the present invention provides a method of reducing an invasiveness of a metastasis of a sarcoma in a subject, comprising administering to the subject a compound that inhibits an interaction of a first protein and an ITAM of a second protein, thereby reducing an invasiveness of a metastasis of a sarcoma in a subject In another embodiment, the present invention provides a method of reversing a malignant transformation of a sarcoma in a subject, comprising administering to the subject a compound that inhibits an interaction of a first protein and an ITAM of a second protein, thereby reversing a malignant transformation of a sarcoma in a subject.

As provided herein (Example 20), findings of the present invention show that expression of a protein containing an ITAM, but not a mutant-ITAM-containing protein, is capable of transformation of connective tissue cells, as shown by multiple assays. These findings show that blocking association of an ITAM with cellular molecules and blocking ITAM-mediated signaling are effective strategies for preventing and reducing the incidence of sarcoma malignant transformation, treating sarcomas, inhibiting metastases, and reducing invasiveness of sarcoma cells.

Moreover, the present invention provides methods of modifying peptides of the present invention and identifying further improved peptides using models of sarcoma, both primary tumors and metastases (Examples 8, 11, and 31); or, in another embodiment, using colony formation assays (e.g. as described in Example 22); or, in another embodiment, using ITAM co-IP assays (e.g. as described in Example 23); or, in another embodiment, using ability to abrogate or reduce phosphorylation of an ITAM-containing protein (e.g. as described in Example 29); or, in another embodiment, using a focus formation assay (e.g. as described in Example 30). These methods facilitate, in another embodiment, selection of further improved ITAM-inhibitory peptides.

The sarcoma that is the target of methods of the present invention is, in one embodiment, a fibrosarcoma. In another embodiment, the sarcoma is a Kaposi's sarcoma. In another embodiment, the sarcoma is a connective tissue cell malignancy. In another embodiment, the sarcoma is a fibroblast-derived tumor. In another embodiment, the sarcoma is a Ewing Sarcoma. In another embodiment, the sarcoma is a neuroectodermal tumor (e.g. a primitive neuroectodermal tumor). In another embodiment, the sarcoma is a post-radiation sarcoma. In another embodiment, the sarcoma is a synovial cell sarcoma. In another embodiment, the sarcoma is a clear cell sarcoma. In another embodiment, the sarcoma is a rhabdomyosarcoma. In another embodiment, the sarcoma is a uterine sarcoma. In another embodiment, the sarcoma is an endometrial stromal sarcoma. In another embodiment, the sarcoma is an osteosarcoma. In another embodiment, the sarcoma is a chondrosarcoma. In another embodiment, the sarcoma is a leiomyosarcoma. In another embodiment, the sarcoma is an endothelial sarcoma. In another embodiment, the sarcoma is any other type of sarcoma known in the art. Each possibility represents a separate embodiment of the present invention.

In another embodiment, the present invention provides a method of treating an Epstein-Barr virus-induced malignancy in a subject, comprising administering to the subject a compound that inhibits an interaction of a first protein and an ITAM of a second protein, thereby treating an Epstein-Barr virus-induced malignancy in a subject.

In another embodiment, the present invention provides a method of reducing an incidence of an Epstein-Barr virus-induced malignancy in a subject, comprising administering to the subject a compound that inhibits an interaction of a first protein and an ITAM of a second protein, thereby reducing an incidence of an Epstein-Barr virus-induced malignancy in a subject.

In another embodiment, the present invention provides a method of inhibiting a formation of a metastasis of an Epstein-Barr virus-induced malignancy in a subject, comprising administering to the subject a compound that inhibits an interaction of a first protein and an ITAM of a second protein, thereby inhibiting a formation of a metastasis of an Epstein-Barr virus-induced malignancy in a subject.

In another embodiment, the present invention provides a method of reducing an invasiveness of a metastasis of a Epstein-Barr virus-induced malignancy in a subject, comprising administering to the subject a compound that inhibits an interaction of a first protein and an ITAM of a second protein, thereby reducing an invasiveness of a metastasis of a Epstein-Barr virus-induced malignancy in a subject In another embodiment, the present invention provides a method of reversing a malignant transformation of an Epstein-Barr virus-induced malignancy in a subject, comprising administering to the subject a compound that inhibits an interaction of a first protein and an ITAM of a second protein, thereby reversing a malignant transformation of an Epstein-Barr virus-induced malignancy in a subject.

As provided herein (Examples), findings of the present invention show that expression of a protein containing an ITAM, but not a mutant-ITAM-containing protein, is capable of transformation of multiple cell types, including cell types relevant to EBV-induced malignancies. Activity of cellular signaling molecules that associated with the ITAM (e.g. Syk kinase) was necessary for the transformation to occur. These findings show that blocking association of an ITAM with cellular molecules and blocking ITAM-mediated signaling are effective strategies for preventing and reducing the incidence of malignant transformation. In addition, testing of a peptide of the present invention showed that ITAM association-blocking peptides can not only prevent, but also reverse cell transformation. The LMP2A protein of EBV contains an ITAM. The findings of the present invention thus show that blocking association of the LMP2A ITAM with cellular molecules and blocking LMP2A ITAM-mediated signaling are effective strategies for preventing and reducing the incidence of malignant transformation, and for treatment and prevention of metastases of EBV-induced malignancies.

Moreover, the present invention provides methods of modifying peptides of the present invention and identifying further improved peptides using models of EBV-induced malignancies (Examples 8 and 10); or, in another embodiment, using colony formation assays (e.g. as described in Example 22); or, in another embodiment, using ITAM co-IP assays (e.g. as described in Example 23); or, in another embodiment, using ability to abrogate or reduce phosphorylation of an ITAM-containing protein (e.g. as described in Example 29); or, in another embodiment, using a focus formation assay (e.g. as described in Example 30). These methods facilitate, in another embodiment, selection of further improved ITAM-inhibitory peptides.

The Epstein-Barr virus-induced malignancy that is the target of methods of the present invention is, in one embodiment, a Burkitt's lymphoma. In another embodiment, the Epstein-Barr virus-induced malignancy is Hodgkin's disease. In another embodiment, the Epstein-Barr virus-induced malignancy is a nasopharyngeal carcinoma (NPC). In another embodiment, the Epstein-Barr virus-induced malignancy is post-transplant lymphoproliferative disease. In another embodiment, the Epstein-Barr virus-induced malignancy is any other Epstein-Barr virus-induced malignancy known in the art. Each possibility represents a separate embodiment of the present invention.

In another embodiment, the present invention provides a method of treating a B cell proliferative disorder in a subject, comprising administering to the subject a compound that inhibits an interaction of a first protein and an ITAM of a second protein, thereby treating a B cell proliferative disorder in a subject.

In another embodiment, the present invention provides a method of reducing an incidence of a B cell proliferative disorder in a subject, comprising administering to the subject a compound that inhibits an interaction of a first protein and an ITAM of a second protein, thereby reducing an incidence of a pathological immune cell activation in a subject.

In another embodiment, the present invention provides a method of treating a mast cell activation disorder in a subject, comprising administering to the subject a compound that inhibits an interaction of a first protein and an ITAM of a second protein, thereby treating a mast cell activation disorder in a subject.

In another embodiment, the present invention provides a method of reducing an incidence of a mast cell activation disorder in a subject, comprising administering to the subject a compound that inhibits an interaction of a first protein and an ITAM of a second protein, thereby reducing an incidence of a mast cell activation disorder in a subject.

In another embodiment, the mast cell activation disorder is a systemic mastocytosis. (in another embodiment, with a cutaneous manifestation [e.g. Urticaria Pigmentosa]; in another embodiment, without a cutaneous manifestation). In another embodiment, the mast cell activation disorder is an aggressive mastocytosis. In another embodiment, the mast cell activation disorder is an indolent mastocytosis. In another embodiment, the mast cell activation disorder is a mastocytosis with an associated hematologic disorder. In another embodiment, the mast cell activation disorder is a mast cell leukemia. In another embodiment, the mast cell activation disorder is a cutaneous mastocytosis. In another embodiment, the mast cell activation disorder is an urticaria pigmentosa. In another embodiment, the mast cell activation disorder is a telengiecstasia. In another embodiment, the mast cell activation disorder is a macularis eruptive perstans. In another embodiment, the mast cell activation disorder is a solitary mastocytoma. In another embodiment, the mast cell activation disorder is an urticaria pigmentosa. In another embodiment, the mast cell activation disorder is a diffuse cutaneous mastocytosis. In another embodiment, the mast cell activation disorder is any other mast cell activation disorder known in the art. Each possibility represents a separate embodiment of the present invention.

As provided herein (Example 7), findings of the present invention show that ITAM association-blocking peptides prevent BCR-induced proliferation, ITAM-based BCR signaling, and degranulation of RBL-2H3 mast cells. Thus, blocking association of an ITAM with cellular molecules and blocking ITAM-mediated signaling are effective strategies for preventing, reducing the incidence of, and treating B cell proliferative disorders and mast cell activation disorders.

Moreover, the present invention provides methods of modifying peptides of the present invention and identifying further improved peptides using models of carcinoma, both primary tumors and metastases (Examples 8 and 14); or, in another embodiment, using ITAM co-IP assays (e.g. as described in Example 23); or, in another embodiment, using ability to abrogate or reduce ITAM-dependent B cell activation (e.g. as described in Example 26); or, in another embodiment, using ability to abrogate or reduce ITAM-dependent BCR signaling (e.g. as described in Example 27); or, in another embodiment, using ability to abrogate or reduce ITAM-dependent mast cell degranulation (e.g. as described in Example 28); or, in another embodiment, using ability to abrogate or reduce phosphorylation of an ITAM-containing protein (e.g. as described in Example 29). These methods facilitate, in another embodiment, selection of further improved ITAM-inhibitory peptides.

The B cell proliferative disorder that is the target of methods and compositions of the present invention is, in another embodiment, a B cell lymphoma. In another embodiment, the B cell proliferative disorder is a B cell leukemia. In another embodiment, the B cell proliferative disorder is any other B cell proliferative disorder known in the art. Each possibility represents a separate embodiment of the present invention.

In another embodiment, the present invention provides a method of treating a thrombosis disorder in a subject, comprising administering to the subject a compound that inhibits an interaction of a first protein and an ITAM of a second protein, thereby treating a thrombosis disorder in a subject. Example 13 provides methods to facilitate selection of further improved ITAM-inhibitory peptides for this method.

In another embodiment, the present invention provides a method of reducing an incidence of a thrombosis disorder in a subject, comprising administering to the subject a compound that inhibits an interaction of a first protein and an ITAM of a second protein, thereby reducing an incidence of a thrombosis disorder in a subject.

In another embodiment, the embodiment, the thrombosis disorder is an autoimmune hemolytic anemia. In another embodiment, the embodiment, the thrombosis disorder is an idiopathic thrombocytopenic purpura. In another embodiment, the embodiment, the thrombosis disorder is any other thrombosis disorder known in the art. Each possibility represents a separate embodiment of the present invention.

In another embodiment, the present invention provides a method of treating a hantavirus pulmonary syndrome in a subject, comprising administering to the subject a compound that inhibits an interaction of a first protein and an ITAM of a second protein, thereby treating a hantavirus pulmonary syndrome in a subject. Example 12 provides methods to facilitate selection of further improved ITAM-inhibitory peptides for this method.

In another embodiment, the present invention provides a method of reducing an incidence of a hantavirus pulmonary syndrome in a subject, comprising administering to the subject a compound that inhibits an interaction of a first protein and an ITAM of a second protein, thereby reducing an incidence of a hantavirus pulmonary syndrome in a subject.

Figure 5:
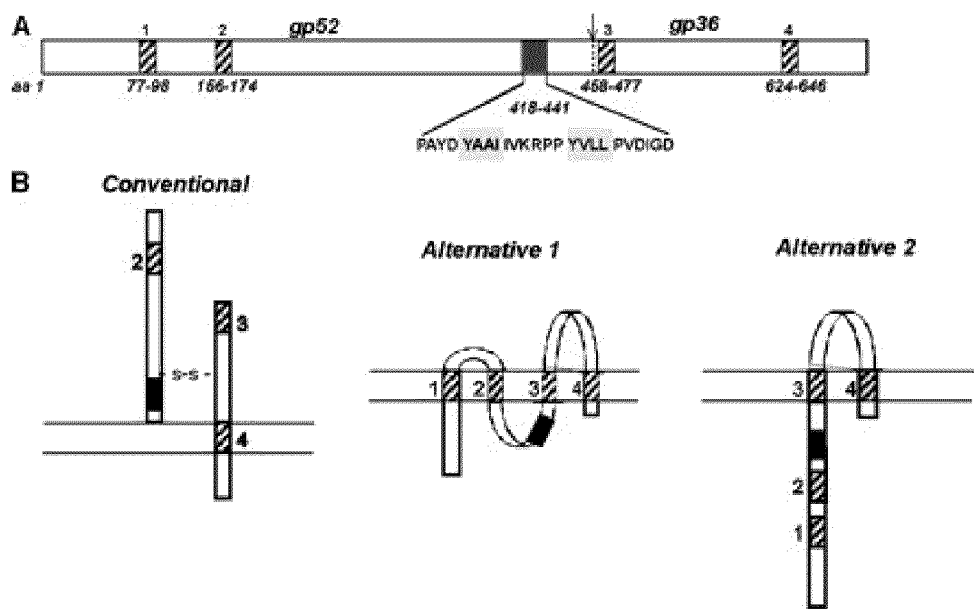
FIG. 5. MMTV envelope sequence, domains, and topological models. (A) Schematic representation of MMTV Env protein and its domains. Potential transmembrane domains are numbered and depicted in diagonally striped boxes. The ITAM region is marked in a shaded box and its sequence (SEQ ID NO: 1) is shown. (B) Models for the surface expression of mature MMTV Env on the host cell surface. The domains are marked as in A. Hydrophobicity scores for the transmembrane domains were as follows: 1: 1,489; 2: 699; 3: 2,658; and 4: 3,134.

As provided herein, findings of the present invention show that, under the conditions utilized herein, the ITAM motif of MMTV env is, in one embodiment, cytoplasmic. In another embodiment, all the transmembrane domains depicted in FIG. 5B are utilized. In another embodiment, transmembrane domains 3 and 4 are utilized (alternative model 1 and alternative model 2, respectively). Each possibility represents a separate embodiment of the present invention.

The compound of methods and compositions of the present invention is, in another embodiment, a peptide homologous to the ITAM that is targeted. In another embodiment, the compound comprises a peptide homologous to the ITAM. In another embodiment, the compound consists of a peptide homologous to the ITAM. In another embodiment, the compound is a derivative of a peptide homologous to the ITAM. Each possibility represents a separate embodiment of the present invention.

"Peptide" refers, in another embodiment, to a peptide containing only naturally occurring amino acids. In another embodiment, the term refers to a peptide that contains one or more modified amino acids. In another embodiment, the term refers to a peptide that contains one or more non-standard amino acids. In another embodiment, the term refers to peptide that has been chemically modified. In another embodiment, the modified or non-standard amino acid is incorporated after the N-terminal residue. In another embodiment, the modified or non-standard amino acid is incorporated in place of the N-terminal residue. In another embodiment, the modified or non-standard amino acid is incorporated after the C-terminal residue. In another embodiment, the modified or non-standard amino acid is incorporated in place of the C-terminal residue. In another embodiment, the modified or non-standard amino acid is incorporated at an intermediate residue. In another embodiment, the modified or non-standard amino acid is incorporated at a combination of one of the above positions. Each possibility represents a separate embodiment of the present invention.

In another embodiment, "peptide" refers to an oligomer of amino acid residues that are connected by peptide bonds. In another embodiment, the term refers to an oligomer comprising both naturally occurring and, optionally, modified amino acid residues that are connected by peptide bonds. In another embodiment, one of the above oligomers is chemically modified, in a manner enumerated herein. Each possibility represents a separate embodiment of the present invention.

In another embodiment, a peptide of the present invention is modified to improve its water-solubility. In another embodiment, the peptide is modified to improve its cell membrane-permeability. In another embodiment, the peptide is modified to improve its proteolytic stability. In another embodiment, the peptide is modified to improve its bioavailability. In another embodiment, the peptide is modified to improve its specificity for a particular ITAM sequence. In another embodiment, the peptide is modified to decrease its activity against one or more non-target sequences (e.g. other ITAM sequences). Each possibility represents a separate embodiment of the present invention.

In another embodiment, the peptide is modified by acetylation (Example 6). In other embodiments, the acyl group is an alkanoyl group, (e.g. acetyl), hexanoyl, octanoyl, an aroyl group, (e.g. benzoyl), or a blocking group e.g. Fmoc (fluorenylmethyl-O—CO—), carbobenzoxy(benzyl-O—CO—), monomethoxysuccinyl, naphthyl-NH—CO—, acetylaminocaproyl, or adamantyl-NH—CO—. In another embodiment, the modification is hydroxylation (e.g. on the C-terminal end). In another embodiment, the modification is amidation (in some embodiments, of the carboxyl terminal or of another free carboxyl groups). In another embodiment, the modification is formylation. In another embodiment, the modification is gamma-carboxyglutamic acid hydroxylation. In another embodiment, the modification is methylation. In another embodiment, the modification is phosphorylation. In another embodiment, the modification is sulfation. In another embodiment, the modification is glycosylation. In another embodiment, the modification is reduction. In another embodiment, the modification is oxidation. In another embodiment, the modification is disulfide modification. In another embodiment, the modification is introduction of a thioether bond. In another embodiment, the modification is introduction of a thiolester bond. In another embodiment, the modification is a backbone condensation. In another embodiment, the modification is biotinylation. In another embodiment, the modification is an esterification of the carboxyl terminal or of another free carboxyl or hydroxy group. In another embodiment, the modification is conjugation to a lipophilic moiety (e.g. caproyl, lauryl, or stearoyl). In another embodiment, the modification is conjugation to an antibody or other biological ligand. In another embodiment, the modification is any other modification of a peptide that is known in the art. Each possibility represents a separate embodiment of the present invention.

In another embodiment, a moiety that provides a net positive charge is incorporated onto the N-terminus of the peptide. In other embodiments, the moiety is a straight chain, branched, cyclic, or heterocyclic alkyl group; a straight chain, branched, cyclic, or heterocyclic alkanoyl group; or 1-15 additional amino acids independently selected from L-configuration or D-configuration amino acids, optionally substituted with a straight chain, branched, cyclic or heterocyclic alkyl group; or a straight chain, branched, cyclic or heterocyclic alkanoyl group.

In other embodiments, the C terminus of a peptide of the present invention is modified to comprise a free hydroxyl, an amide, an imide, a sugar, or 1-15 additional amino acids, optionally substituted with a free hydroxyl, an amide, an imide or a sugar. In another embodiment, the C-termini is modified in the same manner as the modified N-termini, described above. In another embodiment, the C terminus is modified with 2-acetamido-2-deoxyglucose. In another embodiment, the C terminus is modified by addition of triacetyl 2-acetamido-2-deoxyglucose. In another embodiment, the C terminus is modified by addition of a β-acetyl-2,3- diamino propionic acid group. Each possibility represents a separate embodiment of the present invention.

In another embodiment, the peptides of this invention are modified by addition of two adjacent amino acids that are resistant to cleavage by endopeptidases. In another embodiment, conventional inter-residue amide bonds are replaced by bonds resistant to proteases, (in other embodiments, a thioamide bond or a reduced amide bond).

The modified amino acid present in peptides of methods and compositions of the present invention is, in various embodiments, a D amino acid, pyrrolidone carboxylic acid, 2-aminoadipic acid, 3-aminoadipic acid, beta-alanine or beta-aminoproprionic acid, 2-aminobutyric acid, 4-aminobutyric acid or piperidinic acid, 6-aminocaproic acid, 6-aminoheptanoic acid, 2-aminoheptanoic acid, 2-aminoisobutyric acid, 3-aminoisobutyric acid, 2-aminopimelic acid, 2,4 diaminobutyric acid, desmosine, 2,2 diaminopimelic acid, 2,3 diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine or sarcosine, methylisoleucine, methyllysine, methylvaline, norvaline, norleucine, 6-aminohexanoic acid, citrulline, cysteic acid, cyclohexylalanine, alpha.-amino isobutyric acid, t-butylglycine, t-butylalanine and phenylglycine an N-alpha-methyl amino acid, a C-alpha-methyl amino acid, a beta-methyl amino acid, or orthinine. In another embodiment, the modified amino acid is any other modified amino acid known in the art. Each possibility represents a separate embodiment of the present invention.

"Comprises a peptide" refers, in one embodiment, to a molecule that contains one of the peptides enumerated above and a non-amino acid moiety attached to one or both ends of the peptide. The non-amino acid moiety is, in various embodiments, any suitable chemical group known in the art. Each possibility represents a separate embodiment of the present invention. In another embodiment, the non-amino acid moiety is attached to one or more of the intermediate peptide residues. In another embodiment, the non-amino acid moiety is attached to the peptide via a peptide bond. In another embodiment, the non-amino acid moiety is attached to the peptide via any other type of bond known in the art. Each possibility represents a separate embodiment of the present invention.

In another embodiment, the present invention provides a peptide having the sequence Ac-KRPPYVLL-OH (SEQ ID No: 2). In another embodiment, the peptide of methods and compositions of the present invention has a sequence homologous to SEQ ID No: 2. In another embodiment, the peptide has a sequence identical to KRPPYVLLPVDIGD (SEQ ID No: 33) or a fragment thereof. In another embodiment, the peptide has a sequence homologous to KRPPYVLLPVDIGD (SEQ ID No: 33) or a fragment thereof. In another embodiment, the peptide has a sequence identical to a fragment of PAYDYAAIIVKRPPYVLLPVDIGD (SEQ ID No: 1). In another embodiment, the peptide has a sequence homologous to a fragment of PAYDYAAIIVKRPPYVLLPVDIGD (SEQ ID No: 1). In another embodiment, the peptide has a sequence homologous to DMPDDYEDENLYEGLNLDDCSMYEDI (SEQ ID No: 18) or a fragment thereof. In another embodiment, the peptide has a sequence identical to DMPDDYEDENLYEGLNLDDCSMYEDI (SEQ ID No: 18) or a fragment thereof. In another embodiment, the peptide has a sequence identical to DCSMYEDI (SEQ ID No: 34) or a fragment thereof. In another embodiment, the peptide has a sequence homologous to DCSMYEDI (SEQ ID No: 34) or a fragment thereof. In another embodiment, the peptide has a sequence identical to a fragment of DKDDGKAGMEEDHTYEGLNIDQTATYEDI (SEQ ID No: 28). In another embodiment, the peptide has a sequence homologous to a fragment of DKDDGKAGMEEDHTYEGLNIDQTATYEDI (SEQ ID No: 28). In another embodiment, the peptide has a sequence identical to QTATYEDI (SEQ ID No: 35) or a fragment thereof. In another embodiment, the peptide has a sequence homologous to QTATYEDI (SEQ ID No: 35) or a fragment thereof. In another embodiment, the peptide has the sequence YVLL (SEQ ID No: 49). In another embodiment, the peptide has a sequence identical to KRPPYLVV (SEQ ID No: 89) or a fragment thereof. In another embodiment, the peptide has a sequence homologous to KRPPYLVV (SEQ ID No: 89) or a fragment thereof. In another embodiment, the peptide has a sequence identical to any other ITAM sequence enumerated herein. In another embodiment, the peptide has a sequence homologous to any other ITAM sequence enumerated herein. In another embodiment, the peptide has a sequence identical to any other ITAM motif enumerated herein. In another embodiment, the peptide has a sequence homologous to any other ITAM motif enumerated herein. Each possibility represents a separate embodiment of the present invention. In another embodiment, the peptide has a sequence identical to any other ITAM sequence known in the art. In another embodiment, the peptide has a sequence homologous to any other ITAM sequence known in the art. In another embodiment, the peptide has a sequence identical to any other ITAM motif known in the art. In another embodiment, the peptide has a sequence homologous to any other ITAM motif known in the art. Each possibility represents a separate embodiment of the present invention.

In another embodiment, the peptide of methods and compositions of the present invention is an ITAM inhibitory peptide. In other embodiments, the ITAM inhibited by the peptide of the present invention has any of the ITAM sequences of the present invention. Each possibility represents a separate embodiment of the present invention.

In another embodiment of methods and compositions of the present invention, the inhibitory compound or peptide blocks interaction of an ITAM motif with Syk2, ZAP70, or a related or similar cellular protein without blocking other cellular functions of the cellular protein. In another embodiment, the peptide preferentially inhibits signaling via a viral ITAM over one or more cellular ITAMs. In another embodiment, the preferential inhibition is due to a sequence difference between the viral ITAM and the cellular ITAMs. Each possibility represents a separate embodiment of the present invention.

In another embodiment, a peptide of the present invention is homologous to a peptide of SEQ ID No: 1-98. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

"Homology" refers, in another embodiment, to identity to a sequence selected from SEQ ID No: 1-98 of greater than 70%. In another embodiment, "homology" refers to identity to a sequence selected from SEQ ID No: 1-98 of greater than 72%. In another embodiment, "homology" refers to identity to one of SEQ ID No: 1-98 of greater than 75%. In another embodiment, "homology" refers to identity to a sequence selected from SEQ ID No: 1-98 of greater than 78%. In another embodiment, "homology" refers to identity to one of SEQ ID No: 1-98 of greater than 80%. In another embodiment, "homology" refers to identity to one of SEQ ID No: 1-98 of greater than 82%. In another embodiment, "homology" refers to identity to a sequence selected from SEQ ID No: 1-98 of greater than 83%. In another embodiment, "homology" refers to identity to one of SEQ ID No: 1-98 of greater than 85%. In another embodiment, "homology" refers to identity to one of SEQ ID No: 1-98 of greater than 87%. In another embodiment, "homology" refers to identity to a sequence selected from SEQ ID No: 1-98 of greater than 88%. In another embodiment, "homology" refers to identity to one of SEQ ID No: 1-98 of greater than 90%. In another embodiment, "homology" refers to identity to one of SEQ ID No: 1-98 of greater than 92%. In another embodiment, "homology" refers to identity to a sequence selected from SEQ ID No: 1-98 of greater than 93%. In another embodiment, "homology" refers to identity to one of SEQ ID No: 1-98 of greater than 95%. In another embodiment, "homology" refers to identity to a sequence selected from SEQ ID No: 1-98 of greater than 96%. In another embodiment, "homology" refers to identity to one of SEQ ID No: 1-98 of greater than 97%. In another embodiment, "homology" refers to identity to one of SEQ ID No: 1-98 of greater than 98%. In another embodiment, "homology" refers to identity to one of SEQ ID No: 1-98 of greater than 99%. In another embodiment, "homology" refers to identity to one of SEQ ID No: 1-98 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any amino acid sequence listed herein is determined, in another embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In other embodiments, the ITAM-inhibitory peptides of any of the methods described above have any of the characteristics of an ITAM-inhibitory peptide of the present invention. Each characteristic represents a separate embodiment of the present invention.

Methods for in vivo transformation assays are well known in the art and are described in the Examples herein. Three-dimensional recombinant basement membrane cultures provide, in another embodiment, an in vivo model of the acinar architecture of mammary epithelium. Mammary epithelial cells grown in three-dimensional cultures recapitulate, in another embodiment, numerous features of breast epithelium in vivo. These include the formation of growth-arrested polarized acini with hollow lumen and deposition of basement membrane components, such as collagen IV and laminin V. Three-dimensional cultures provide, in another embodiment, the appropriate structural and functional context for studying the events involved in morphogenesis of glandular epithelium.

In another embodiment, the present invention provides a method of screening inhibitors (in one embodiment, "peptide-based inhibitors") of ITAM-dependent signaling, comprising one of the assays described herein in the Examples. In another embodiment, the present invention provides a method of screening inhibitors of malignant transformation into a carcinoma cell, comprising one of the assays described herein in the Examples. In another embodiment, the present invention provides a method of screening inhibitors of malignant transformation into a sarcoma cell, comprising one of the assays described herein in the Examples. In another embodiment, the present invention provides a method of screening inhibitors of transformation into a Epstein-Barr virus-induced malignancy, comprising one of the assays described herein in the Examples. In another embodiment, the present invention provides a method of screening inhibitors of cancer cell metastasis, comprising one of the assays described herein in the Examples. In another embodiment, the present invention provides a method of screening inhibitors of a B cell proliferative disorder, comprising one of the assays described herein in the Examples. In another embodiment, the present invention provides a method of screening inhibitors of a mast cell activation disorder, comprising one of the assays described herein in the Examples. In another embodiment, the present invention provides a method of screening inhibitors of a thrombosis disorder, comprising one of the assays described herein in the Examples. In another embodiment, the present invention provides a method of screening inhibitors of a hantavirus pulmonary syndrome, comprising one of the assays described herein in the Examples. In another embodiment, the present invention provides a method of screening inhibitors of a any other disease or disorder that involves aberrant ITAM signaling, comprising one of the assays described herein in the Examples. Each possibility represents a separate embodiment of the present invention.

In one embodiment, the screening method is 3-dimensional culture assays of ITAM-containing protein-transfected cells (e.g. as described in Example 21); or, in another embodiment, colony formation assays (e.g. as described in Example 22); or, in another embodiment, ITAM co-IP assays (e.g. as described in Example 23); or, in another embodiment, ability to abrogate or reduce EMT (e.g. as described in Example 24); or, in another embodiment, ability to abrogate or reduce sensitivity to apoptosis (e.g. as described in Example 25); or, in another embodiment, ability to abrogate or reduce ITAM-dependent B cell activation (e.g. as described in Example 26); or, in another embodiment, ability to abrogate or reduce ITAM-dependent BCR signaling (e.g. as described in Example 27); or, in another embodiment, ability to abrogate or reduce ITAM-dependent mast cell degranulation (e.g. as described in Example 28); or, in another embodiment, ability to abrogate or reduce phosphorylation of an ITAM-containing protein (e.g. as described in Example 29); or, in another embodiment, a focus formation assay (e.g. as described in Example 30). Each possibility represents a separate embodiment of the present invention.

Various embodiments of dosage ranges of compounds of the present invention can be used in methods of the present invention. In one embodiment, the dosage is in the range of 1-10 mg/day. In another embodiment, the dosage is 2-10 mg/day. In another embodiment, the dosage is 3-10 mg/day. In another embodiment, the dosage is 5-10 mg/day. In another embodiment, the dosage is 2-20 mg/day. In another embodiment, the dosage is 3-20 mg/day. In another embodiment, the dosage is 5-20 mg/day. In another embodiment, the dosage is 10-20 mg/day. In another embodiment, the dosage is 3-40 mg/day. In another embodiment, the dosage is 5-40 mg/day. In another embodiment, the dosage is 10-40 mg/day. In another embodiment, the dosage is 20-40 mg/day. In another embodiment, the dosage is 5-50 mg/day. In another embodiment, the dosage is 10-50 mg/day. In another embodiment, the dosage is 20-50 mg/day. In one embodiment, the dosage is 1-100 mg/day. In another embodiment, the dosage is 2-100 mg/day. In another embodiment, the dosage is 3-100 mg/day. In another embodiment, the dosage is 5-100 mg/day. In another embodiment the dosage is 10-100 mg/day. In another embodiment the dosage is 20-100 mg/day. In another embodiment the dosage is 40-100 mg/day. In another embodiment the dosage is 60-100 mg/day.

In another embodiment, the dosage is 0.1 mg/day. In another embodiment, the dosage is 0.2 mg/day. In another embodiment, the dosage is 0.3 mg/day. In another embodiment, the dosage is 0.5 mg/day. In another embodiment, the dosage is 1 mg/day. In another embodiment, the dosage is 2 mg/day. In another embodiment, the dosage is 3 mg/day. In another embodiment, the dosage is 5 mg/day. In another embodiment, the dosage is 10 mg/day. In another embodiment, the dosage is 15 mg/day. In another embodiment, the dosage is 20 mg/day. In another embodiment, the dosage is 30 mg/day. In another embodiment, the dosage is 40 mg/day. In another embodiment, the dosage is 60 mg/day. In another embodiment, the dosage is 80 mg/day. In another embodiment, the dosage is 100 mg/day.

In another embodiment, the dosage is 10 µg/dose. In another embodiment, the dosage is 20 µg/dose. In another embodiment, the dosage is 30 µg/dose. In another embodiment, the dosage is 40 µg/dose. In another embodiment, the dosage is 60 µg/dose. In another embodiment, the dosage is 80 µg/dose. In another embodiment, the dosage is 100 µg/dose. In another embodiment, the dosage is 150 µg/dose. In another embodiment, the dosage is 200 µg/dose. In another embodiment, the dosage is 300 µg/dose. In another embodiment, the dosage is 400 µg/dose. In another embodiment, the dosage is 600 µg/dose. In another embodiment, the dosage is 800 µg/dose. In another embodiment, the dosage is 1000 µg/dose. In another embodiment, the dosage is 1.5 mg/dose. In another embodiment, the dosage is 2 mg/dose. In another embodiment, the dosage is 3 mg/dose. In another embodiment, the dosage is 5 mg/dose. In another embodiment, the dosage is 10 mg/dose. In another embodiment, the dosage is 15 mg/dose. In another embodiment, the dosage is 20 mg/dose. In another embodiment, the dosage is 30 mg/dose. In another embodiment, the dosage is 50 mg/dose. In another embodiment, the dosage is 80 mg/dose. In another embodiment, the dosage is 100 mg/dose.

In another embodiment, the dosage is 10-20 µg/dose. In another embodiment, the dosage is 20-30 µg/dose. In another embodiment, the dosage is 20-40 µg/dose. In another embodiment, the dosage is 30-60 µg/dose. In another embodiment, the dosage is 40-80 µg/dose. In another embodiment, the dosage is 50-100 µg/dose. In another embodiment, the dosage is 50-150 µg/dose.

In another embodiment, the dosage is 100-200 µg/dose. In another embodiment, the dosage is 200-300 µg/dose. In another embodiment, the dosage is 300-400 µg/dose. In another embodiment, the dosage is 400-600 µg/dose. In another embodiment, the dosage is 500-800 µg/dose. In another embodiment, the dosage is 800-1000 µg/dose. In another embodiment, the dosage is 1000-1500 µg/dose. In another embodiment, the dosage is 1500-2000 µg/dose. In another embodiment, the dosage is 2-3 mg/dose. In another embodiment, the dosage is 2-5 mg/dose. In another embodiment, the dosage is 2-10 mg/dose. In another embodiment, the dosage is 2-20 mg/dose. In another embodiment, the dosage is 2-30 mg/dose. In another embodiment, the dosage is 2-50 mg/dose. In another embodiment, the dosage is 2-80 mg/dose. In another embodiment, the dosage is 2-100 mg/dose. In another embodiment, the dosage is 3-10 mg/dose. In another embodiment, the dosage is 3-20 mg/dose. In another embodiment, the dosage is 3-30 mg/dose. In another embodiment, the dosage is 3-50 mg/dose. In another embodiment, the dosage is 3-80 mg/dose. In another embodiment, the dosage is 3-100 mg/dose. In another embodiment, the dosage is 5-10 mg/dose. In another embodiment, the dosage is 5-20 mg/dose. In another embodiment, the dosage is 5-30 mg/dose. In another embodiment, the dosage is 5-50 mg/dose. In another embodiment, the dosage is 5-80 mg/dose. In another embodiment, the dosage is 5-100 mg/dose. In another embodiment, the dosage is 10-20 mg/dose. In another embodiment, the dosage is 10-30 mg/dose. In another embodiment, the dosage is 10-50 mg/dose. In another embodiment, the dosage is 10-80 mg/dose. In another embodiment, the dosage is 10-100 mg/dose.

In another embodiment, the dosage is 10 µg/tablet. In another embodiment, the dosage is 20 µg/tablet. In another embodiment, the dosage is 30 µg/tablet. In another embodiment, the dosage is 40 µg/tablet. In another embodiment, the dosage is 60 µg/tablet. In another embodiment, the dosage is 80 µg/tablet. In another embodiment, the dosage is 100 µg/tablet. In another embodiment, the dosage is 150 µg/tablet. In another embodiment, the dosage is 200 µg/tablet. In another embodiment, the dosage is 300 µg/tablet. In another embodiment, the dosage is 400 µg/tablet. In another embodiment, the dosage is 600 µg/tablet. In another embodiment, the dosage is 800 µg/tablet. In another embodiment, the dosage is 1000 µg/tablet. In another embodiment, the dosage is 1.5 mg/tablet. In another embodiment, the dosage is 2 mg/tablet. In another embodiment, the dosage is 3 mg/tablet. In another embodiment, the dosage is 5 mg/tablet. In another embodiment, the dosage is 10 mg/tablet. In another embodiment, the dosage is 15 mg/tablet. In another embodiment, the dosage is 20 mg/tablet. In another embodiment, the dosage is 30 mg/tablet. In another embodiment, the dosage is 50 mg/tablet. In another embodiment, the dosage is 80 mg/tablet. In another embodiment, the dosage is 100 mg/tablet.

In another embodiment, the dosage is 10-20 µg/tablet. In another embodiment, the dosage is 20-30 µg/tablet. In another embodiment, the dosage is 20-40 µg/tablet. In another embodiment, the dosage is 30-60 µg/tablet. In another embodiment, the dosage is 40-80 µg/tablet. In another embodiment, the dosage is 50-100 µg/tablet. In another embodiment, the dosage is 50-150 µg/tablet.

In another embodiment, the dosage is 100-200 µg/tablet. In another embodiment, the dosage is 200-300 µg/tablet. In another embodiment, the dosage is 300-400 µg/tablet. In another embodiment, the dosage is 400-600 µg/tablet. In another embodiment, the dosage is 500-800 µg/tablet. In another embodiment, the dosage is 800-1000 µg/tablet. In another embodiment, the dosage is 1000-1500 µg/tablet. In another embodiment, the dosage is 1500-2000 µg/tablet. In another embodiment, the dosage is 2-3 mg/tablet. In another embodiment, the dosage is 2-5 mg/tablet. In another embodiment, the dosage is 2-10 mg/tablet. In another embodiment, the dosage is 2-20 mg/tablet. In another embodiment, the dosage is 2-30 mg/tablet. In another embodiment, the dosage is 2-50 mg/tablet. In another embodiment, the dosage is 2-80 mg/tablet. In another embodiment, the dosage is 2-100 mg/tablet. In another embodiment, the dosage is 3-10 mg/tablet. In another embodiment, the dosage is 3-20 mg/tablet. In another embodiment, the dosage is 3-30 mg/tablet. In another embodiment, the dosage is 3-50 mg/tablet. In another embodiment, the dosage is 3-80 mg/tablet. In another embodiment, the dosage is 3-100 mg/tablet. In another embodiment, the dosage is 5-10 mg/tablet. In another embodiment, the dosage is 5-20 mg/tablet. In another embodiment, the dosage is 5-30 mg/tablet. In another embodiment, the dosage is 5-50 mg/tablet. In another embodiment, the dosage is 5-80 mg/tablet. In another embodiment, the dosage is 5-100 mg/tablet. In another embodiment, the dosage is 10-20 mg/tablet. In another embodiment, the dosage is 10-30 mg/tablet.

In another embodiment, the dosage is 10-50 mg/tablet. In another embodiment, the dosage is 10-80 mg/tablet. In another embodiment, the dosage is 10-100 mg/tablet.

In another embodiment, the present invention provides a kit comprising a reagent utilized in performing a method of the present invention. In another embodiment, the present invention provides a kit comprising a composition, tool, or instrument of the present invention.

In another embodiment, the present invention relates to the use of an ITAM-inhibitor peptide and/or its analog, derivative, isomer, metabolite, pharmaceutically acceptable salt, pharmaceutical product, hydrate, N-oxide, or a combination thereof for treating, preventing, suppressing, inhibiting or reducing the incidence of the diseases and disorders enumerated herein. Thus, in one embodiment, the methods of the present invention comprise administering an analog of the peptide. In another embodiment, the methods of the present invention comprise administering a derivative of the peptide. In another embodiment, the methods of the present invention comprise administering an isomer of the peptide. In another embodiment, the methods of the present invention comprise administering a metabolite of the peptide. In another embodiment, the methods of the present invention comprise administering a pharmaceutically acceptable salt of the peptide. In another embodiment, the methods of the present invention comprise administering a pharmaceutical product of the peptide. In another embodiment, the methods of the present invention comprise administering a hydrate of the peptide. In another embodiment, the methods of the present invention comprise administering an N-oxide of the peptide. In another embodiment, the methods of the present invention comprise administering any combination of an analog, derivative, isomer, metabolite, pharmaceutically acceptable salt, pharmaceutical product, hydrate or N-oxide of the peptide.

In another embodiment, the term "isomer" includes, but, in another embodiment, is not limited to, optical isomers and analogs, structural isomers and analogs, conformational isomers and analogs, and the like.

The pharmaceutical compositions comprising the compound of the present invention can be, in another embodiment, administered to a subject by any method known to a person skilled in the art, such as parenterally, paracancerally, transmucosally, transdermally, intramuscularly, intravenously, intra-dermally, subcutaneously, intra-peritoneally, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the compositions such as salts, esters, N-oxides, and the like are prepared and applied as solutions, suspensions, or emulsions in a physiologically acceptable diluent with or without a pharmaceutical carrier.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of the active agent over a period of time.

In another embodiment, the active compound is delivered in a vesicle, e.g. a liposome. Each possibility represents a separate embodiment of the present invention.

EXPERIMENTAL DETAILS SECTION

Example 1

Expression of ITAM-Containing MMTV ENV Leads to Depolarization of Mammary Epithelial Acinar Structures Materials and Experimental Methods (Examples 1-4)

Cell Lines

NMuMG and MCF-10F cell lines were obtained from the American Type Culture Collection. MMTV-transfected clones of the NMuMG cell line were generated by transfecting NMuMG cells with MMTV. Clones expressing high levels of MMTV virions were selected. All NMuMG cell lines were maintained in DMEM containing 10% heat-inactivated FBS, 2 mM L-glutamine, 100 U/ml penicillin-streptomycin, and 10 µg/ml insulin at 37° C. and 5% $CO_2$.

Cell transfections were accomplished using the GenePorter® system (Gene Therapy Systems). The Q61 plasmid was used for complete envelope expression. Y>F mutations in the MMTV SU tyrosine residues were introduced using the Quickchange® XL kit (Stratagene). Stable pools were generated and maintained by sorting for SU$^{hi}$ expressing cells every 5-10 passages.

Flow Cytometry

Cells grown in two-dimensional cultures ($10^6$) were analyzed for flow cytometry on FACSCalibur (BD Biosciences). Goat polyclonal anti-SU (Dzuris J L et al, Expression of mouse mammary tumor virus envelope protein does not prevent superinfection in vivo or in vitro. Virology. 1999 Oct. 25; 263(2):418-26) or rat anti-human E-cadherin (Sigma-Aldrich) were used as primary antibody and donkey anti-goat IgG-FITC conjugated or goat anti-rat IgG-Cy5 conjugated (Jackson ImmunoResearch Laboratories) were used as secondary antibody. Normal goat IgGs or rat IgGs were used as the negative control.

Three-Dimensional Cultures

NMuMG cells ($5 \times 10^3$ cells per chamber) were cultured on Matrigel® (BD Biosciences) cushions. Assay medium (DMEM/F12 supplemented with 2% donor horse serum, 10 μg/ml insulin, 1 ng/ml cholera toxin, 100 μg/ml hydrocortisone, 50 U/ml penicillin, and 50 μg/ml streptomycin) containing 2% Matrigel was replaced every 4 days. The structures were analyzed, at a magnification of 20, on a Zeiss Axiovert 200M equipped with PCO SensiCam video camera and Slidebook® software (Intelligent Imaging Innovations). Cell staining was performed with rat anti-human Keratin-18 (Lab Vision), rat anti-human E-cadherin and goat anti-rat IgG-FITC conjugated antibodies (Jackson ImmunoResearch Laboratories), or goat anti-rat IgG-Alexa-555 conjugated antibodies (Molecular Probes). Quantification of structure size was performed using a 10×50-μm grid reticule (Fisher Scientific) and 20-100 structures were counted from each chamber. The inhibitors PP2 and Piceatannol (EMD) were added on day 3 of culture, and pictures were taken on day 6. In apoptosis assays, TNF (R&D Systems) or TRAIL (BIO-MOL Research Laboratories, Inc) were added on day 5 of culture, and pictures were taken on day 6. TUNEL assay was performed using a kit from Roche Applied Science (Indianapolis, Ind.).

Cell Lysis, Immunoprecipitation, and Western Blotting

Cells grown in two-dimensional cultures to confluency were stimulated for 2 min with 50 micromolar (μM) sodium pervanadate and harvested using cell lifters (Sigma-Aldrich). The cell pellet was lysed using PhosphoSafe® (EMD), supplemented with protease inhibitor cocktail (Roche Applied Science), and 0.5% weight per volume (wt/vol) sodium azide. Equivalent protein loads were used for immuno-precipitation (IP) as determined by Bichinchoninic Acid assay (Sigma-Aldrich). The antibody used for IP was mouse anti-SU black 8-6 monoclonal antibody (Burzyn D et al, Toll-like receptor 4-dependent activation of dendritic cells by a retrovirus. J. Virol. 2004 January; 78(2):576-84). For Western blotting, goat anti-SU or rabbit anti-Syk N-19 (Santa Cruz Biotechnology, Inc) polyclonal antibodies were used as primary antibodies, and donkey anti-goat IgG-alkaline phosphatase conjugated antibody or goat anti-rat IgG-alkaline phosphatase conjugated antibody (Jackson ImmunoResearch Laboratories) as secondary antibodies. For development and quantification, an ECF substrate was used followed by a scan using Storm 860 and analysis by ImageQuant 5.2 (all obtained from Amersham Biosciences).

Model of Human Cell Transformation

Spontaneously immortalized MCF-10F cells. MCF-10F cells and the transfected stable pools derived therefrom were maintained in DMEM:F-12 [1:1] medium with a 1.05 mM $Ca^{2+}$ concentration. After transfection, cells were assayed for determination of survival efficiency, colony efficiency, colony size, ductulogenic capacity, and invasiveness in Boyden chambers.

Colony Formation in Agar-Methocel

This technique was used as an in vitro assay for anchorage-independent growth, a parameter indicative of transformation. Cell lines were suspended at a density of $2 \times 10^4$ cells/ml in 2 ml of 0.8% methocel (Sigma-Aldrich) dissolved in DMEM:F-12 (1:1) medium containing 20% horse serum. Cells from each transfection group were plated in eight 24-well chambers pre-coated with 0.5 ml 5% agar base in DMEM:F-12 medium. Cells were fed with fresh feeding medium containing 0.8% methocel twice per week. The top four wells were stained with neutral red (1:300) 24 h after plating, and the total number of viable cells was counted. The bottom four wells were maintained in culture for 21 d, after which these wells were stained with neutral red, and colonies was counted. 10 colonies per well were measured by using a graduated reticule under microscope at a magnification of 10. Colony efficiency was determined by a count of the number of colonies >63 μm in diameter, and expressed as a percentage of the original number of viable cells 24 h after plating.

Ductulogenesis in Collagen Matrix

Parental MCF-10F and transfected cells were suspended at a final density of $2 \times 10^3$ cells/ml in 89.3% Vitrogen 100® collagen matrix (Collagen) and plated in four 24-well chambers precoated with 89.3% collagen. The cells were fed with fresh feeding medium containing 20% horse serum twice per week and were examined under an inverted microscope for a period of 21 d or longer to determine whether they formed ductal structures or grew as ball-like spherical masses. Structures were photographed, fixed in 10% neutral buffered formalin, embedded in paraffin, sectioned, and stained with hematoxylin-eosin for histological examination.

Invasion Assay

Trypsinized cells ($2.5 \times 10^4$) were seeded in the top chamber of BioCoat Matrigel Invasion Chambers® (BD Biosciences) and incubated for 22 h at 37° C. High calcium medium with 20% horse serum was used as a chemo-attractant. The filters were fixed, stained by Diff Quick® (Sigma-Aldrich), cut out, and mounted onto glass slides. The total number of cells that crossed the membrane was counted under a light microscope.

Results

The MMTV env gene encodes a type-1 membrane glycoprotein that, after proteolytic cleavage, exists as two mature proteins, the surface unit (SU or gp52) and the transmembrane unit (TM or gp36). SU contains the sequence: 418-PAYD<u>YAAI</u>IVKRPP<u>YVLL</u>PVDIGD-441 (SEQ ID No: 1) (FIG. 1 A).

To test whether the MMTV Env and its ITAM participate in MMTV-mediated transformation, three-dimensional cultures of NMuMG murine mammary epithelial cells were used. NMuMG cells, a normal murine mammary epithelial cell line, were stably transfected with both the SU and TM subunits of the MMTV Env; the stably transfected line is referred to as NMuMG.Q4. NMuMG.Q4 cells and mock-transfected NMuMG cells were seeded in three-dimensional cultures on a Matrigel® cushion. Within the first 6 days (d), WT mock-transfected NMuMG cells were observed to form a polarized disc structure (FIG. 1 C). By contrast, NMuMG.Q4 cells generated depolarized acini in frequencies ranging between 30-90% of all structures (nine independent experiments; FIG. 1B). The differences in depolarization are likely to reflect the variable Env expression levels in the NMuMG.Q4 cell line. When grown in two-dimensional cultures, the transfected cells did not appear morphologically different from the parental NMuMG cell line and did not exhibit a reproducible growth rate advantage.

To determine the contribution of the tyrosine residues in the ITAM domain of SU, an additional stable transfected pool was generated, NMuMG.F6, that expressed the MMTV Env with two Y>F substitutions (Env2xY>F) in the ITAM (amino acids 422 and 432 in MMTV [C3H] sequence). NMuMG.F6 was almost indistinguishable from wild-type or mock-transfected cells (FIG. 1 C, left panel). Enlarged structures were occasionally in three-dimensional cultures of wild-type or NMuMG.F6 cells, with low frequency, similar to that of mock-transfected NMuMG cells (six independent experiments; FIG. 1D). Differences in surface expression levels of MMTV SU did not account for the observed differences in transformation, as Env expression in the NMuMG.Q4 and NMuMG.F6 lines was equivalent (FIG. 1B, bottom). To show that the disruption in the three-dimensional morphology observed was not an artifactual result of Env over-expression, the Env expression levels in NMuMG.Q4 and NMuMG.F6 cells was compared to an MMTV-transfected clone (C1). The Env expression in the MMTV-transfected clone was higher, ruling out an artifactual effect (FIG. 1C, right panel).

Thus, in this in vitro model, MMTV Env expression induces depolarization of mammary epithelial acinar structures, in a manner dependent on tyrosine residues within the ITAM. These alterations are similar to those induced by known breast oncogenes such as ErbB2/HER2, showing that MMTV Env is capable of transformation of breast cells in an ITAM-dependent manner.

Example 2

Figure 2:
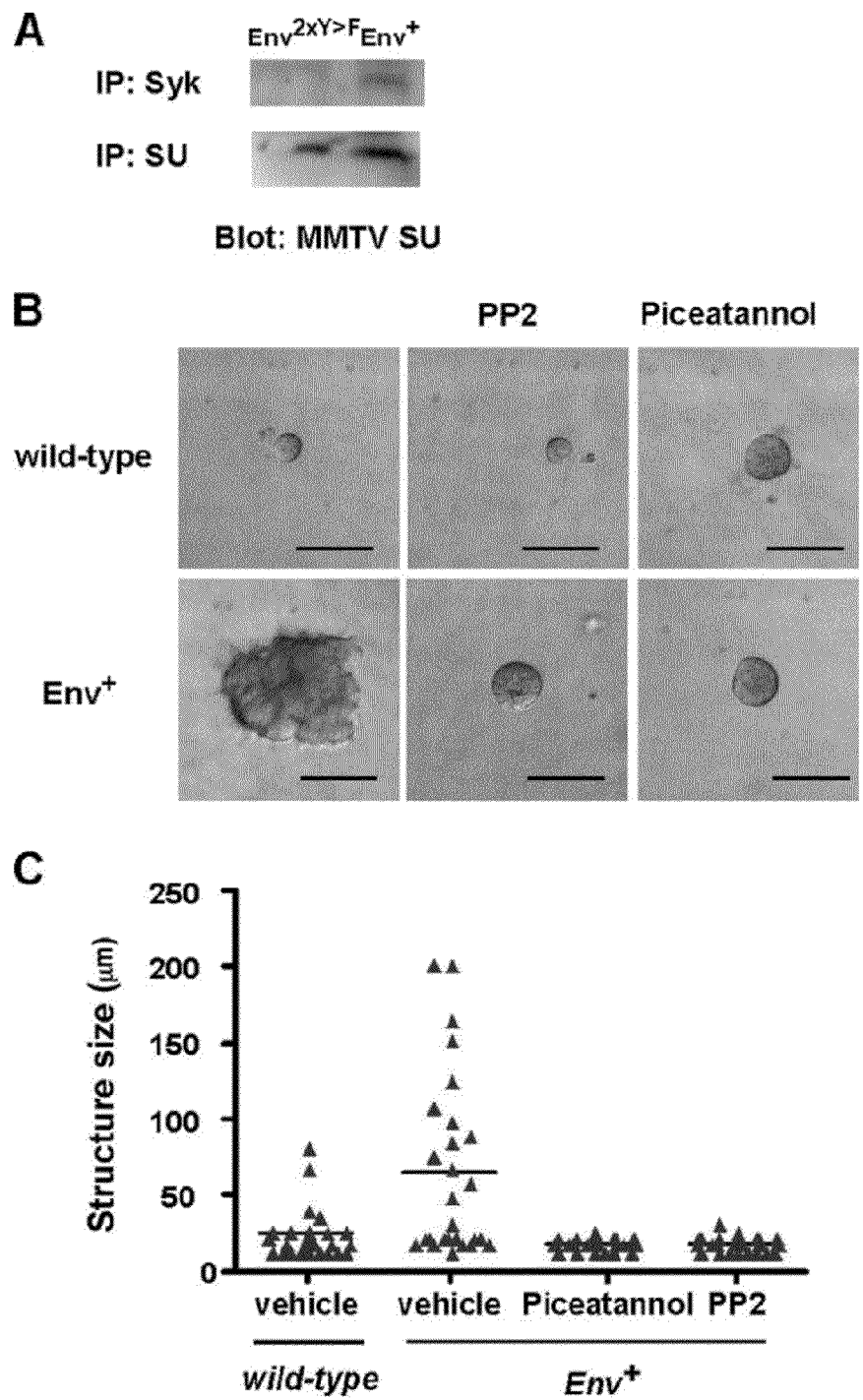
FIG. 2: Involvement of Src and Syk kinases in MMTV Env-induced cell transformation. (A) MMTV SU co-immunoprecipitated with Syk in a tyrosine-dependent manner. Mutated envelope-transfected ("$Env^{2xY>F}$") and unmutated envelope-transfected ("$Env^+$") two-dimensional cultures were treated with sodium pervanadate, lysed, normalized for total protein content, and subjected to MMTV SU or Syk IP. A Western blot for MMTV SU is depicted. Syk co-immunoprecipitated only with Env, but not with $Env^{2xY>F}$. (B) un-transfected ("wild-type") and unmutated envelope-transfected cultures were treated on day 3 three dimensionally with either normal assay media, PP2 (500 ng/ml), or Piceatannol (500 ng/ml), then imaged on day 6. Bars, 50 Mm. (C) Quantification of structure size in a representative experiment. Black bars represent the median for each culture.

SRC and SYK Tyrosine Kinases Contribute to MMTV ENV-Induced Acinar Depolarization In lymphocytes, ITAM signaling is dependent, under the conditions utilized herein, on activity of two tyrosine kinase families, the Src family kinases and the smaller Syk/Zap-70 family kinases. To directly show the role of the SU ITAM domain in signaling, direct interaction between the MMTV SU and Syk kinase was measured in the presence of tyrosine phosphatase inhibitors. Up to 34% SU protein co-immunoprecipitated with Syk (three independent experiments; FIG. 2 A). To confirm this finding, pharmacologic inhibitors of either Src (PP2) or Syk/ZAP70 (piceatannol) were shown to be sufficient to block morphological changes associated with Env transformation (FIG. 2B; quantification for one representative experiment depicted in FIG. 2C).

These findings provide further evidence that the ITAM was responsible for the observed cell transformation.

Example 3

MMTV ENV-Expressing Cells Exhibit a Transformed Mammary Epithelial Phenotype

NMuMG cells stably expressing infectious MMTV virus were also evaluated. These cells (MMTV$^+$ cells) exhibited morphological features resembling mesenchymal cells in three-dimensional cultures and a greater degree of depolarization in comparison with NMuMG.Q4 cells (FIG. 3A). A higher level of surface MMTV SU expression (FIG. 1C) or positional effects due to virus integration and long-term culture likely accounts for the differences between the MMTV$^+$ cells and the NMuMG.Q4 cells.

NMuMG.Q4 and MMTV$^+$ cells both exhibited down-regulation of Keratin-18 and E-cadherin expression, indicators of epithelial-mesenchymal transition, (FIG. 3 B, left panel), while expression of these markers in NMuMG.F6 cells closely resembled wild-type and mock-transfected cells. Down-regulation of E-cadherin surface expression could also be detected in Env-expressing cells maintained in two-dimensional cultures (FIG. 3 B, right panel).

Sensitivity to apoptosis induced by TNF-related apoptosis-inducing ligand (TRAIL) and TNF marks transformation and depolarization in many three-dimensional mammary epithelial culture systems. Accordingly, sensitivity of the Env-expressing cells to the pro-apoptotic effects of these agents was tested. As depicted in FIG. 3C, Env-expressing but not WT or mock-transfected cells were be sensitive to these agents, as determined by a marked attenuation in growth and loss of the spreading, nonpolarized structures exhibited in the absence of TNF or TRAIL.

Thus, MMTV Env expression in epithelial results in epithelial-mesenchymal transition.

Example 4

Expression of MMTV ENV Leads to Human Mammary Epithelial Cell Transformation

To determine whether Env expression leads to phenotypes normally associated with breast malignancy in primary human mammary epithelial cells, ability of MMTV Env to transform human mammary epithelial cells was determined. Stable transfectants of the primary human mammary epithelial line, MCF-10F, were generated, expressing either WT Env (MCF-10F.Q400) or the Env2xY>F envelope mutant (MCF-10F.Y1). Two assays were used as correlates of cell transformation: colony formation in agar-methocel and three-dimensional growth in a collagen matrix. Although both cell lines produced colonies, colony formation in agar-methocel in the Env-expressing cells was significantly and reproducibly more efficient in MCF-10F.Q400 cells (55-90%) compared with MCF-10F.Y1 cells (25-40%) (FIG. 4A, right panel). In addition, the MCF-10F.Q400 colonies were approximately twofold larger than those of MCF-10F.Y1 cells (FIG. 4A, left panel). These differences were more evident at earlier time points, where identifiable Env-expressing colonies were detected as early as 5 d in culture.

Figure 4:
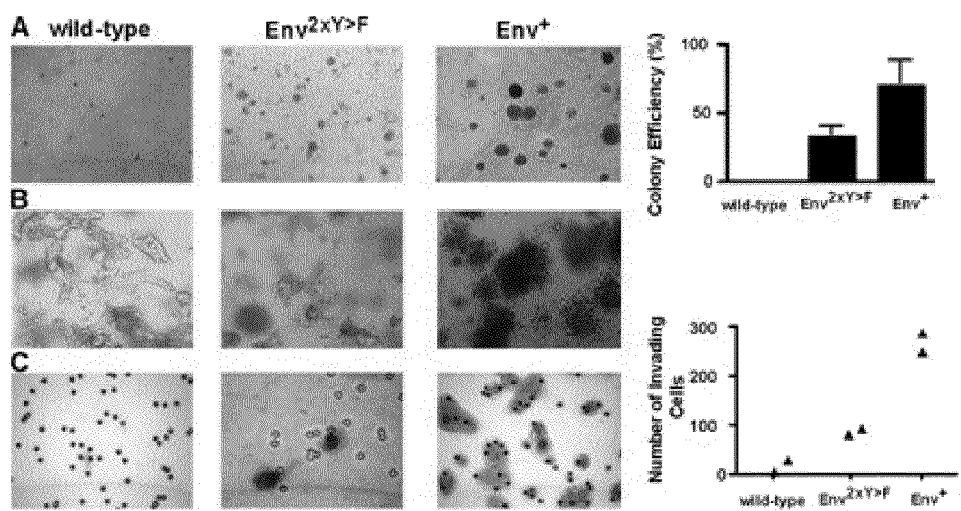
FIG. 4. MMTV Env also transforms human mammary epithelial cells. (A) Left panel: Colony formation assay for un-transfected ("wild-type"), mutated envelope-transfected ("$Env^{2xY>F}$"), and unmutated envelope-transfected ("$Env^+$") MCF-10F cells. Colonies were defined as cell clusters >60 µm in size. Right panel: The percentage of colonies formed in five agar-methocel cultures in an experiment representative of three independent experiments. (B) Representative images from collagen-matrix cultures of un-transfected, mutated envelope-transfected, and unmutated envelope-transfected MCF-10F cell lines (experiment representative of three independent experiments). Ductal structures are visible in wild-type cultures. Complete loss of ductal structure was observed in $Env^+$ cultures, whereas $Env^{2xY>F}$ cells exhibited a mixed phenotype. (C) Representative images from invasion assays of un-transfected ("wild-type"), $Env^{2xY>F}$, and $Env^+$ MCF-10F cells. Left panel: Stained mesh after the completion of the invasion assays. Invading cells were visualized by stain. The right panel depicts total invading cell counts from a representative experiment (in duplicate) out of three independent experiments.

The transforming properties of the Env protein in human cells were also detected using a collagen matrix assay, wherein mammary epithelial cells form ductal structures resembling their organization in the mammary gland. In MCF-10F.Q400 cells, notable loss of ductal structure (only spherical structures were observed) was observed in comparison with wild-type (MCF-10F.Q400) cells and ITAM mutant (MCF-10F.Y1) cells (FIG. 4 B).

In addition, Matrigel® invasion assays were conducted to evaluate the invasive properties of Env-expressing human cells. As depicted in FIG. 4C, MCF-10F.Y1 cells were only mildly invasive (<100 cells/25,000 cells seeded), whereas MCF-10F.Q400 cells were highly invasive, with more than twice as many cells scored.

These findings demonstrate that expression of a viral ITAM-containing protein confers transformation upon human mammary epithelial cells.

Example 5

Inhibition of ITAM-SYK Interactions using Synthetic ITAM Analogues

Materials and Experimental Methods (Examples 5-7)

Cells and Peptides

The NMuMG, Mm5MT, HEK-293T, NIH3T3, Bal-17 and RBL-2H3 cell lines were obtained from the American Type Culture Collection. NMuMG and Mm5MT cell lines were maintained in DMEM containing 10% heat-inactivated FBS, 2 mM L-glutamine, 100 U/ml penicillin-streptomycin, and 10 μg/ml insulin at 37° C. and 10% $CO_2$. HEK-293T and NIH3T3 cells were grown in DMEM containing 10% heat-inactivated FBS, 2 mM L-glutamine, and 100 U/ml penicillin-streptomycin at 37° C. and 10% CO2. Bal-17 cells were grown in RPMI containing 10% heat-inactivated FBS, 2 mM L-glutamine, 100 U/ml penicillin-streptomycin and 50 mM β-mercapto-ethanol at 37° C. and 5% $CO_2$. RBL-2H3 cells were grown in RPMI containing 15% heat-inactivated FBS, 2 mM L-glutamine and 100 U/ml penicillin-streptomycin at 37° C. and 5% $CO_2$.

Peptide synthesis was performed commercially by Global Peptide Services (purity >90%).

Florescent Constructs and Laser Scanning Microscopy

Peptide conjugates were produced by QuikChange XL® kit from Stratagene. The dsRed2-C1 construct (BD Clontech) was modified using the following primers: dsRed.YVLL: 5'-CCACCTGTTCCTGTATGTGCTGCTAT-GAAGATCTCGAGCTC-3' (SEQ ID No 42); and 5'-GGTG-GACAAGGACATACACGACGATACTTCTA-GAGCTCGAG-3 (SEQ ID No 43).

dsRed.KRPPYVLL: 5'-CCTGTTCCTGAAGAGGC-CATATGTGCTGCTATAGAGATCTCGAG-3' (SEQ ID No 44); and 5'-CGACAAGGACTTCTCCGGCGGTATACAC-GACGATATCTCTAGAGCTC-3' (SEQ ID No 45). The Syk-eGFP construct was a provided by Dr. Robert Geahlen (Purdue University).

For laser scanning microscopy a Zeiss LSM510 META laser scanning confocal module on a Zeiss Axiovert 200M inverted microscope was used. Objective used: C-APO 40×/1.2 water DIC. Lasers: 488 nm laser line from Argon laser (30 mW) for eGFP excitation; 543 nm laser line from HeNe laser (1 mW) for dsRed excitation. Analysis was performed on Zeiss LSM510 META v3.2 software.

Peptide:Syk Binding Assay

Whole cell lyastes of Bal-17 B cells ($3 \times 10^7$) were used for quantification of ITAM peptide interactions. Equivalent cell lysates were mixed with either biotin-KRPPAVLL (control peptide; SEQ ID No 46) or biotin-KRPPYVLL (ITAM peptide; SEQ ID No 47) in concentration between 10-50 μM. Pull-downs were performed with Immobilized Neutravidin Protein (Pierce), as previously described. The resulting lysate pull-downs were run on SDS-PAGE were detected by Western blotting with rabbit anti-Syk antibody (N-19, Santa Cruz). Donkey anti-rabbit IgG-alkaline phosphatase conjugated antibody was used as a secondary antibody (Jackson ImmunoResearch Laboratories). For development and quantification, an ECF substrate was used followed by a scan using Storm 860 and analysis by ImageQuant 5.2 (all obtained from Amersham Biosciences).

Three-Dimensional Acinar Cultures

NmuMG (wild-type or Env-expressing) or Mm5MT cells ($10^4$) were incubated on Matrigel (BD Labware) for six days, as described previously. Cells were treated with or without ITAM peptide (10 μM) or the Syk inhibitors piceatannol (1 μg/ml) and SI-31 (100 nM) (EMD). The acinar structures were analyzed and captured, at a magnification of 20×, on a Zeiss Axiovert 200M equipped with PCO SensiCam video camera and Slidebook v4 software (Intelligent Imaging Innovations). Three-dimensional structures >50 μm were considered enlarged. Data shown is based on size of 50 random acini.

Colony Formation Assay

NIH3T3 cells expressing the ITAM-containing MAHB chimera ($1 \times 10^4$) were suspended in 0.3% agar in DMEM containing 10% FBS. Cells from each transduction group were plated in 6-well plates pre-coated with 0.6% agar base in DMEM containing 10% FBS. Cells were fed with fresh top agar (0.3% agar in DMEM with 10% FBS, with or without ITAM peptide) every 5 days. Colonies were counted and measured using a graduated reticule under microscope at 10× magnification on day 21.

B lymphocyte Stimulation and Proliferation

Proliferation of mouse splenic B cells: cells ($5 \times 10^5$) were incubated for 48 h in the presence or absence of 20 μM peptide and stimulated with 10 μg/ml anti-BCR antibodies (Jackson ImmunoResearch Laboratories), LPS (Sigma) or anti-CD40 antibodies (BD Pharmingen). [$^3$H] Thymidine incorporation (1 μCi/well) was measured in the last 4 h of the experiment.

Inhibition of tyrosine phosphorylation was confirmed by Western blotting. Splenic B cells ($10^7$) were pre-incubated with 0-100 μM ITAM peptide for 3 h at 37° C. and then stimulated with anti-BCR antibodies as above for further 5 min. Lysates (20 μg/lane) were run on SDS-PAGE, blotted and detected with anti-phosphotyrosine antibody (4G10-HRP; Upstate Biotech). Molecular weights shown are based on the molecular weight markers.

FcεR1-Mediated Degranulation of RBL-2H3 Cells

The effect of ITAM peptide on mast cell function was evaluated by degranulation induced by FcεR1 cross-linking. RBL-2H3 cells ($5 \times 10^4$) were incubated overnight with anti-DNP IgE (1 μg/ml). Subsequently, degranulation was induced with DNP-HSA (10 ng/ml, 2 h), in the presence or absence of ITAM peptide (25 μM). Degranulation, as detected by hexosaminidase activity, is depicted as percent of maximal activity obtained from whole cell lysates.

Results

Figure 6A:
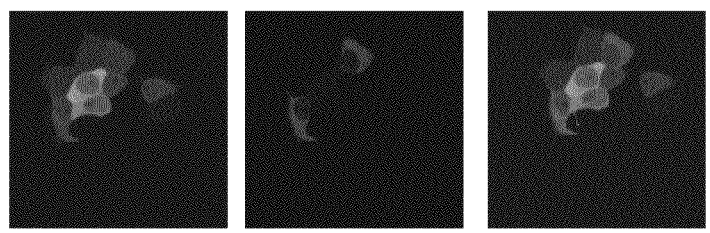
FIG. 6. Interaction of ITAM peptide with Syk kinase. (A) Human 293T cells were transiently transfected with empty dsRed construct (row i), dsRed.YVLL (SEQ ID NO: 49) (row ii), or dsRed.KRPPYVLL (SEQ ID NO: 2) (row iii) fusion proteins, along with Syk-GFP. Single channel images show the expression of either dsRed (left panels) or GFP (middle panels) constructs. The right panels of rows i-iii show a merged image of these constructs. The extreme right panel in row iii is enhanced view of the dsRed channel, which was weak for the dsRed.KRPPYVLL (SEQ ID NO: 49) construct. Co-localization of Syk and the peptides is quantified in B-C. (D) Bal-17 B cell lyastes were used for quantification of ITAM peptide interactions. Equivalent amounts of cell lysates were mixed with either biotin-KRPPAVLL (SEQ ID NO: 46) (control peptide) or biotin-KRPPYVLL (SEQ ID NO: 49) (ITAM peptide) in concentration between 10-50 µM. Pull-downs were detected with anti-Syk antibody (upper panel) and quantified (lower panel).
Figure 6A:
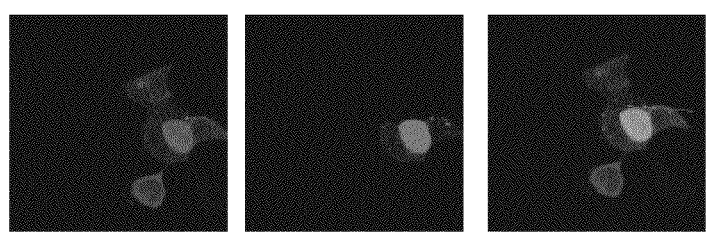
Figure 6A:
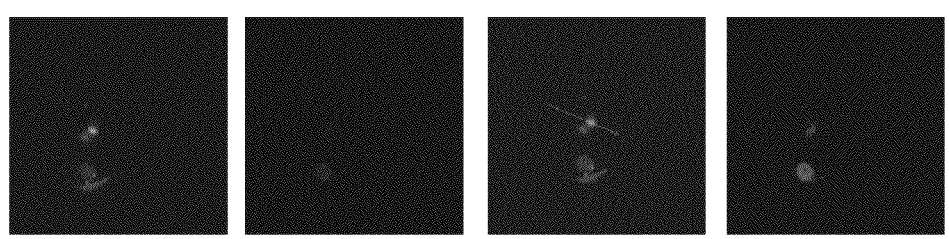

A water-soluble fragment of the MMTV ITAM was identified: 429-KRPPYVLL-435 (SEQ ID No: 48). dsRed chimera proteins were generated with 4 amino acids of this ITAM fragment or the entire fragment (dsRed.YVLL (SEQ ID No: 49) and dsRed.KRPPYVLL, respectively). Human 293T cells were transiently transfected with the dsRed constructs and with a Syk-GFP fusion protein, and co-localization of the florescent proteins was determined by confocal microscopy (FIG. 6a). In cells expressing the empty dsRed vector and Syk-GFP, the signal for both florescent proteins was diffuse and did not co-localize. The 4 amino acid (AA) chimera (dsRed.YVLL) was strongly expressed and co-localization was readily observed, although some Syk-GFP could be detected independently of the dsRed construct. The 8 AA chimera (dsRed.KRPPYVLL) was expressed to a lesser extent, but co-localization was still detected.

Figure 6B:
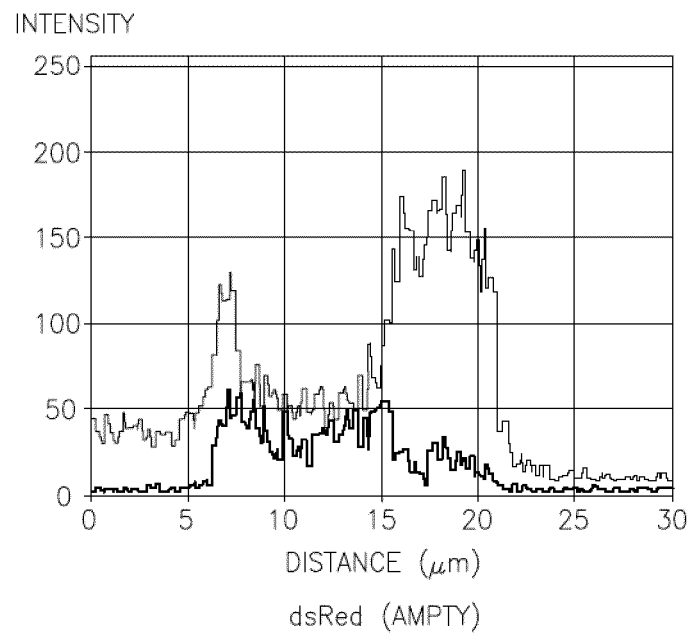
Figure 6B:
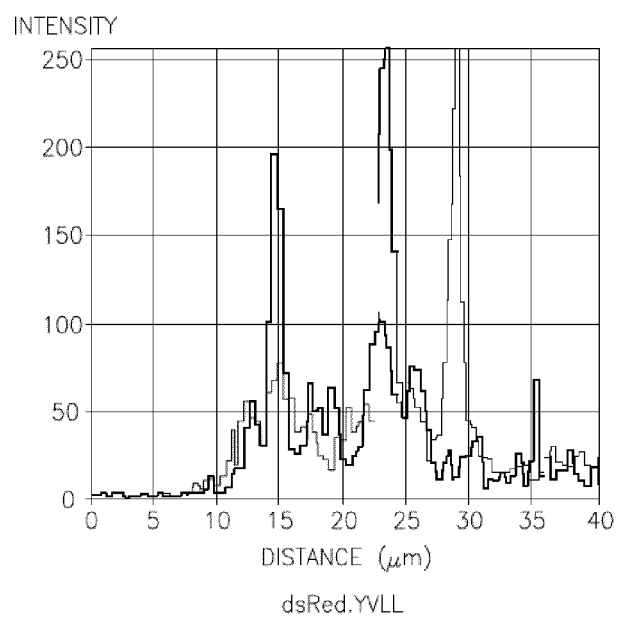
Figure 6C:
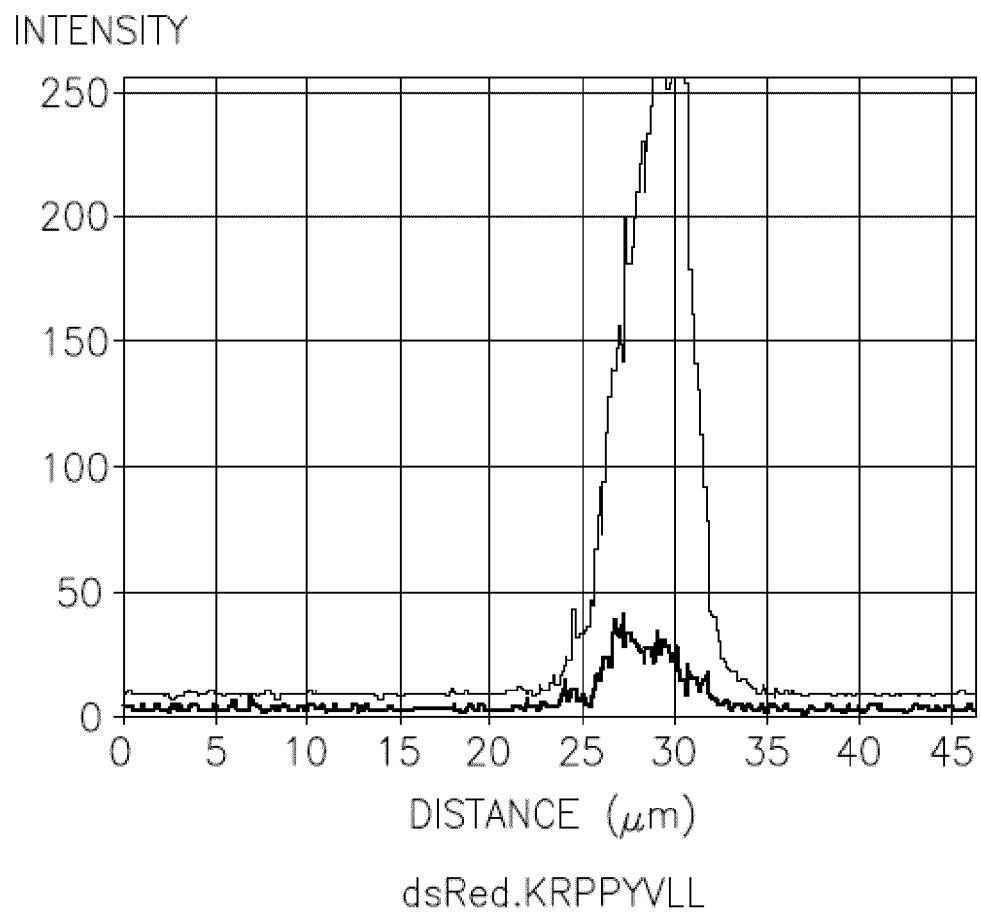
Figure 6D:
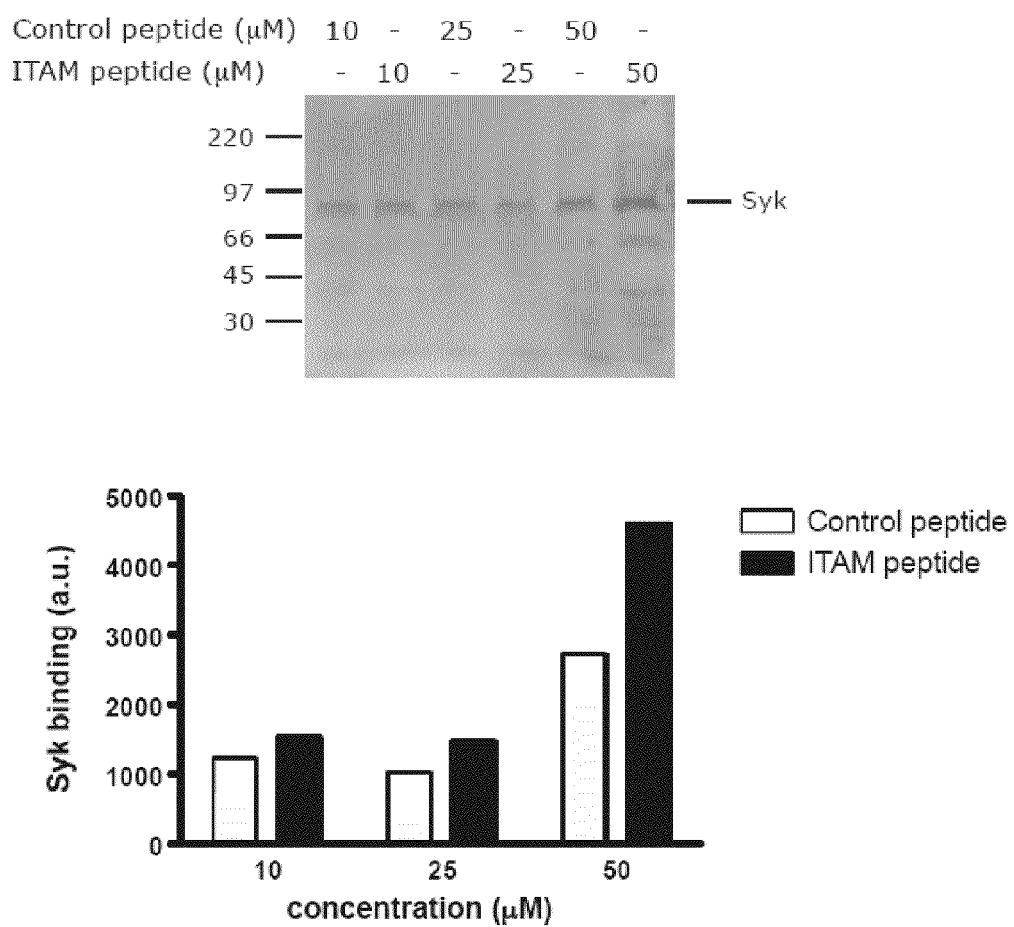

To confirm specific binding of the ITAM peptide to Syk, pull-down assays of biotin-KRPPYVLL from whole cell lysates were performed. When compared to a control peptide with a tyrosine to alanine substitution (biotin-KRPPAVLL;

SEQ ID No: 46), a substantial amount of Syk could be detected at a concentration of 50 µM (1.5- to 2-fold over the control, n=3). (FIG. 6B).

Thus, synthetic peptides of the present invention are capable of stable interaction with ITAM-binding proteins.

Example 6

Figure 7:
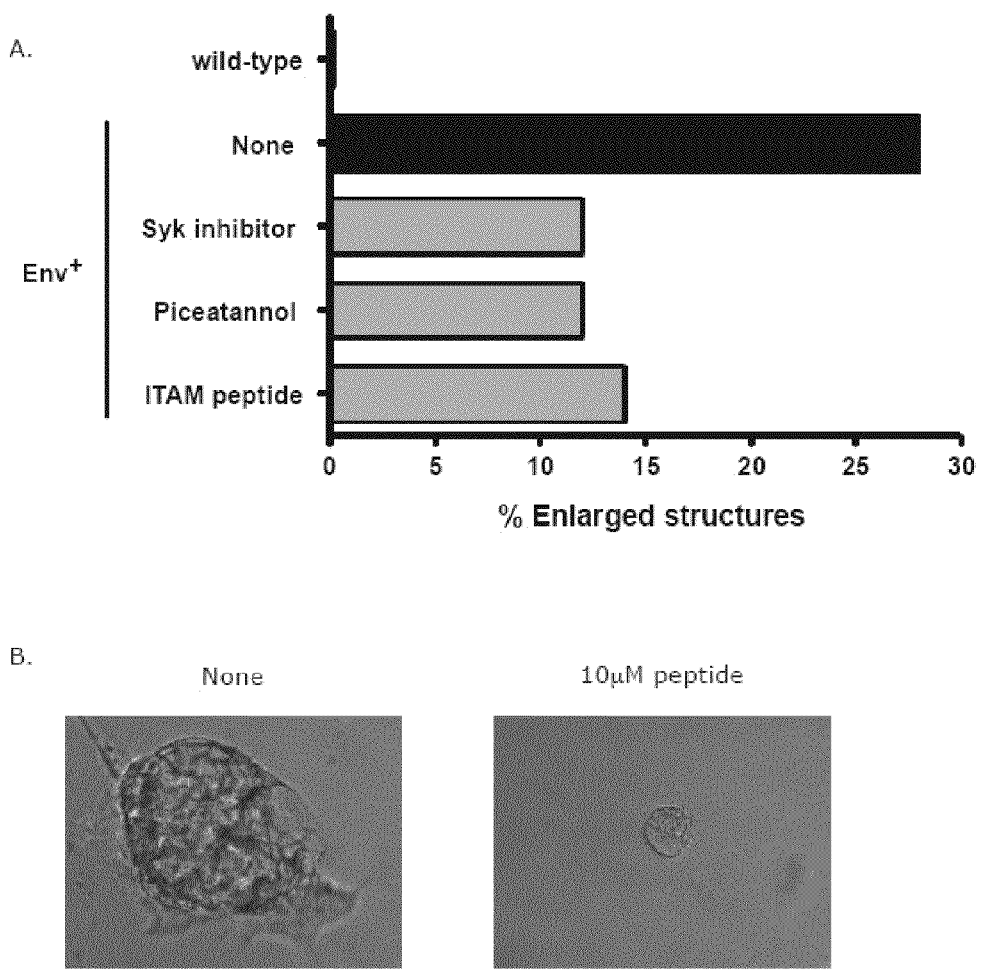
FIG. 7. MMTV Env-induced mammary epithelial transformation in 3D cultures depends on ITAM:Syk inteaction. Wild-type or Env-expressing NmuMG cells were incubated on Matrigel® for six days, in the presence or absence of 10 µM ITAM peptide or the Syk inhibitors piceatannol (1 µg/ml) and SI-31 (100 nM). Three-dimensional structures >50 µm were considered enlarged. (A) The percentage of enlarged structures is shown for each treatment. (B) Pictures of enlarged (top) and normal size 3D structures (bottom).

ITAM-Based Peptide is Comparable to Syk and Src Inhibition of ITAM-Induced Transformation An ITAM peptide of the present invention (Ac-KRP-PYVLL-OH) (SEQ ID No: 2), designed to block the interaction of Syk/Zap70 with the MMTV Env ITAM motif, was then tested as an inhibitor of transformation of mammary epithelial cells by MMTV Env expression. In 3D cultures, untransformed mammary epithelial cells form round hollow acinar structures. By contrast, cells expressing MMTV Env exhibit enlarged 3D acinar structures and resemble the epithelial to mesnchymal transition, as described hereinabove. Synthetic peptide inhibitors of the present invention were compared to Src and Syk kinase inhibitors for their ability to reverse the transformed phenotype to normal round acini. The ITAM peptide at 10 µM concentration was as effective in phenotypic reversal as the Src inhibitor PP2 and Syk inhibitors Piceatannol and SI-31 (FIG. 7). By contrast, integrin-dependent polarization of the acini was not affected by the peptides.

Figure 8:
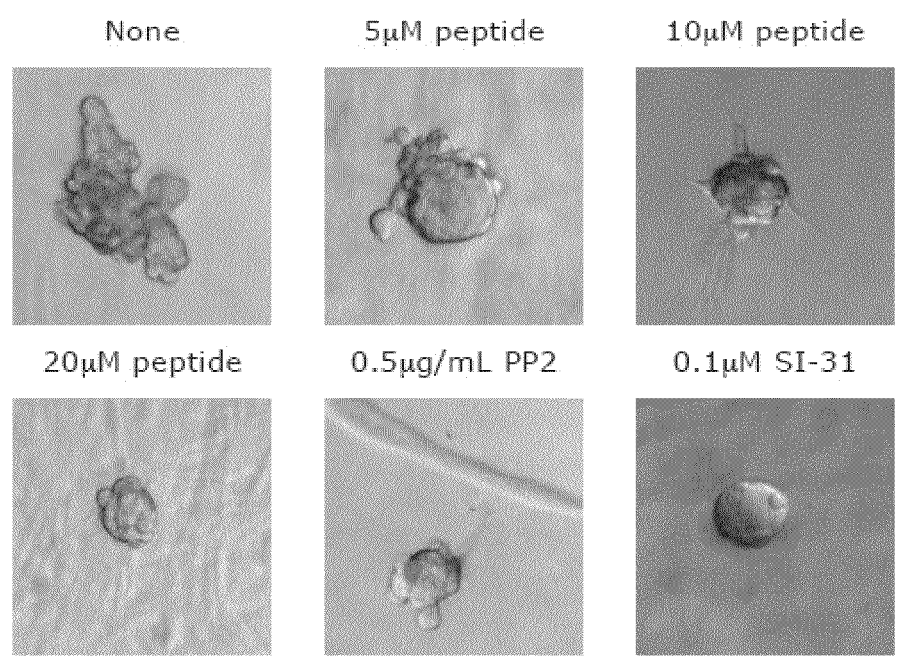
FIG. 8. Reversion of MMTV-induced transformed phenotype of mammary epithelial cells by ITAM peptide. Representative pictures from three-dimensional cultures: MMTV+ Mm5MT tumor cells were incubated on Matrigel® for six days, in the presence or absence of ITAM peptide (5-20 µM) or the Syk inhibitor SI-31 (100 nM). Reversion to round 3D phenotype was readily apparent in cultures treated with 20 µM peptide or SI-31.

The MMTV$^+$ carcinoma line, Mm5MT, expresses high levels of MMTV Env. In 3D cultures, Mm5MT cells form structures that are not round, but rather are branched and lack a hollow lumen. When treated with ITAM peptide, Src or Syk inhibitors, Mm5MT acini exhibited a more round phenotype (FIG. 8). This observation confirms the finding that the effects of ITAM peptide treatment are similar to those of Src or Syk inhibition. The round acini resulting from such treatments did not have a hollow lumen.

Figure 9:
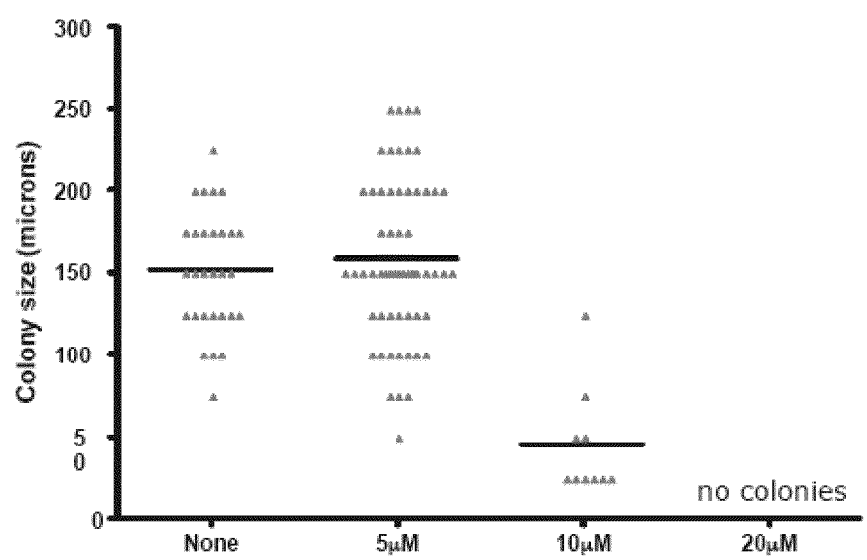
FIG. 9. Reversion of ITAM-induced transformed phenotype of fibroblasts by ITAM peptide. Colony formation assay for NIH3T3 cells transduced with the ITAM-containing chimera, MAHB. Colonies were defined as viable cell clusters greater than 75 µm in size and scored on day 21. ITAM peptide (0-20 µM) was added with the feeding media throughout the experiment and lead to reduction in both size and number of colonies formed.

Lastly, the ability of the ITAM peptide to block colony formation of ITAM-expressing 3T3 fibroblasts was tested (described further in Example 20 below). In this system, soft agar colony growth is independent of integrin signaling, which may itself utilize Syk kinase. As depicted in FIG. 9, chronic treatment of ITAM$^+$ fibroblasts with the ITAM peptide was sufficient to reduce colony formation.

Thus, synthetic peptides of the present invention were validated as inhibitors of ITAM signaling in the transformation of both epithelial and fibroblast cells.

Example 7

Figure 10:
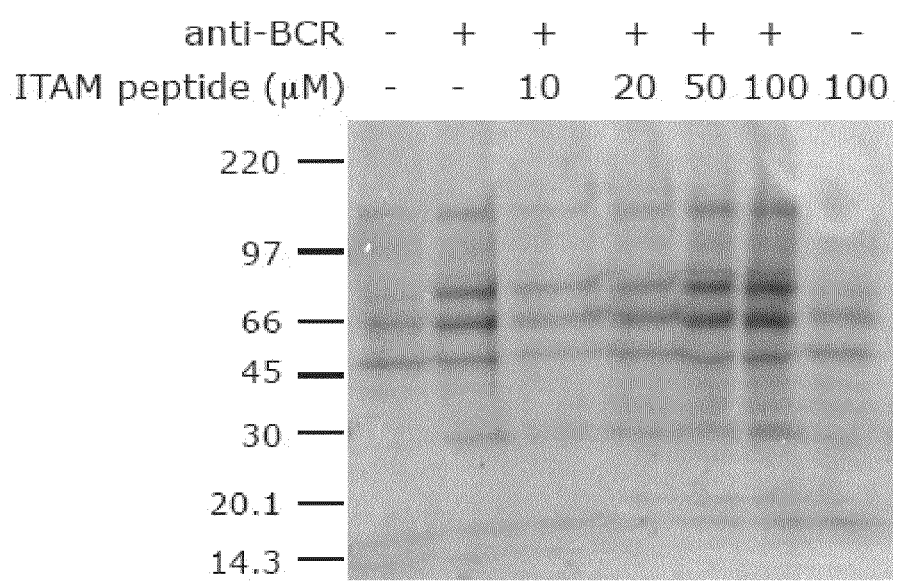
FIG. 10. Effect of ITAM peptide on B lymphocyte stimulation. Proliferation of mouse splenic B cells: Cells were incubated for 48 h in the presence or absence of 20 µM peptide and stimulated with 10 µg/ml anti-BCR antibodies. [$^3$H] Thymidine incorporation was measured in the last 4 h of the experiment Inhibition of the B cell proliferation by the ITAM peptide was highly significant (p=0.0017). Similar stimulations were performed with the non-ITAM containing ligands, LPS (20 µg/ml) and anti-CD40 (5 µg/ml). Concomitant addition of the ITAM peptide had no effect on these stimuli (data not shown). Inhibition of tyrosine phosphorylation was confirmed by Western blotting. Splenic B cells were pre-incubated with 0-100 µM ITAM peptide for 3 h and then stimulated with anti-BCR antibodies as above for further 5 min. Lysates were detected with anti-phospho-tyrosine antibody (data not shown).

Immune Cell Activation is Inhibited by ITAM-Based Peptides of the Present Invention To determine the ability of peptides of the present invention to block activation of B lymphocytes, these cells were treated concomitantly with stimulating anti-BCR antibodies and the ITAM peptide. Peptide treatment resulted in inhibition of BCR-induced proliferation (FIG. 10A). The ITAM peptide had no significant effect on stimulation of B lymphocytes through non-ITAM receptors such as CD40 or LPS (data not shown).

To verify that the ITAM peptide directly inhibited the tyrosine kinase activity associated with ITAM-based BCR signaling, Western blotting for tyrosine phosphorylation was used. When the relevant peptide concentrations were used, this activity was visibly reduced (data not shown). Higher concentrations of the peptide, by contrast, were neither stimulatory nor inhibitory.

Figure 11:
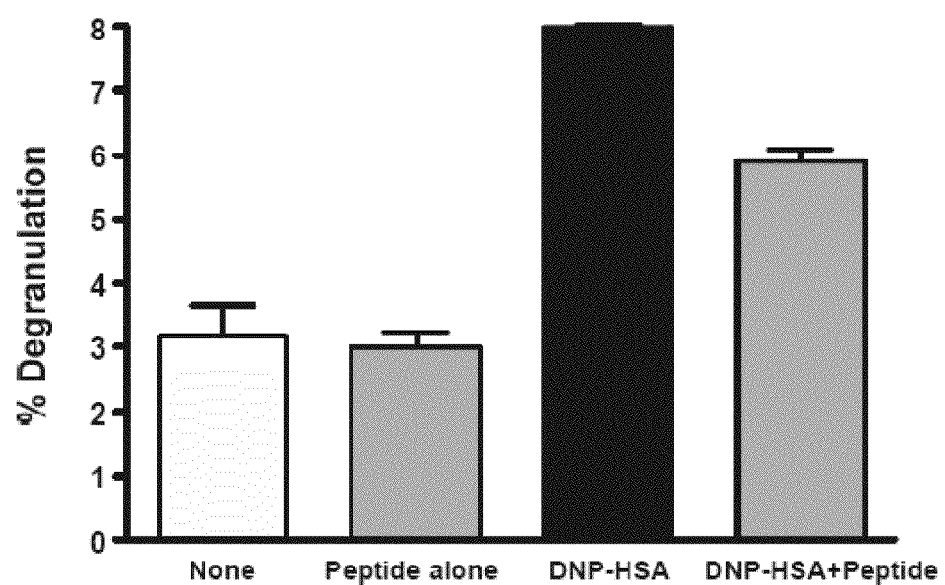
FIG. 11. FcεRI-mediated degranulation of RBL-2H3 cells. The effect of ITAM peptide on mast cell function was evaluated by degranulation induced by FcεRI cross-linking. RBL-2H3 cells were incubated overnight with anti-DNP IgE (1 µg/ml), in the presence or absence of ITAM peptide (25 µM). Subsequently, the cells were cross-linked with DNP-HSA (10 ng/ml) to induce degranulation, as detected by hexosaminidase activity. Degranulation is shown as percent of maximal activity obtained from whole cell lysates. ITAM peptide treatment caused a significant reduction (p=0.093) in FcεRI-induced degranulation.

Next, ability of peptides of the present invention to block degranulation of RBL-2H3 mast cells was tested. The stimulus was, under these conditions, cross-linking by IgE of the ITAM-containing high-affinity Fcε receptor 1. Indeed, this process was also significantly inhibited by the ITAM peptide, although in a higher dose than in other systems (FIG. 11).

These findings verify that the synthetic peptides of the present invention have utility in inhibiting ITAM signaling in the immune system.

Example 8

Modification of Synthetic ITAM Analogues to Improve Potency, specificity, and Pharmacological Properties The synthetic peptides of the previous Examples are modified to improve their potency and specificity for interaction between viral ITAM motifs and cellular proteins that interact therewith, and/or improved pharmacological properties (e.g. solubility, bioavailability, biological half-life). The following principles are applied to the design:

1. The sequence should contain at least one YxxL motif of the ITAM.
2. The sequence and its ends should provide sufficient hydrophilicity to maintain significant water solubility and stability in solution.
3. The sequence should preferably not contain other known motifs The modified peptides are tested as described in the previous Examples, in order to identify peptides with improved properties.

Example 9

Treatment of Breast Cancer using Synthetic ITAM Analogues

The synthetic peptides of the previous Examples are tested in animal models of carcinoma (e.g. breast cancer), and found to reverse the transformation of cells in implanted breast cancer tumors and to shrink the size of the tumors.

Alternatively, the synthetic peptides are tested in animal models of metastatic carcinoma, or ability to prevent metastasis and are found to reduce the incidence of metastasis.

Example 10

Inhibition of Interactions of Cellular Proteins with an EBV LMP2A ITAM using Synthetic ITAM Analogues Water-soluble peptides are designed to block the interaction of cellular proteins with an ITAM motif of Epstein-Barr virus (EBV) LMP2A protein (e.g. RHSDYQPLGTQDQS-LYLGLQHG; SEQ ID No: 50), in accordance with the principles outlined in Examples 5-9. The peptides are tested for ability to block transformation of keratinocytes by LMP2A and treat Burkitt's lymphoma in animal models, in an analogous manner to the previous Examples.

Example 11

Inhibition of Interactions of Cellular Proteins with an KSHV K1 ITAM Using Synthetic ITAM Analogues Water-soluble peptides are designed to block the interaction of cellular proteins with an ITAM motif of KSHV K1 protein (e.g. DSNKTVPQQLQDYYSLHDLCTEDYTQP; SEQ ID No: 51), in accordance with the principles outlined in Examples 5-9. The peptides are tested for ability to block transformation of fibroblasts by K1 and to treat animal models of Kaposi's sarcoma, in an analogous manner to the previous Examples.

Example 12

Inhibition of Interactions of Cellular Proteins with an Hantavirus G1 ITAM using Synthetic ITAM Analogues Water-soluble peptides are designed to block the interaction of cellular proteins with an ITAM motif of hantavirus G1 protein (e.g. KQGCYRTLGVFRYKSRCYVGLVWG, RKGCYRTLGVFRYKSRCYVGLVWG, KRGCYRTLGVFRYKSRCYVGLVWS, QRGCYRTLGVFRYKSRCYVGLVWN, KPGCYRTLGVFRYKSRCYVGLVWG, KKGCYRTLGVFRYKSRCYVGLVWC, KRGCYRTLGVFRYKSRCYVGLVWC, HRGCYRTLGVFRYRSRCYVGLVWG, RKGCYRTLGVFRYKSRCYVGLVWC, GKGCYRTLGVFRYKSRCYVGLVWC, KRGCYRTLSVFRYRSRCFVGLVWC, MQGCYRTLSLFRYRSRFFVGLVWC, KRGLYRTLSMFRYKSKCYVGLVWC, TPGCYRTLNLFRYKSRCYIFTMWI, or GPGCYRTLNLFRYKSRCYELTMWT, SPGCYRTLNLFRYKSRCYIFTVWV, GPGCYRTLNLFRYKSRCYWLTMWL; SEQ ID No: 52-68, respectively), in accordance with the principles outlined in Examples 5-9. The peptides are tested for ability to treat hantavirus pulmonary syndrome in animal models, in an analogous manner to the previous Examples.

Example 13

Inhibition of Interactions of Cellular Proteins with an Fc Receptor Gamma ITAM using Synthetic ITAM Analogues Water-soluble peptides are designed to block the interaction of cellular proteins with an ITAM motif (e.g. AATASEKSDGIYTGLSTRTQETYETLKHE, ETADGGYMTLNPRAPTDDDKNIYLTL, or DYETADGGYMTLNPRAPTDDDKNIYLTL; SEQ ID No: 69-71, respectively) of Fc receptor gamma-chain protein (e.g. FcγRIIa and FcγRIIb), in accordance with the principles outlined in Examples 5-9. The peptides are tested for ability to treat pathological thrombosis, autoimmune hemolytic anemia, and idiopathic thrombocytopenic purpura, in animal models, in an analogous manner to the previous Examples.

Example 14

Inhibition of Interactions of Cellular Proteins with Immune Protein ITAMS using Synthetic ITAM Analogues Water-soluble peptides are designed to block the interaction of cellular proteins with an ITAM motif of TCR-ζ/ηa, TCR-ζ/ηb, TCR-ζc, TCR-ζ/ηc, CD3-γ, CD3-δ, CD3-ε, FcεRI-γ, or FcεRI-β, (e.g. DAGDEYEDENLYEGLNLDDCSMYEDI, DSKAGMEEDHTYEGLDIDQTATYEDIVTL, DAPAYQQGGQNQLYNELNLGRREEYDVL, DAPAYQHGQNPVYNELNVGRREEYAVL, DAPAYQQGQNQLYNELNLGRREEYDVLDKRR, ETAANLQDPNQLYNELNLGRREEYDVL, DVPVSPQGHTQLYNELNIGRREEYDVLDKRR, TAANLQDPNQLYNELNLGRREEYDVLEKK, QQRRRNPQEGVYNALQKDKMAEAYSEIGT, ERPPPVPNPDYEPIRKGQRDLYSGLNQR, DTQALLRNDQVYQPLRDRDDAQYSHLGGN, DKQTLLPNDQLYQPLKDREDDQYSHLQGN, DKQTLLNNDQLYQPLKEREDDQYSHLRKK, EVQALLKNEQLYQPLRDREDTQYSRLGGN, AIASREKADAVYTGLNTRSQETYETLKHE, AAITSYEKSDGVYTGLSTRNQETYETLKHE, or DIASREKSDAVYTGLNTRNQETYETLKHE; SEQ ID No: 72-88, respectively), in accordance with the principles outlined in Examples 5-9. The peptides are tested, in an analogous manner to the previous Examples, for ability to treat animal models of B cell activation disorders, mast cell activation disorders, lymphoma (e.g. Hodgkin's lymphoma or non-Hodgkin's lymphoma), leukemia (e.g. acute lymphocytic leukemia, acute myelogenous leukemia, chronic lymphocytic leukemia, chronic myelogenous leukemia), lymphadenopathy, Kikuchi's disease, Rosai-Dorfman disease, progressive transformation of germinal centers, Castleman's disease (e.g. unicentric or multicentric), lymphomatoid granulomatosis, lymphomatoid papulosis, angioimmunoblastic, or other lymphoproliferative or immune cell-activation diseases.

Example 15

MAHB: A Nonviral, Membrane-Bound, ITAM-Containing Protein Materials and Experimental Methods Examples 15-20

Cell Lines and Retroviral Infection

NMuMG and NIH3T3 cell lines were obtained from the American Type Culture Collection. NMuMG lines were maintained in DMEM containing 10% heat-inactivated FBS, 2 mM L-glutamine, 100 U/ml penicillin-streptomycin, and 10 mg/ml insulin at 37° C. and 10% $CO_2$. All NIH3T3 lines were maintained in DMEM containing 10% heat-inactivated FBS, 2 mM L-glutamine, 100 U/ml penicillin-streptomycin, and 50 mM 2-ME at 37° C. and 10% $CO_2$.

Construction of MAHB and its ITAM-mutant variant and cloning into the MIGR1 retroviral vector is described in Bannish et al (Ligand-independent signaling functions for the B lymphocyte antigen receptor and their role in positive selection during B lymphopoiesis. J Exp Med 2001 Dec. 3; 194 (11):1583-96). Fusion protein constructs were transfected with $CaPO_4$ into the Bosc23 packaging cell line. To generate stable lines expressing each construct, 0.25 $10^6$ NMuMG cells or 0.5 $10^6$ NIH3T3 cells were infected by centrifugation at 200 g for 1.5 h at 25° C. in 4 ml of 1:1 growth medium to retroviral supernatant containing polybrene (4 mg/ml). After infection, cells were grown in medium and sorted 48 h post-transduction to obtain pure GFP-expressing populations.

Flow Cytometry and Immunofluorescence

Analysis of GFP expression (as an indicator of successful retroviral infection and protein expression) was performed by flow cytometry on a FACSCalibur® (BDBiosciences), using wild-type NMuMG cells as a negative control. To determine E-cadherin expression by flow cytometry, 2D cultures of $10^6$ NMuMG cells were used. Rat anti-human E-cadherin (Sigma-Aldrich) was used with goat anti-rat IgG-AlexaFluor-647 (Molecular Probes), where normal rat IgG served as the negative control.

To directly determine expression of MAHB and ITAM-mutant, 2D cultures of NMuMGs in 16-well slides were used. Cell staining was performed using the BDCytofix/Cytoperm kit (BDBiosciences) with a rat monoclonal anti-HA high affinity antibody (clone 3F10, Roche) followed by goat anti-rat IgG-Alexa Fluor-555 antibody (Molecular Probes). Images were captured and analyzed using a X 40 objective on a Zeiss Axiovert 200M inverted epifluorescence microscope equipped with PCO SensiCam QE high-resolution camera and Slidebook® image analysis software (Intelligent Imaging Innovations).

3D Cultures

NMuMG cells ($1 \times 10^4$ cells per chamber) were cultured on recombinant basement membrane (Matrigel®) cushions, without exogenous EGF, and structures were analyzed using the microscope and software. For each independent experiment, 50-200 structures were scored. For inhibitor studies, PP2, Piceatannol, and Syk Inhibitor 31 (Lai et al, 2003, Bioorg Med Chem Lett 13: 3111-3114) (all from EMD) were added on day 3 of culture and scored and imaged on day 6. For apoptosis assays, TNFα (R&DSystems) or TRAIL (BIOMOL Research Laboratories, Inc.) was added on day 8 of culture for 20 h, then cells were stained for cleaved caspase-3. Cell staining was performed with rabbit anti-cleaved caspase-3 (Cell Signaling), rabbit anti-E-cadherin (Sigma-Aldrich), rabbit anti-Vimentin (H-84, Santa Cruz Biotechnology), and anti-rabbit IgG-AlexaFluor-647 (Molecular Probes).

Colony Formation Assays

To assay for anchorage-independent growth, NMuMG cells ($2 \times 10^4$) were suspended in DMEM:F-12 (1:1) medium containing 20% horse serum and 0.8% methocellulose (Sigma-Aldrich). Cells were plated in six-well plates pre-coated with 0.6% agar base in DMEM, were fed with fresh medium every 5 days, and colonies were counted and measured using a graduated reticule at 10× magnification on day 28.

NIH3T3 cells ($1 \times 10^4$) were suspended in 0.3% agar in DMEM containing 10% FBS. Cells from each transduction group were plated in six-well plates pre-coated with 0.6% agar base in DMEM containing 10% FBS, were fed with fresh top agar (0.3% agar in DMEM with 10% FBS) every 5 days, colonies were counted and measured on day 21.

Focus Formation Assays

To assay for contact inhibition, NIH3T3 cells ($4 \times 10^6$) were seeded in a 10 cm dish for 1 week after reaching confluence. Foci were stained with 0.005% crystal violet, and foci in a 4 $cm^2$ area were counted and measured.

Western Blotting and Immunoprecipitation $3 \times 10^6$ NMuMG cells were washed in media without serum and lysed in lysis buffer (1% NP-40, 50 mM Tris pH 7.4, 150 mM NaCl, 5 mM EGTA, 0.5% w/v sodium deoxycholate, 1 mM sodium orthovanadate, protease inhibitor cocktail (Roche), 1 mM phenylmethylsulfonyl fluoride, 0.5% w/v sodium azide) for 15 min on ice. Equivalent amounts of protein were separated by SDS-PAGE and transferred to PVDF. Blots were probed with anti-pTyr (4G10, Upstate), developed with ECL. Location of MAHB and ITAM-mutant was determined by stripping the blots in strip buffer (2% SDS, 62.5 mM Tris, 0.7% β-mercaptoethanol) for 30 min shaking at 62° C. and probing with anti-HA. II antibody (Covance).

For IP-Western experiments, 2D cultures of $15 \times 10^6$ NMuMG cells were treated with 50 μM sodium pervanadate, harvested using cell lifters, and lysed in Phosphosafe® buffer (EMD) supplemented with protease inhibitor cocktail (Roche), 1 mM phenylmethylsulfonyl fluoride, and 0.5% w/v sodium azide for 15 min at room temperature. Equal amounts of protein were pre=cleared with Protein G and incubated with mouse IgG or mouse monoclonal HA antibody (Covance) overnight. Precipitates were collected, washed, separated by SDS-PAGE, and transferred to PVDF membranes. Blots were probed with anti-pTyr (4G10, Upstate), anti-HA.11, and anti-Syk (N-19, Santa Cruz Biotechnology), as described above.

Results

Figure 12C:
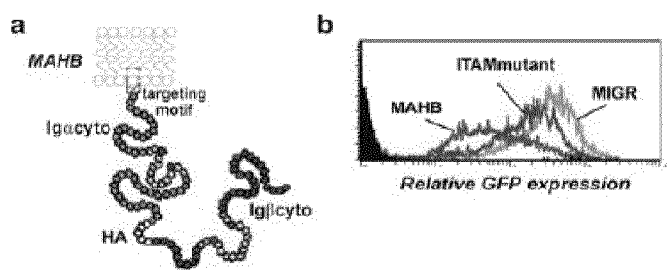
FIG. 12. MAHB: a membrane-bound, nonviral ITAM-containing protein. (a) Illustration of the MAHB fusion protein, which encodes the cytoplasmic domains of Igα and Igβ separated by an HA tag (white). The protein is targeted to the membrane by the myristoylation/palmitoylation sequence of Lck. (b) GFP expression of NMuMG cells transduced with the empty vector (MIGR), MAHB, and ITAM-mutant as assessed by flow cytometry and controlled by nontransduced WT cells. (c) Expression of MAHB and ITAM-mutant in NMuMG cells grown in 2D culture as identified by HA staining in (unmarked, bright areas), with nuclear staining (DAPI; bright areas shaded in diagonal lines). Bar, 50 µm.
Figure 12C:
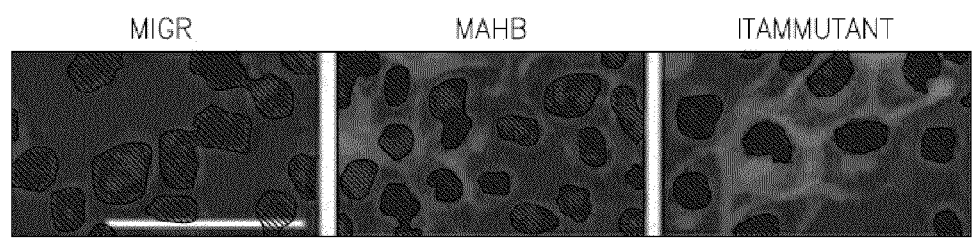

To determine whether transformation is a general consequence of expressing ITAM-containing proteins in non-hematopoietic tissues, a fusion protein termed "MAHB" was created. Instead of encoding a viral ITAM motif, MAHB encodes the cellular ITAMs of Igα and Igβ, which are normally expressed as a heterodimer in B cells, wherein they are non-transforming, and an HA tag. A general feature of cellular ITAM-based receptors is their existence as multi-protein complexes at the cell surface, whose components cannot be transported individually to the cell surface. To circumvent the need to express the entire BCR complex, MAHB was directly targeted to the plasma membrane using the myristoylation/palmitoylation sequence of Lek (FIG. 12A). In addition, a signaling-deficient variant of this protein was generated, ITAM-mutant, in which the ITAM tyrosines were substituted with phenylalanine (equivalent to Y182F, Y193F in Igα and Y195F, Y206F in Igβ). This variant was used to confirm that effects observed following MAHB expression was ITAM dependent. Both the MAHB and ITAM-mutant proteins were cloned into the MIGR1 retroviral vector that expresses a bicistronic mRNA encoding either MAHB or ITAM-mutant and GFP (Pui J C et al, Notch1 expression in early lymphopoiesis influences B versus T lineage determination. Immunity 1999 September; 11(3):299-308). The retroviral transduction efficiency for each construct was about 50%, as indicated by GFP expression. Stable cell lines were then generated by sorting cells expressing high levels of GFP, which comprised approximately 10-15% of the transduced population. Based upon GFP or protein expression, MAHB was expressed at lower levels than ITAM-mutant in both cell types used (FIG. 12B-C). Accordingly, ITAM-mutant and MIGR express higher protein levels and are thus valid negative controls for MAHB. Finally, MAHB and the ITAM-mutant protein expression and membrane localization were confirmed by immuno-staining for the HA-tagged proteins, as depicted in FIG. 12C. Monitoring growth rates and survival of NMuMG cells in 2D cultures revealed no differences between cell populations expressing any of these chimeric proteins.

Example 16

Plasma Membrane Targeted Expression of Igα/Igβ Cytoplasmic Domains Triggers ITAM-Dependent Transformation of Mammary Epithelial Cells To determine whether expression of MAHB was able to transform epithelial cells in vitro, the formation of 3Dacinar structures by mammary epithelial cells (MEC) was monitored. When placed on a recombinant basement membrane (Matrigel®) with the proteins necessary to provide attachment and survival factors, MECs develop into growth-arrested, organized acinar structures, as described in previous Examples. On a scale of zero (normal) to five (most abnormal), acini expressing MAHB, ITAM-mutant, or the empty vector (MIGR) were evaluated based on their shape, size, presence of a lumen, structural integrity, and cellular morphology. For individual structures, one point was given for each of the following abnormalities: being nonspherical, enlarged (diameter over 50 μm), having a malformed (or multiple) lumen(s), branching from the 3D structure, and having abnormal cellular morphology. Examples of acini and their respective scores are depicted in FIG. 13A.

As depicted in FIG. 13B, MAHB-expressing NMuMG cells developed depolarized acini, similar to cells expressing MMTV Env protein (Examples 1-4). By contrast, NMuMG cells transduced with MIGR formed intact polarized acinar structures with a hollow lumen similar to wild-type cells and exhibited an average score very similar to wild-type NMuMG cells. The population of MAHB-expressing acini as a whole were significantly (P<0.0001) more abnormal than those expressing GFP alone. Additionally, the average score of the MAHB-expressing NMuMG acini was consistently higher than those expressing GFP alone or the ITAM-mutant. Moreover, when compared to MIGR and ITAM-mutant-transduced NMuMG cells, MAHB-expressing cells formed fewer normal structures, and each of the individual morphological abnormalities examined occurred with a higher frequency (FIG. 13C). No correlation was found between low and high amounts of MAHB within these sorted populations, as determined by GFP fluorescence, and the degree of acinar depolarization. Acinar structures formed by ITAM-mutant-expressing NMuMG cells were normal, indicating that the depolarization induced by MAHB expression was ITAM dependent (FIG. 13B). This lack of induction of depolarization of 3Dacini by the ITAM-mutant is not due to low protein expression, as the variant was expressed at higher levels than MAHB.

Figure 14:
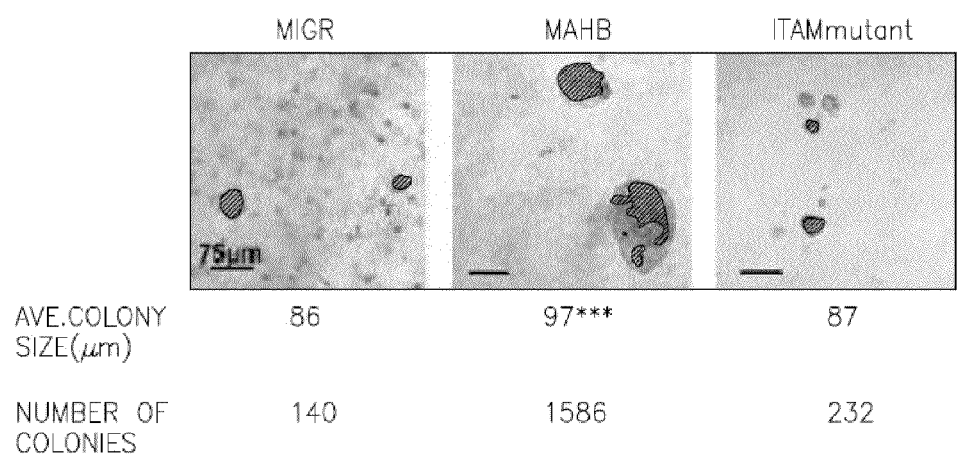
FIG. 14. Expression of MAHB in murine mammary epithelial cells leads to anchorage independence. Colony formation assay for NMuMG cells transduced with the empty vector (MIGR), MAHB, and ITAM-mutant. Colonies were scored on day 28 and defined as viable cell clusters greater than 75 µm in size. Representative bright field images overlaid with GFP to indicate protein expression from one of three independent experiments are shown. The average size and total number of colonies formed by each cell type (out of 1 $10^4$ cells seeded) in a representative experiment are also indicated. ***: P<0.0001 (one-way ANOVA analysis). Bar, 75 µm.

The ability of anchorage-dependent NMuMG lines to form colonies in soft agar-methocellulose cultures was also examined. Inefficient colony formation was observed in MIGR-expressing cells. By contrast, cells expressing MAHB exhibited more colonies (1586 compared to 140) that were significantly larger (97 μm compared to 86 μm, P<0.0001) (FIG. 14). Colony formation was reduced to nearly background (MIGR) levels of both number and size in the ITAM-mutant-expressing NMuMG cells.

Thus, expression of cellular ITAM motifs is sufficient, under the conditions utilized herein, to drive transformation of epithelial cells.

Example 17

ITAM Expression Induces an EMT Phenotype in Mammary Epithelial Cells

Figure 15A:
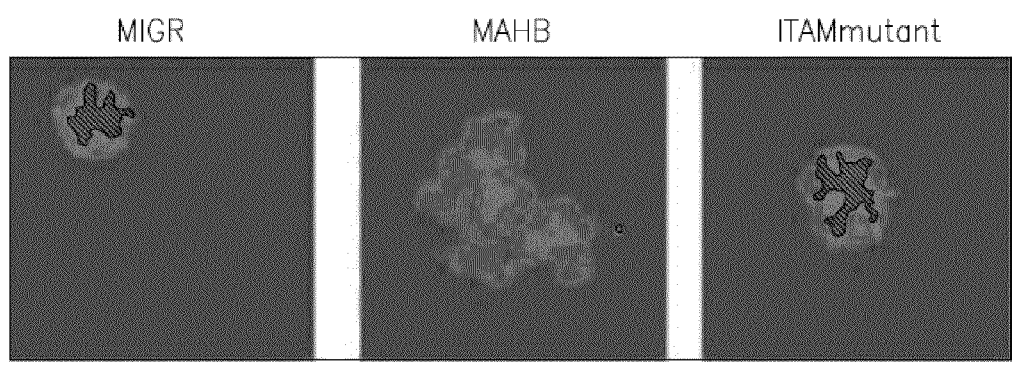
FIG. 15. MAHB expression in murine mammary epithelial cells induces an EMT phenotype. E-cadherin and vimentin expression in NMuMG cells transduced with MIGR, MAHB, and ITAM-mutant. (a) Top, mean fluorescence intensity (MFI) of E-cadherin surface expression as quantified by flow cytometry from 2D cultures. Data from one representative experiment is depicted. Bottom, 3D cultures stained for E-cadherin on day 6. Representative images are depicted with nuclear staining (DAPI; unmarked, bright areas) and E-cadherin (bright areas shaded in diagonal lines). (b) 3D cultures stained for vimentin on day 9. Representative images are depicted with nuclear staining (DAPI; unmarked, bright areas) in blue and vimentin (bright areas shaded in diagonal lines). (a, b) All images are depicted under the same magnification, and all structures are GFP$^+$.
Figure 15B:
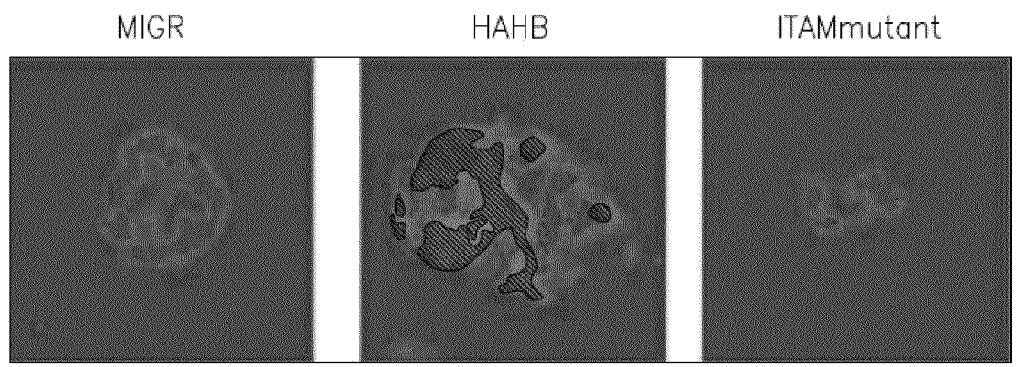

The process of epithelial to mesenchymal transition (EMT; described in Examples 1-4) predicts, in most systems, aggressive metastatic transformation in vivo. A loss of the epithelial marker E-cadherin was observed in NMuMG cells expressing MAHB, but not those expressing ITAM-mutant or transfected with MIGR (FIG. 15A). In addition, NMuMG cells transduced with MAHB gained expression of the mesenchymal marker vimentin, whereas MIGR- and ITAM-mutant-expressing cells did not (FIG. 15B).

These findings show that these cells are undergoing an EMT in response to ITAM expression.

Example 18

Sensitivity of Depolarized MAHB-Expressing Acini to Trail and TNFα

Figure 16:
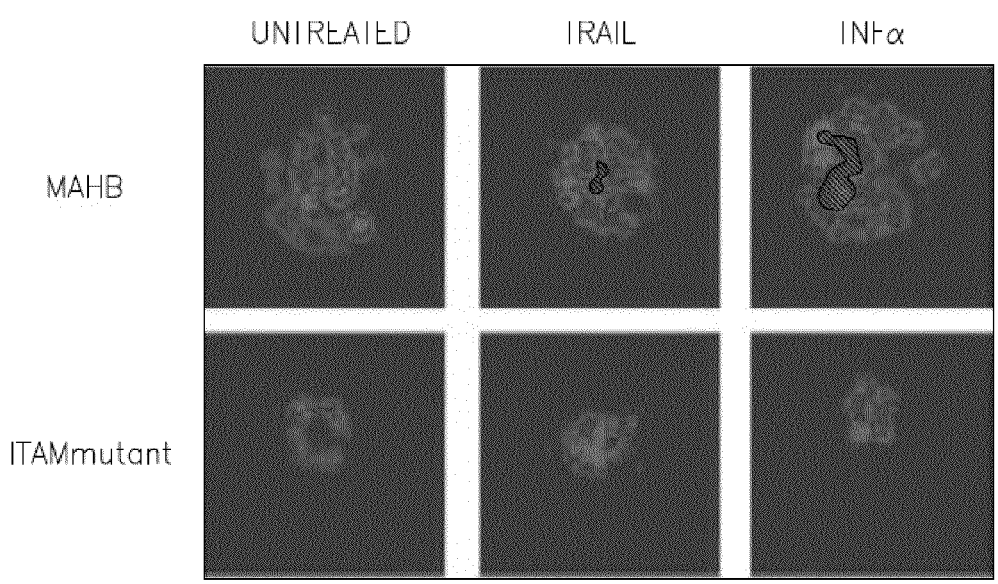
FIG. 16. MAHB-expressing acini become sensitive to TRAIL and TNFα. Sensitivity of MAHB- and ITAM-mutant-expressing NmuMG acini to apoptotic-inducing agents. Acini were treated in 3D cultures on day 8 for 20 h with either 1 mg/ml TRAIL or 100 nM TNFα. Cultures were then stained for activated caspase-3 to assess apoptosis induction. Representative images of the same magnification are depicted with nuclear staining (DAPI; unmarked, bright areas) and activated caspase-3 (bright areas shaded in diagonal lines); all structures are GFP$^+$.

Next, the sensitivity to apoptosis induced by TRAIL and TNFα was determined for NMuMG cells expressing MAHB in 3D cultures. In the presence of exogenous pro-apoptotic stimuli, normal acini are resistant to apoptosis as a consequence of basement membrane-driven polarization. However, acini that have become depolarized following oncogene expression become, under the conditions utilized herein, sensitive to apoptosis induction due to disrupted integrin signaling. Following treatment with TRAIL and TNFα, MAHB-expressing acini exhibited caspase-3-dependent apoptosis, similar to MMTV Env-expressing cells (Example 3), whereas MIGR- and ITAM-mutant-expressing cells did not (FIG. 16).

These findings provide further evidence that expression of a non-viral ITAM-containing protein is capable of transforming epithelial cells.

Example 19

SRC and SYK Tyrosine Kinases Contribute to ITAM-Induced Acinar Depolarization

Figure 17:
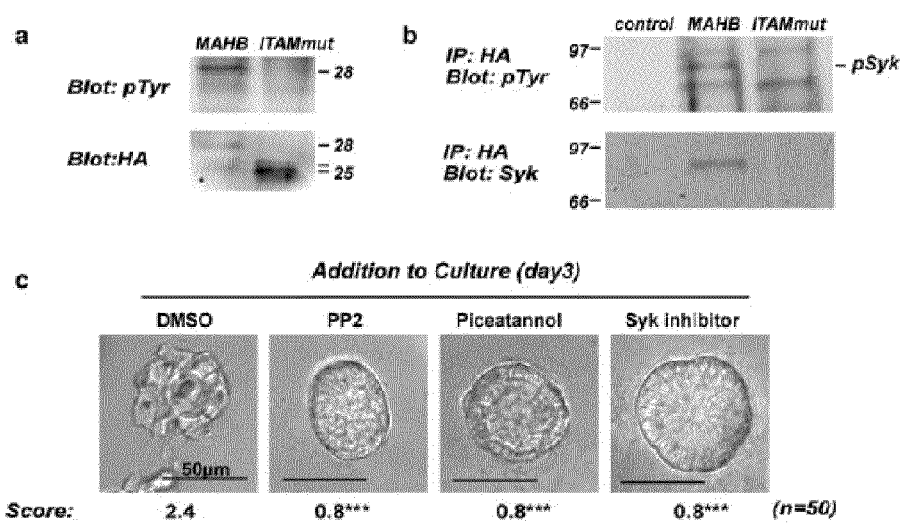
FIG. 17. Involvement of Src and Syk kinases in MAHB-induced transformation. Phosphorylation status of MAHB and association with phosphorylated Syk in 2D cultures of NMuMG cells. (a) Upper panel depicts a representative Western blot of NMuMG whole-cell lysates probed with an anti-phosphotyrosine antibody. Lower panel shows the same blot stripped and re-probed with an HA antibody. (b) HA IP from pervanadate-treated cells (representative of four experiments). Upper panel: Western blot probed with an antibody against phosphotyrosine. Lower panel: the same blot stripped and re-probed with an antibody specific for Syk. Results are representative of four independent experiments. (c) MAHB expressing NMuMG acini were treated in 3D cultures for 3 days with either vehicle (DMSO), PP2 (1 µg/ml), Piceatannol (1 µg/ml), or a specific Syk inhibitor (0.25 µM). Representative bright field images taken on day 6 are depicted; structures are GFP$^+$. Bar, 50 µm. Average score of acinar structures was calculated by scoring 50 acini for each treatment. ***: P<0.0001 (one-way ANOVA analysis).

Under the conditions utilized herein, ITAM signaling requires the activity of Src and Syk family kinases. The phosphorylation status of the chimeric proteins was examined in 2D cultures by anti-phosphotyrosine and anti-HA Western blotting. In MAHB-expressing NMuMG cells, a constitutively tyrosine-phosphorylated band with a molecular weight (MW) of 28 kDa was detected by anti-HA Western blotting, together with two non-phosphorylated bands with a MW of 25 kDa, present at low levels (FIG. 17A). In ITAM-mutant-expressing NMuMG cells, only the two lower MW bands were present.

In order to determine association of the chimeric proteins with Syk, cells were treated with pervanadate, immunoprecipitated with anti-HA antibody, and pellets were probed for Syk. A direct association was observed between phosphorylated (activated) Syk and MAHB, but not ITAM-mutant (FIG. 17B).

Figure 13:
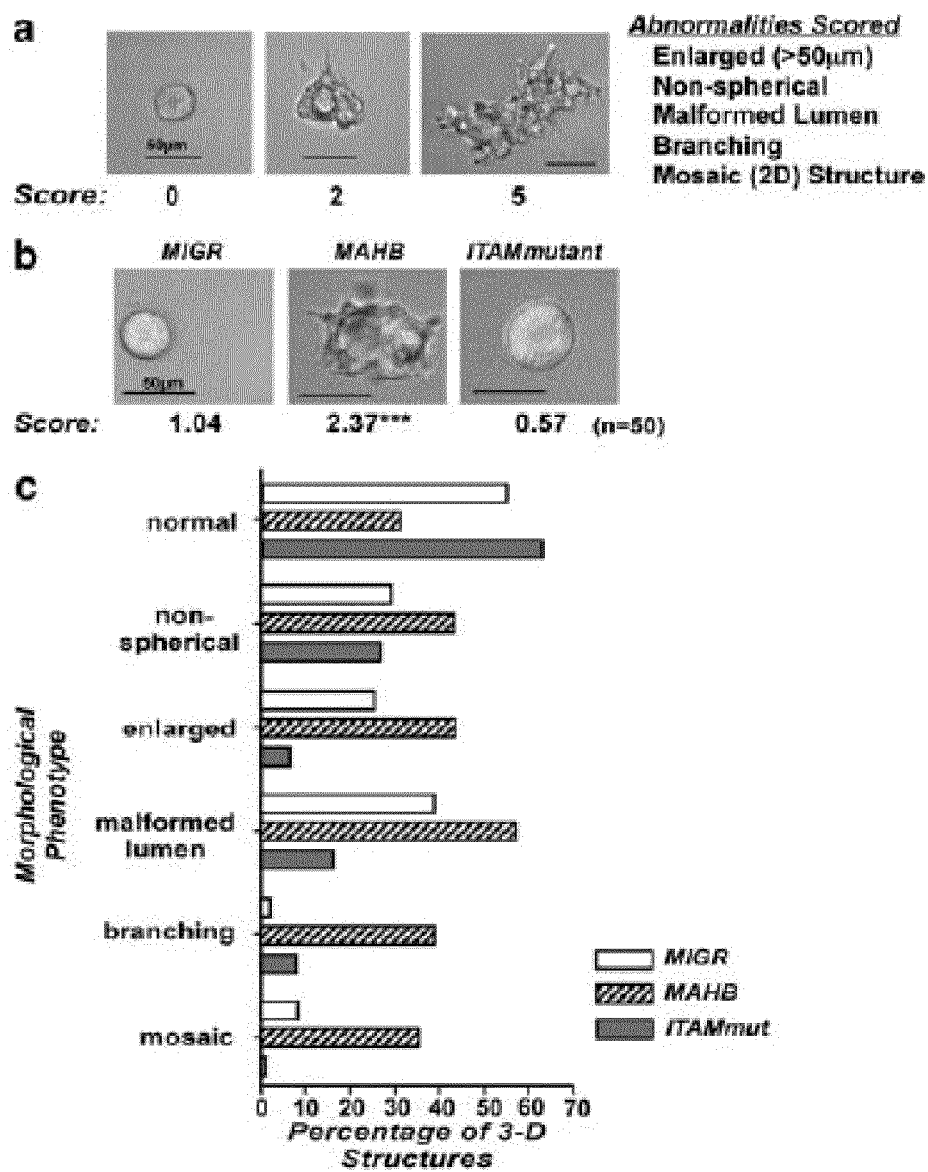
FIG. 13. Expression of a nonviral ITAM-containing protein disrupts 3D acinar architecture of murine mammary epithelial cells. (a) On a scale of zero (normal) to five (most abnormal), acini were scored based on their structure and given one point for each of the abnormalities listed. Depicted are examples of normal and disrupted acini with their corresponding score. Bar, 50 µm. (b) 3D cultures of MIGR, MAHB, and ITAM-mutant-expressing NMuMG cells at day 6 of culture on a Matrigel cushion. Representative acini depicted are GFP$^+$. The average score was calculated by scoring 50 acini from each cell type. ***: P<0.0001 (one-way ANOVA analysis). Bar, 50 µm. (c) The morphological phenotypes of acini scored in (B). The percentage of 3D acini with each morphological characteristic is shown. As acini can have multiple abnormalities, the percentages do not add up to 100%.

To show the dependence on Src and Syk activity of the MAHB-induced transformation of epithelial cells, cells were treated with selective inhibitors of each of these kinases. Inhibition of either Src or Syk prevented the depolarization of acinar structures; instead, normal polarized structures were observed (FIG. 17C). In addition, the average score for MAHB-expressing acini receiving each of the treatments was significantly lower than those receiving vehicle alone, and was equivalent to the baseline score of cells expressing MIGR alone (FIG. 13).

Thus, Src and Syk activity are necessary, under these conditions, for MAHB-induced depolarization of acinar structures, showing that interaction between the cellular ITAM and these proteins mediates transformation of epithelial cells.

Example 20

Expression of an ITAM-Containing Protein causes Transformation of Fibroblasts

Figure 18:
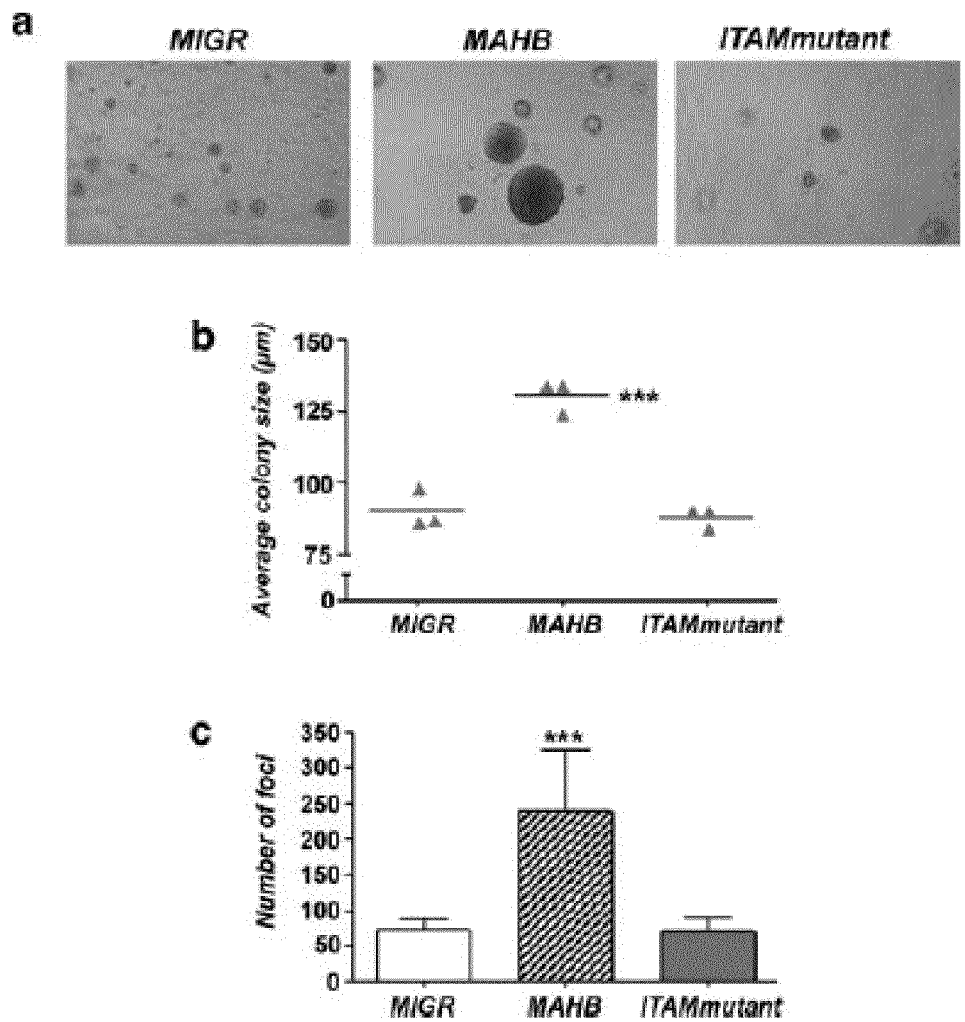
FIG. 18. MAHB transforms murine fibroblasts. (a) Colony formation assay for NIH3T3 cells transduced with the empty vector (MIGR), MAHB, and ITAM-mutant. Colonies were defined as viable cell clusters greater than 75 µm in size and scored on day 21. Representative images from one of three independent experiments. Original magnification, X 10. (b) Average size of colonies formed from each cell type in three independent colony formation assays. Black bar and value represent the mean for the three experiments. ***: P<0.0001 (one-way ANOVA analysis). (c) Focus formation assay with NIH3T3 cells transduced with the empty vector (MIGR), MAHB, and ITAM-mutant. Average number of foci formed in a 4 cm² area from three independent experiments is shown; error bars indicate standard deviation. *: P<0.05 (one-way ANOVA analysis).

To determine whether MAHB expression could transform additional cell types, murine 3T3 fibroblasts were stably transfected with MIGR, MAHB, and ITAM-mutant. To examine the anchorage dependence of the normally adherent NIH3T3 fibroblasts, the transfected cell lines were subjected to a soft agar colony formation assay. NIH3T3 cells transfected with empty vector (MIGR) formed small colonies after 3 weeks (average size 9077 µm), similar to wild-type NIH3T3 cells. Expression of MAHB led to the formation of almost twice as many colonies, that were significantly (P<0.0001) larger than those the empty vector- or ITAM-mutant-transfected cells, indicating a loss of anchorage dependence (13176 µm; FIG. 18A-B). Fibroblasts expressing ITAM-mutant were nearly indistinguishable from cells transfected with MIGR, indicating the importance of these motifs in transformation.

In addition, the fibroblasts were subjected to focus formation assays, another assay of transformation. MAHB-expressing cells formed significantly more foci (approximately threefold; P <0.05) than those transfected with the empty vector or ITAM-mutant vector (FIG. 18C). The foci formed by MAHB-expressing fibroblasts are also larger (average size of 0.715 µm, vs. 0.285 µm for MIGR and 0.290 µm of ITAM-mutant). Thus, the ITAM was required for loss of contact inhibition.

Thus, the ability of ITAM-containing proteins to transform cells is not limited to epithelial cells, but also encompasses other cell types (e.g. connective tissue cells).

Example 21

Testing of Synthetic ITAM Analogues of the Present Invention in a 3-Dimensional Culture Assay To further test the synthetic ITAM analogues of Examples 8-14 and modified variants thereof, epithelial cells transfected with a viral or cellular ITAM-containing protein are cultured on a solubilized basement membrane preparation (e.g. Matrigel®) comprising laminin, collagen (e.g. collagen IV), and optionally heparan sulfate proteoglycans and entactin, in the presence of various peptides in multi-well plates, as described above in Examples 1, 2, 3, 4, 6, 16, and 19. Exogenous EGF is included, or, if desired, omitted. After about 6 days, plates are scanned for wells lacking enlarged structures. The ability to prevent formation of enlarged structures is indicative of ITAM-inhibitory activity. Alternatively, mammary epithelial cells are utilized in this assay, and plates are scanned for wells lacking large spherical structures, or containing ductal structures. Inhibitory peptides are titrated to determine the concentration necessary for inhibition. Untransfected epithelial cells may be used as an internal standard for background levels of enlarged structures.

Alternatively, epithelial cells are cultured in multi-well Invasion Chambers, wherein the bottom chamber contains a chemo-attractant (e.g. a growth factor in high-calcium medium), and plates are scanned for wells wherein reduced numbers of cells cross the membrane, as described above in Example 4.

Example 22

Testing of Synthetic ITAM Analogues of the Present Invention by Colony Formation in AGAR-Methocellulose To further test the synthetic ITAM analogues of Examples 8-14 and modified variants thereof, epithelial cells transfected with a viral or cellular ITAM-containing protein are suspended in the presence of various peptides in multi-well plates in media containing agar, growth factors, and methylcellulose or a substance with similar properties, as described above in Examples 4 and 16. After about three weeks, plates are scanned for wells exhibiting reduced colony size or reduced numbers of colonies over a threshold size. The ability to reduce colony size or number is indicative of ITAM-inhibitory activity. Inhibitory peptides are titrated to determine the concentration necessary for inhibition. Untransfected epithelial cells may be used as an internal standard for background colony formation levels.

Alternatively, connective tissue cells (e.g. fibroblasts) transfected with a viral or cellular ITAM-containing protein are suspended in the presence of various peptides in multi-well plates in media containing agar and growth factors, as described above in Examples 6 and 20. After about three weeks, plates are scanned for wells exhibiting reduced colony size or reduced numbers of colonies over a threshold size. The ability to reduce colony size or number is indicative of ITAM-inhibitory activity. Inhibitory peptides are titrated to determine the concentration necessary for inhibition. Untransfected connective tissue cells may be used as an internal standard for background colony formation levels.

Example 23

Testing of Synthetic ITAM Analogues of the Present Invention by Co-IP of ITAM containing Proteins with Kinases or Substrates Thereof To further test the synthetic ITAM analogues of Examples 8-14 and modified variants thereof, somatic cells (e.g. epithelial cells or connective tissue cells) transfected with a viral or cellular ITAM-containing protein are incubated in the presence of various peptides in multi-well plates, treated with phosphatase inhibitors, lysed, and immunoprecipitated for the ITAM-containing protein under relatively low-stringency detergent conditions. In another embodiment, the phosphate is SHP1. In another embodiment, the phosphate is SHP2. In another embodiment, the phosphate is any other phosphatase having an ITAM motif or protein associated therewith as a substrate. Association of the ITAM-containing protein with a cellular kinase or substrate thereof (e.g. Syk, Src, or a family member thereof) is measured by detecting the presence of the kinase or substrate in the pellet, as described above in Examples 2 and 19. Alternatively, the lysates are immunoprecipitated for the cellular kinase, and the ITAM-containing protein is detected in the pellet. The ability to reduce co-IP is indicative of ITAM-inhibitory activity. Inhibitory peptides are titrated to determine the concentration necessary for inhibition. Untransfected cells may be used as an internal standard for background Co-IP levels.

Example 24

Testing of Synthetic ITAM Analogues of the Present Invention by Detecting Markers of EMT To further test the synthetic ITAM analogues of Examples 8-14 and modified variants thereof, epithelial cells transfected with a viral or cellular ITAM-containing protein are cultured in collagen-containing media in the presence of various peptides in multi-well plates, and levels of a marker of epithelial-mesenchymal transition (e.g. decreased levels of Keratin-18 or E-cadherin expression, or increased levels of vimentin) are detected, as described above in Examples 3 and 17. The ability to prevent or reduce conversion of cells to the transformed phenotype is indicative of ITAM-inhibitory activity. Inhibitory peptides are titrated to determine the concentration necessary for inhibition. Untransfected epithelial cells may be used as an internal standard for background levels of EMT marker levels.

Example 25

Testing of Synthetic ITAM Analogues of the Present Invention by Measuring sensitivity to Apoptosis Induced by Trail or TNF To further test the synthetic ITAM analogues of Examples 8-14 and modified variants thereof, epithelial cells transfected with a viral or cellular ITAM-containing protein are cultured on a solubilized basement membrane preparation (e.g. Matrigel®) comprising laminin, collagen (e.g. collagen IV), and optionally heparan sulfate proteoglycans and entactin, in the presence of various peptides in multi-well plates. On about day 5 of culture, cells are tested for sensitivity to apoptosis induced by TRAIL or TNF, as described above in Examples 3 and 18. The ability to abrogate or reduce sensitivity to apoptosis is indicative of ITAM-inhibitory activity. Inhibitory peptides are titrated to determine the concentration necessary for inhibition. Untransfected epithelial cells may be used as an internal standard for background levels of apoptosis.

Example 26

Testing of Synthetic ITAM Analogues of the Present Invention by Inhibition of B Cell Activation and/or Proliferation To further test the synthetic ITAM analogues of Examples 8-14 and modified variants thereof, B lymphocytes are incubated in the presence of anti-BCR antibodies, in the presence of various peptides in multi-well plates. After about 48 h, activation and/or proliferation of the cells is measured (e.g. by [$^3$H] thymidine incorporation, as described above in Example 7.) The ability to abrogate or reduce activation and/or proliferation is indicative of ITAM-inhibitory activity. Inhibitory peptides are titrated to determine the concentration necessary for inhibition. Untransfected B lymphocytes may be used as an internal standard for background levels of activation or proliferation.

Example 27

Testing of Synthetic ITAM Analogues of the Present Invention by Determining ITAM-Based BCR Signaling To further test the synthetic ITAM analogues of Examples 8-14 and modified variants thereof, B lymphocytes are pre-incubated in multi-well plates in the presence of various peptides, then stimulated with anti-BCR antibodies. After about 5 min, tyrosine phosphorylation of downstream targets is measured (e.g. by Western blotting with anti-phosphotyrosine antibody, as described above in Example 7). The ability to abrogate or reduce tyrosine phosphorylation is indicative of ITAM-inhibitory activity. Inhibitory peptides are titrated to determine the concentration necessary for inhibition. Untransfected B lymphocytes may be used as an internal standard for background levels of tyrosine phosphorylation.

Example 28

Testing of Synthetic ITAM Analogues of the Present Invention by Inhibition of Mast Cell Degranulation To further test the synthetic ITAM analogues of Examples 8-14 and modified variants thereof, mast cells are pre-incubated incubated overnight with anti-DNP IgE, in multi-well plates, then degranulation is induced with DNP-HSA in the presence of various peptides, and degranulation is measured (e.g. by hexosaminidase activity as described above in Example 7). The ability to abrogate or reduce degranulation is indicative of ITAM-inhibitory activity. Inhibitory peptides are titrated to determine the concentration necessary for inhibition. Untransfected mast cells may be used as an internal standard for background levels of degranulation.

Example 29

Testing of Synthetic ITAM Analogues of the Present Invention by Inhibition of Phosphorylation of an ITAM-Containing Protein To further test the synthetic ITAM analogues of Examples 8-14 and modified variants thereof, somatic cells (e.g. epithelial cells or connective tissue cells) are cultured in multi-well plates in the presence of various peptides, then the phosphorylation of a viral or cellular ITAM-containing protein is measured (e.g. by Western blotting as described above in Example 19). The ability to abrogate or reduce phosphorylation is indicative of ITAM-inhibitory activity. Inhibitory peptides are titrated to determine the concentration necessary for inhibition. Untransfected cells may be used as an internal standard for background levels of phosphorylation.

Example 30

Testing of Synthetic ITAM Analogues of the Present Invention by Focus Formation assay To further test the synthetic ITAM analogues of Examples 8-14 and modified variants thereof, connective tissue cells (e.g. fibroblasts) are cultured in multi-well plates in the presence of various peptides, then focus formation assays as performed (e.g. as described above in Example 20). The ability to abrogate or reduce focus formation is indicative of ITAM-inhibitory activity. Inhibitory peptides are titrated to determine the concentration necessary for inhibition. Untransfected cells may be used as an internal standard for background levels of focus formation.

Example 31

Treatment of Sarcoma using Synthetic ITAM Analogues

The synthetic peptides of the previous Examples are tested in animal models of sarcoma (in one embodiment, Kaposi's sarcoma) and are found to reverse the transformation of the sarcoma cells and to shrink the size of the tumors.

Alternatively, the synthetic peptides are tested in animal models of metastatic sarcoma, or ability to prevent metastasis and are found to reduce the incidence of metastasis.

What is claimed is:

1. A method of inhibiting metastasis of a virally-induced cancer containing proteins with immunoreceptor tyrosine based activation motifs (ITAM) or a cancer containing proteins with immunoreceptor tyrosine based activation motifs (ITAM) in a subject, comprising administering to said subject a compound that inhibits an interaction of a first protein and an immunoreceptor tyrosine-based activation motif (ITAM) of a second protein, wherein said compound comprises a peptide containing a sequence selected from the group consisting of SEQ ID NOs: 1-5, 28, 33-35 and 39.

2. The method of claim 1, whereby the peptide is modified via hydroxylation, amidation, esterification, formylation, gamma-carboxyglutamic acid hydroxylation, methylation, phosphorylation, sulfation, glycosylation, reduction, oxidation, disulfide modification, introduction of a thioether bond, introduction of a thiolester bond, a backbone condensation, biotinylation or a combination thereof.

3. The method of claim 1, whereby the peptide comprises an amino acid which is a D amino acid; pyrrolidone carboxylic acid; 2-aminoadipic acid; 3-aminoadipic acid; beta-alanine; beta-aminoproprionic acid; 2-aminobutyric acid; 4-aminobutyric acid; piperidinic acid; 6-aminocaproic acid; 6-aminoheptanoic acid; 2-aminoheptanoic acid; 2-aminoisobutyric acid; 3-aminoisobutyric acid; 2-aminopimelic acid; 2,4 diaminobutyric acid; desmosine; 2,2 diaminopimelic acid; 2,3 diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine; sarcosine; methylisoleucine; methyllysine; methylvaline; norvaline; norleucine; 6-aminohexanoic acid; citrulline; cysteic acid; cyclohexylalanine; alpha-amino isobutyric acid; t-butylglycine; t-butylalanine; phenylglycine; an N-alpha-methyl amino acid, a C-alpha-methyl amino acid, a beta-methyl amino acid, orthinine, or a combination thereof.

4. The method of claim 1, whereby the second protein is a viral protein.

5. The method of claim 1, whereby the metastatic virally induced cancer is a sarcoma.

6. A method of treating B cell proliferative disorder, or a mast cell activation disorder is a subject, comprising administering to said subject a compound that inhibits an interaction of a first protein and an immunoreceptor tyrosine-based activation motif (ITAM) of a second protein, wherein said compound comprises a peptide containing a sequence selected from the group consisting of SEQ ID NOs: 1-5, 28, 33-35 and 39.

7. The method of claim 6, whereby the peptide is modified via hydroxylation, amidation, esterification, formylation, gamma-carboxyglutamic acid hydroxylation, methylation, phosphorylation, sulfation, glycosylation, reduction, oxidation, disulfide modification, introduction of a thioether bond, introduction of a thiolester bond, a backbone condensation, biotinylation or a combination thereof.

8. The method of claim 6, whereby the peptide comprises an amino acid which is a D amino acid; pyrrolidone carboxylic acid; 2-aminoadipic acid; 3-aminoadipic acid; beta-alanine; beta-aminoproprionic acid; 2-aminobutyric acid; 4-aminobutyric acid; piperidinic acid; 6-aminocaproic acid; 6-aminoheptanoic acid; 2-aminoheptanoic acid; 2-aminoisobutyric acid; 3-aminoisobutyric acid; 2-aminopimelic acid; 2,4 diaminobutyric acid; desmosine; 2,2 diaminopimelic acid; 2,3 diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine; sarcosine; methylisoleucine; methyllysine; methylvaline; norvaline; norleucine; 6-aminohexanoic acid; citrulline; cysteic acid; cyclohexylalanine; alpha-amino isobutyric acid; t-butylglycine; t-butylalanine; phenylglycine; an N-alpha-methyl amino acid, a C-alpha-methyl amino acid, a beta-methyl amino acid, orthinine, or a combination thereof.

9. The method of claim 6, whereby the second protein is a viral protein.

10. The method of claim 1, wherein said compound consists of a peptide selected from the group consisting of SEQ ID No: 1-5, 28, 33-35 and 39.

11. The method of claim 6, wherein said compound consists of a peptide selected from the group consisting of SEQ ID No: 1-5, 28, 33-35 and 39.

* * * * *

SEQUENCE LISTING

<160> NUMBER OF SEQ ID NOS: 99

<210> SEQ ID NO 1
<211> LENGTH: 24
<212> TYPE: PRT
<213> ORGANISM: Mouse mammary tumor virus

<400> SEQUENCE: 1

Pro Ala Tyr Asp Tyr Ala Ala Ile Ile Val Lys Arg Pro Pro Tyr Val
1               5                   10                  15

Leu Leu Pro Val Asp Ile Gly Asp
            20

<210> SEQ ID NO 2
<211> LENGTH: 8
<212> TYPE: PRT
<213> ORGANISM: Mouse mammary tumor virus
<220> FEATURE:
<221> NAME/KEY: ACT_SITE
<222> LOCATION: (1)..(1)

<400> SEQUENCE: 2

Lys Arg Pro Pro Tyr Val Leu Leu
1               5

<210> SEQ ID NO 3
<211> LENGTH: 26
<212> TYPE: PRT
<213> ORGANISM: Artificial
<220> FEATURE:
<223> OTHER INFORMATION: chemically synthesized
<220> FEATURE:
<221> NAME/KEY: D/E
<222> LOCATION: (1)..(1)
<223> OTHER INFORMATION: "Xaa" can be either aspartate or glutamate
<220> FEATURE:
<221> NAME/KEY: X
<222> LOCATION: (2)..(8)
<223> OTHER INFORMATION: "X" can be either any naturally occurring amino
      acid
<220> FEATURE:
<221> NAME/KEY: X
<222> LOCATION: (9)..(9)
<223> OTHER INFORMATION: "Xaa" can be either any naturally occurring
      amino acid
<220> FEATURE:
<221> NAME/KEY: X
<222> LOCATION: (10)..(11)
<223> OTHER INFORMATION: "X" can be either any naturally occurring amino
      acid
<220> FEATURE:
<221> NAME/KEY: X
<222> LOCATION: (13)..(14)
<223> OTHER INFORMATION: "X" can be either any naturally occurring amino
      acid
<220> FEATURE:
<221> NAME/KEY: X
<222> LOCATION: (16)..(22)
<223> OTHER INFORMATION: "X" can be either any naturally occurring amino
      acid
<220> FEATURE:
<221> NAME/KEY: X
<222> LOCATION: (24)..(25)
<223> OTHER INFORMATION: "X" can be either any naturally occurring amino
      acid
<220> FEATURE:
<221> NAME/KEY: D/E
<222> LOCATION: (26)..(26)
<223> OTHER INFORMATION: "Xaa" can be either aspartate or glutamate

<400> SEQUENCE: 3

Xaa Xaa Xaa Xaa Xaa Xaa Xaa Xaa Xaa Xaa Xaa Tyr Xaa Xaa Leu Xaa

```
                1               5                    10                   15
Xaa Xaa Xaa Xaa Xaa Xaa Tyr Xaa Xaa Glx
                       20                   25

<210> SEQ ID NO 4
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: D/E
<222> LOCATION: (1)..(1)
<223> OTHER INFORMATION: "Xaa" may be aspartate or glutamate
<220> FEATURE:
<221> NAME/KEY: misc_feature
<222> LOCATION: (2)..(9)
<223> OTHER INFORMATION: Xaa can be any naturally occurring amino acid
<220> FEATURE:
<221> NAME/KEY: D/E
<222> LOCATION: (10)..(10)
<223> OTHER INFORMATION: "Xaa" may be aspartate or glutamate
<220> FEATURE:
<221> NAME/KEY: X
<222> LOCATION: (11)..(12)
<223> OTHER INFORMATION: "Xaa" may be any naturally occurring amino acid
<220> FEATURE:
<221> NAME/KEY: X
<222> LOCATION: (14)..(15)
<223> OTHER INFORMATION: "Xaa" may be any naturally occurring amino acid
<220> FEATURE:
<221> NAME/KEY: X
<222> LOCATION: (17)..(28)
<223> OTHER INFORMATION: "Xaa" may be any naturally occurring amino acid
<220> FEATURE:
<221> NAME/KEY: X
<222> LOCATION: (30)..(31)
<223> OTHER INFORMATION: "Xaa" may be any naturally occurring amino acid
<220> FEATURE:
<221> NAME/KEY: I/L
<222> LOCATION: (32)..(32)
<223> OTHER INFORMATION: "Xaa" can be leucine or isoleucine

<400> SEQUENCE: 4

Xaa Xaa Xaa Xaa Xaa Xaa Xaa Xaa Xaa Xaa Xaa Xaa Tyr Xaa Xaa Leu
1               5                   10                  15

Xaa Xaa Xaa Xaa Xaa Xaa Xaa Xaa Xaa Xaa Xaa Tyr Xaa Xaa Xaa
                20                  25                  30

<210> SEQ ID NO 5
<211> LENGTH: 27
<212> TYPE: PRT
<213> ORGANISM: Artificial
<220> FEATURE:
<223> OTHER INFORMATION: chemically synthesized
<220> FEATURE:
<221> NAME/KEY: D/E
<222> LOCATION: (1)..(1)
<223> OTHER INFORMATION: Xaa can be aspartate or glutamate
<220> FEATURE:
<221> NAME/KEY: variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: Xaa can be aspartate or glutamate
<220> FEATURE:
<221> NAME/KEY: misc_feature
<222> LOCATION: (11)..(12)
```

```
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: I/L
<222> LOCATION: (27)..(27)
<223> OTHER INFORMATION: "Xaa" can be leucine or isoleucine

<400> SEQUENCE: 5

Xaa Xaa Xaa Xaa Xaa Xaa Xaa Xaa Xaa Xaa Xaa Xaa Tyr Xaa Xaa Leu
1               5                   10                  15

Xaa Xaa Xaa Xaa Xaa Xaa Xaa Tyr Xaa Xaa Xaa
            20                  25

<210> SEQ ID NO 6
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: I/L
<222> LOCATION: (32)..(32)
<223> OTHER INFORMATION: "Xaa" can be leucine or isoleucine

<400> SEQUENCE: 6

Xaa Xaa Xaa Xaa Xaa Xaa Xaa Xaa Xaa Xaa Xaa Xaa Tyr Xaa Xaa Leu
1               5                   10                  15

Xaa Xaa Xaa Xaa Xaa Xaa Xaa Xaa Xaa Xaa Xaa Xaa Tyr Xaa Xaa Xaa
            20                  25                  30
```

-continued

```
<210> SEQ ID NO 7
<211> LENGTH: 31
<212> TYPE: PRT
<213> ORGANISM: Artificial
<220> FEATURE:
<223> OTHER INFORMATION: chemically synthesized
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: D/E
<222> LOCATION: (9)..(9)
<223> OTHER INFORMATION: "Xaa" can be aspartate or glutamate
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: Variablelength
<222> LOCATION: (16)..(27)
<223> OTHER INFORMATION: 0-5 residues may not be present
<220> FEATURE:
<221> NAME/KEY: X
<222> LOCATION: (16)..(27)
<223> OTHER INFORMATION: Xaa may be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: I/L
<222> LOCATION: (31)..(31)
<223> OTHER INFORMATION: "Xaa" can be leucine or isoleucine

<400> SEQUENCE: 7

Xaa Xaa Xaa Xaa Xaa Xaa Xaa Xaa Xaa Xaa Xaa Tyr Xaa Xaa Leu Xaa
1               5                   10                  15

Xaa Xaa Xaa Xaa Xaa Xaa Xaa Xaa Xaa Xaa Xaa Tyr Xaa Xaa Xaa
            20                  25                  30

<210> SEQ ID NO 8
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: misc_feature
<222> LOCATION: (2)..(9)
<223> OTHER INFORMATION: Xaa can be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
```

```
<221> NAME/KEY: Variablelength
<222> LOCATION: (17)..(28)
<223> OTHER INFORMATION: 0-5 residues may not be present
<220> FEATURE:
<221> NAME/KEY: X
<222> LOCATION: (17)..(28)
<223> OTHER INFORMATION: Xaa may be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: I/L
<222> LOCATION: (32)..(32)
<223> OTHER INFORMATION: "Xaa" can be leucine or isoleucine

<400> SEQUENCE: 8

Xaa Xaa Xaa Xaa Xaa Xaa Xaa Xaa Xaa Xaa Xaa Xaa Tyr Xaa Xaa Leu
1               5                   10                  15

Xaa Xaa Xaa Xaa Xaa Xaa Xaa Xaa Xaa Xaa Xaa Tyr Xaa Xaa Xaa
            20                  25                  30

<210> SEQ ID NO 9
<211> LENGTH: 16
<212> TYPE: PRT
<213> ORGANISM: Artificial
<220> FEATURE:
<223> OTHER INFORMATION: chemically synthesized
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: I/L
<222> LOCATION: (4)..(4)
<223> OTHER INFORMATION: "Xaa" can be leucine or isoleucine
<220> FEATURE:
<221> NAME/KEY: Variablelength
<222> LOCATION: (5)..(12)
<223> OTHER INFORMATION: 0-2 residues may not be present
<220> FEATURE:
<221> NAME/KEY: X
<222> LOCATION: (5)..(12)
<223> OTHER INFORMATION: Xaa may be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: I/L
<222> LOCATION: (16)..(16)
<223> OTHER INFORMATION: "Xaa" can be leucine or isoleucine

<400> SEQUENCE: 9

Tyr Xaa Xaa Xaa Xaa Xaa Xaa Xaa Xaa Xaa Xaa Tyr Xaa Xaa Xaa Xaa
1               5                   10                  15

<210> SEQ ID NO 10
<211> LENGTH: 19
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(3)
<223> OTHER INFORMATION: 0-2 residues may not be present
<220> FEATURE:
<221> NAME/KEY: X
<222> LOCATION: (2)..(3)
```

```
<223> OTHER INFORMATION: Xaa may be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: I/L
<222> LOCATION: (7)..(7)
<223> OTHER INFORMATION: "Xaa" can be leucine or isoleucine
<220> FEATURE:
<221> NAME/KEY: Variablelength
<222> LOCATION: (8)..(15)
<223> OTHER INFORMATION: 0-2 residues may not be present
<220> FEATURE:
<221> NAME/KEY: X
<222> LOCATION: (8)..(15)
<223> OTHER INFORMATION: Xaa may be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: I/L
<222> LOCATION: (19)..(19)
<223> OTHER INFORMATION: "Xaa" can be leucine or isoleucine

<400> SEQUENCE: 10

Xaa Xaa Xaa Tyr Xaa Xaa Xaa Xaa Xaa Xaa Xaa Xaa Xaa Xaa Xaa Tyr
1               5                   10                  15

Xaa Xaa Xaa

<210> SEQ ID NO 11
<211> LENGTH: 4
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: I/L
<222> LOCATION: (4)..(4)
<223> OTHER INFORMATION: "Xaa" can be leucine or isoleucine

<400> SEQUENCE: 11

Tyr Xaa Xaa Xaa
1

<210> SEQ ID NO 12
<211> LENGTH: 19
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(3)
<223> OTHER INFORMATION: 0-2 residues may not be present
<220> FEATURE:
<221> NAME/KEY: X
<222> LOCATION: (2)..(3)
<223> OTHER INFORMATION: Xaa may be any naturally occurring amino acid
<220> FEATURE:
<221> NAME/KEY: Variablelength
<222> LOCATION: (8)..(15)
<223> OTHER INFORMATION: 0-2 residues may not be present
<220> FEATURE:
<221> NAME/KEY: X
```

```
<222> LOCATION: (8)..(15)
<223> OTHER INFORMATION: Xaa may be any naturally occurring amino acid

<400> SEQUENCE: 12

Xaa Xaa Xaa Tyr Ala Ala Ile Xaa Xaa Xaa Xaa Xaa Xaa Xaa Xaa Tyr
1               5                   10                  15

Val Leu Leu

<210> SEQ ID NO 13
<211> LENGTH: 17
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (6)..(13)
<223> OTHER INFORMATION: 0-2 residues may not be present
<220> FEATURE:
<221> NAME/KEY: X
<222> LOCATION: (6)..(13)
<223> OTHER INFORMATION: Xaa may be any naturally occurring amino acid

<400> SEQUENCE: 13

Xaa Tyr Ala Ala Ile Xaa Xaa Xaa Xaa Xaa Xaa Xaa Xaa Tyr Val Leu
1               5                   10                  15

Leu

<210> SEQ ID NO 14
<211> LENGTH: 17
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(3)
<223> OTHER INFORMATION: 0-2 residues may not be present
<220> FEATURE:
<221> NAME/KEY: X
<222> LOCATION: (2)..(3)
<223> OTHER INFORMATION: Xaa may be any naturally occurring amino acid
<220> FEATURE:
<221> NAME/KEY: misc_feature
<222> LOCATION: (8)..(13)
<223> OTHER INFORMATION: Xaa can be any naturally occurring amino acid

<400> SEQUENCE: 14

Xaa Xaa Xaa Tyr Ala Ala Ile Xaa Xaa Xaa Xaa Xaa Xaa Tyr Val Leu
1               5                   10                  15

Leu

<210> SEQ ID NO 15
<211> LENGTH: 15
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
```

```
<220> FEATURE:
<221> NAME/KEY: misc_feature
<222> LOCATION: (6)..(11)
<223> OTHER INFORMATION: Xaa can be any naturally occurring amino acid

<400> SEQUENCE: 15

Xaa Tyr Ala Ala Ile Xaa Xaa Xaa Xaa Xaa Xaa Tyr Val Leu Leu
1               5                   10                  15

<210> SEQ ID NO 16
<211> LENGTH: 28
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: Variablelength
<222> LOCATION: (11)..(12)
<223> OTHER INFORMATION: 0-2 residues may not be present
<220> FEATURE:
<221> NAME/KEY: X
<222> LOCATION: (11)..(12)
<223> OTHER INFORMATION: Xaa may be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: I/L
<222> LOCATION: (16)..(16)
<223> OTHER INFORMATION: "Xaa" can be leucine or isoleucine
<220> FEATURE:
<221> NAME/KEY: Variablelength
<222> LOCATION: (17)..(24)
<223> OTHER INFORMATION: 0-2 residues may not be present
<220> FEATURE:
<221> NAME/KEY: X
<222> LOCATION: (17)..(24)
<223> OTHER INFORMATION: Xaa may be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: I/L
<222> LOCATION: (28)..(28)
<223> OTHER INFORMATION: "Xaa" can be leucine or isoleucine

<400> SEQUENCE: 16

Xaa Xaa Xaa Xaa Xaa Xaa Xaa Xaa Xaa Xaa Xaa Xaa Tyr Xaa Xaa Xaa
1               5                   10                  15

Xaa Xaa Xaa Xaa Xaa Xaa Xaa Xaa Tyr Xaa Xaa Xaa
            20                  25

<210> SEQ ID NO 17
<211> LENGTH: 28
<212> TYPE: PRT
<213> ORGANISM: Artificial
```

```
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: Variablelength
<222> LOCATION: (11)..(12)
<223> OTHER INFORMATION: 0-2 residues may not be present
<220> FEATURE:
<221> NAME/KEY: X
<222> LOCATION: (11)..(12)
<223> OTHER INFORMATION: Xaa may be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: Variablelength
<222> LOCATION: (17)..(24)
<223> OTHER INFORMATION: 0-2 residues may not be present
<220> FEATURE:
<221> NAME/KEY: X
<222> LOCATION: (17)..(24)
<223> OTHER INFORMATION: Xaa may be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: I/L
<222> LOCATION: (28)..(28)
<223> OTHER INFORMATION: "Xaa" can be leucine or isoleucine

<400> SEQUENCE: 17

Xaa Xaa Xaa Xaa Xaa Xaa Xaa Xaa Xaa Xaa Xaa Xaa Tyr Xaa Xaa Leu
1               5                   10                  15

Xaa Xaa Xaa Xaa Xaa Xaa Xaa Xaa Tyr Xaa Xaa Xaa
            20                  25

<210> SEQ ID NO 18
<211> LENGTH: 26
<212> TYPE: PRT
<213> ORGANISM: Mus musculus

<400> SEQUENCE: 18

Asp Met Pro Asp Asp Tyr Glu Asp Glu Asn Leu Tyr Glu Gly Leu Asn
1               5                   10                  15

Leu Asp Asp Cys Ser Met Tyr Glu Asp Ile
            20                  25

<210> SEQ ID NO 19
<211> LENGTH: 28
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
```

```
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: Variablelength
<222> LOCATION: (11)..(12)
<223> OTHER INFORMATION: 0-2 residues may not be present
<220> FEATURE:
<221> NAME/KEY: X
<222> LOCATION: (11)..(12)
<223> OTHER INFORMATION: Xaa may be any naturally occurring amino acid
<220> FEATURE:
<221> NAME/KEY: Variablelength
<222> LOCATION: (17)..(24)
<223> OTHER INFORMATION: 0-2 residues may not be present
<220> FEATURE:
<221> NAME/KEY: X
<222> LOCATION: (17)..(24)
<223> OTHER INFORMATION: Xaa may be any naturally occurring amino acid

<400> SEQUENCE: 19

Xaa Xaa Xaa Xaa Xaa Xaa Xaa Xaa Xaa Xaa Xaa Xaa Tyr Glu Gly Leu
1               5                   10                  15

Xaa Xaa Xaa Xaa Xaa Xaa Xaa Xaa Tyr Glu Asp Ile
            20                  25

<210> SEQ ID NO 20
<211> LENGTH: 27
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: D/E
<222> LOCATION: (9)..(9)
<223> OTHER INFORMATION: "Xaa" can be aspartate or glutamate
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: Variablelength
<222> LOCATION: (16)..(23)
<223> OTHER INFORMATION: 0-2 residues may not be present
<220> FEATURE:
<221> NAME/KEY: X
<222> LOCATION: (16)..(23)
<223> OTHER INFORMATION: Xaa may be any naturally occurring amino acid

<400> SEQUENCE: 20

Xaa Xaa Xaa Xaa Xaa Xaa Xaa Xaa Xaa Xaa Xaa Tyr Glu Gly Leu Xaa
1               5                   10                  15

Xaa Xaa Xaa Xaa Xaa Xaa Xaa Tyr Glu Asp Ile
            20                  25
```

```
<210> SEQ ID NO 21
<211> LENGTH: 27
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: Variablelength
<222> LOCATION: (11)..(12)
<223> OTHER INFORMATION: 0-2 residues may not be present
<220> FEATURE:
<221> NAME/KEY: X
<222> LOCATION: (11)..(12)
<223> OTHER INFORMATION: Xaa may be any naturally occurring amino acid
<220> FEATURE:
<221> NAME/KEY: misc_feature
<222> LOCATION: (17)..(23)
<223> OTHER INFORMATION: Xaa can be any naturally occurring amino acid

<400> SEQUENCE: 21

Xaa Xaa Xaa Xaa Xaa Xaa Xaa Xaa Xaa Xaa Xaa Xaa Tyr Glu Gly Leu
1               5                   10                  15

Xaa Xaa Xaa Xaa Xaa Xaa Xaa Tyr Glu Asp Ile
            20                  25

<210> SEQ ID NO 22
<211> LENGTH: 26
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: D/E
<222> LOCATION: (9)..(9)
<223> OTHER INFORMATION: "Xaa" can be aspartate or glutamate
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (16)..(22)
<223> OTHER INFORMATION: Xaa can be any naturally occurring amino acid

<400> SEQUENCE: 22

Xaa Xaa Xaa Xaa Xaa Xaa Xaa Xaa Xaa Xaa Xaa Tyr Glu Gly Leu Xaa
1               5                   10                  15

Xaa Xaa Xaa Xaa Xaa Xaa Tyr Glu Asp Ile
            20                  25
```

```
<210> SEQ ID NO 23
<211> LENGTH: 31
<212> TYPE: PRT
<213> ORGANISM: Mus musculus

<400> SEQUENCE: 23

Glu Lys Phe Gly Val Asp Met Pro Asp Asp Tyr Glu Asp Glu Asn Leu
1               5                   10                  15

Tyr Glu Gly Leu Asn Leu Asp Asp Cys Ser Met Tyr Glu Asp Ile
            20                  25                  30

<210> SEQ ID NO 24
<211> LENGTH: 36
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: Variablelength
<222> LOCATION: (11)..(12)
<223> OTHER INFORMATION: 0-2 residues may not be present
<220> FEATURE:
<221> NAME/KEY: X
<222> LOCATION: (11)..(12)
<223> OTHER INFORMATION: Xaa may be any naturally occurring amino acid
<220> FEATURE:
<221> NAME/KEY: Variablelength
<222> LOCATION: (17)..(24)
<223> OTHER INFORMATION: 0-9 residues may not be present
<220> FEATURE:
<221> NAME/KEY: X
<222> LOCATION: (17)..(24)
<223> OTHER INFORMATION: Xaa may be any naturally occurring amino acid
<220> FEATURE:
<221> NAME/KEY: misc_feature
<222> LOCATION: (25)..(32)
<223> OTHER INFORMATION: Xaa can be any naturally occurring amino acid

<400> SEQUENCE: 24

Xaa Xaa Xaa Xaa Xaa Xaa Xaa Xaa Xaa Xaa Xaa Xaa Tyr Glu Asp Glu
1               5                   10                  15

Xaa Xaa Xaa Xaa Xaa Xaa Xaa Xaa Xaa Xaa Xaa Xaa Xaa Xaa Xaa Xaa
            20                  25                  30

Tyr Glu Asp Ile
        35

<210> SEQ ID NO 25
<211> LENGTH: 34
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
```

```
<223> OTHER INFORMATION: "Xaa" can be aspartate or glutamate
<220> FEATURE:
<221> NAME/KEY: Variablelength
<222> LOCATION: (2)..(11)
<223> OTHER INFORMATION: 0-1 residues may not be present
<220> FEATURE:
<221> NAME/KEY: X
<222> LOCATION: (2)..(11)
<223> OTHER INFORMATION: Xaa may be any naturally occurring amino acid
<220> FEATURE:
<221> NAME/KEY: D/E
<222> LOCATION: (12)..(12)
<223> OTHER INFORMATION: "Xaa" can be aspartate or glutamate
<220> FEATURE:
<221> NAME/KEY: Variablelength
<222> LOCATION: (13)..(13)
<223> OTHER INFORMATION: residue may not be present
<220> FEATURE:
<221> NAME/KEY: X
<222> LOCATION: (13)..(13)
<223> OTHER INFORMATION: Xaa may be any naturally occurring amino acid
<220> FEATURE:
<221> NAME/KEY: misc_feature
<222> LOCATION: (18)..(30)
<223> OTHER INFORMATION: Xaa can be any naturally occurring amino acid

<400> SEQUENCE: 25

Xaa Xaa Xaa Xaa Xaa Xaa Xaa Xaa Xaa Xaa Xaa Xaa Xaa Tyr Glu Asp
1               5                   10                  15

Glu Xaa Xaa Xaa Xaa Xaa Xaa Xaa Xaa Xaa Xaa Xaa Xaa Xaa Tyr Glu
            20                  25                  30

Asp Ile

<210> SEQ ID NO 26
<211> LENGTH: 33
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: Variablelength
<222> LOCATION: (11)..(12)
<223> OTHER INFORMATION: 0-2 residues may not be present
<220> FEATURE:
<221> NAME/KEY: X
<222> LOCATION: (11)..(12)
<223> OTHER INFORMATION: Xaa may be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (23)..(29)
<223> OTHER INFORMATION: Xaa can be any naturally occurring amino acid

<400> SEQUENCE: 26

Xaa Xaa Xaa Xaa Xaa Xaa Xaa Xaa Xaa Xaa Xaa Xaa Tyr Glu Asp Glu
```

```
                1               5                   10                  15
Xaa Xaa Tyr Glu Gly Leu Xaa Xaa Xaa Xaa Xaa Xaa Xaa Tyr Glu Asp
            20                  25                  30

Ile
```

<210> SEQ ID NO 27
<211> LENGTH: 34
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(11)
<223> OTHER INFORMATION: 0-1 residues may not be present
<220> FEATURE:
<221> NAME/KEY: X
<222> LOCATION: (2)..(11)
<223> OTHER INFORMATION: Xaa may be any naturally occurring amino acid
<220> FEATURE:
<221> NAME/KEY: D/E
<222> LOCATION: (12)..(12)
<223> OTHER INFORMATION: "Xaa" can be aspartate or glutamate
<220> FEATURE:
<221> NAME/KEY: Variablelength
<222> LOCATION: (13)..(13)
<223> OTHER INFORMATION: residue may not be present
<220> FEATURE:
<221> NAME/KEY: X
<222> LOCATION: (13)..(13)
<223> OTHER INFORMATION: Xaa may be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (24)..(30)
<223> OTHER INFORMATION: Xaa can be any naturally occurring amino acid

<400> SEQUENCE: 27

```
Xaa Xaa Xaa Xaa Xaa Xaa Xaa Xaa Xaa Xaa Xaa Xaa Xaa Tyr Glu Asp
1               5                   10                  15

Glu Xaa Xaa Tyr Glu Gly Leu Xaa Xaa Xaa Xaa Xaa Xaa Xaa Tyr Glu
            20                  25                  30

Asp Ile
```

<210> SEQ ID NO 28
<211> LENGTH: 29
<212> TYPE: PRT
<213> ORGANISM: Mus musculus

<400> SEQUENCE: 28

```
Asp Lys Asp Asp Gly Lys Ala Gly Met Glu Glu Asp His Thr Tyr Glu
1               5                   10                  15

Gly Leu Asn Ile Asp Gln Thr Ala Thr Tyr Glu Asp Ile
            20                  25
```

<210> SEQ ID NO 29
<211> LENGTH: 28
<212> TYPE: PRT
<213> ORGANISM: Artificial
<220> FEATURE:
<223> OTHER INFORMATION: synthetic construct
<220> FEATURE:

-continued

```
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: Variablelength
<222> LOCATION: (11)..(12)
<223> OTHER INFORMATION: 0-2 residues may not be present
<220> FEATURE:
<221> NAME/KEY: X
<222> LOCATION: (11)..(12)
<223> OTHER INFORMATION: Xaa may be any naturally occurring amino acid
<220> FEATURE:
<221> NAME/KEY: Variablelength
<222> LOCATION: (17)..(24)
<223> OTHER INFORMATION: 0-2 residues may not be present
<220> FEATURE:
<221> NAME/KEY: X
<222> LOCATION: (17)..(24)
<223> OTHER INFORMATION: Xaa may be any naturally occurring amino acid

<400> SEQUENCE: 29

Xaa Xaa Xaa Xaa Xaa Xaa Xaa Xaa Xaa Xaa Xaa Xaa Tyr Glu Gly Leu
1               5                   10                  15

Xaa Xaa Xaa Xaa Xaa Xaa Xaa Xaa Tyr Glu Asp Ile
            20                  25

<210> SEQ ID NO 30
<211> LENGTH: 28
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: Variablelength
<222> LOCATION: (17)..(24)
<223> OTHER INFORMATION: 0-2 residues may not be present
<220> FEATURE:
<221> NAME/KEY: X
<222> LOCATION: (17)..(24)
<223> OTHER INFORMATION: Xaa may be any naturally occurring amino acid

<400> SEQUENCE: 30

Xaa Xaa Xaa Xaa Xaa Xaa Xaa Xaa Xaa Xaa Xaa Xaa Tyr Glu Gly Leu
```

```
                1               5                   10                  15
Xaa Xaa Xaa Xaa Xaa Xaa Xaa Xaa Tyr Glu Asp Ile
            20                  25

<210> SEQ ID NO 31
<211> LENGTH: 27
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: Variablelength
<222> LOCATION: (11)..(12)
<223> OTHER INFORMATION: 0-2 residues may not be present
<220> FEATURE:
<221> NAME/KEY: X
<222> LOCATION: (11)..(12)
<223> OTHER INFORMATION: Xaa may be any naturally occurring amino acid
<220> FEATURE:
<221> NAME/KEY: misc_feature
<222> LOCATION: (17)..(23)
<223> OTHER INFORMATION: Xaa can be any naturally occurring amino acid

<400> SEQUENCE: 31

Xaa Xaa Xaa Xaa Xaa Xaa Xaa Xaa Xaa Xaa Xaa Xaa Tyr Glu Gly Leu
1               5                   10                  15

Xaa Xaa Xaa Xaa Xaa Xaa Xaa Tyr Glu Asp Ile
            20                  25

<210> SEQ ID NO 32
<211> LENGTH: 27
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: Variablelength
<222> LOCATION: (2)..(9)
<223> OTHER INFORMATION: 0-1 residues may not be present
<220> FEATURE:
<221> NAME/KEY: X
<222> LOCATION: (2)..(9)
<223> OTHER INFORMATION: Xaa may be any naturally occurring amino acid
<220> FEATURE:
<221> NAME/KEY: D/E
<222> LOCATION: (10)..(10)
<223> OTHER INFORMATION: "Xaa" can be aspartate or glutamate
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (17)..(23)
```

<223> OTHER INFORMATION: Xaa can be any naturally occurring amino acid

<400> SEQUENCE: 32

```
Xaa Xaa Xaa Xaa Xaa Xaa Xaa Xaa Xaa Xaa Xaa Xaa Tyr Glu Gly Leu
1               5                   10                  15

Xaa Xaa Xaa Xaa Xaa Xaa Xaa Tyr Glu Asp Ile
            20                  25
```

<210> SEQ ID NO 33
<211> LENGTH: 14
<212> TYPE: PRT
<213> ORGANISM: Mouse mammary tumor virus

<400> SEQUENCE: 33

```
Lys Arg Pro Pro Tyr Val Leu Leu Pro Val Asp Ile Gly Asp
1               5                   10
```

<210> SEQ ID NO 34
<211> LENGTH: 8
<212> TYPE: PRT
<213> ORGANISM: Mus musculus

<400> SEQUENCE: 34

```
Asp Cys Ser Met Tyr Glu Asp Ile
1               5
```

<210> SEQ ID NO 35
<211> LENGTH: 8
<212> TYPE: PRT
<213> ORGANISM: Mus musculus

<400> SEQUENCE: 35

```
Gln Thr Ala Thr Tyr Glu Asp Ile
1               5
```

<210> SEQ ID NO 36
<211> LENGTH: 29
<212> TYPE: PRT
<213> ORGANISM: Homo sapiens

<400> SEQUENCE: 36

```
Ser Ser Cys Arg Leu Thr Asn Cys Leu Asp Ser Ser Ala Tyr Val Tyr
1               5                   10                  15

Ala Ala Ile Ile Val Leu Met Pro Pro Tyr Val Leu Leu
            20                  25
```

<210> SEQ ID NO 37
<211> LENGTH: 20
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: X
<222> LOCATION: (2)..(6)
<223> OTHER INFORMATION: Xaa may be any naturally occurring amino acid
<220> FEATURE:
<221> NAME/KEY: X
<222> LOCATION: (11)..(16)
<223> OTHER INFORMATION: Xaa may be any naturally occurring amino acid

<400> SEQUENCE: 37

```
Xaa Xaa Xaa Xaa Xaa Xaa Tyr Ala Ala Ile Xaa Xaa Xaa Xaa Xaa Xaa
1               5                   10                  15

Tyr Val Leu Leu
            20
```

<210> SEQ ID NO 38
<211> LENGTH: 26
<212> TYPE: PRT
<213> ORGANISM: Homo sapiens

<400> SEQUENCE: 38

```
Arg Leu Thr Asn Cys Leu Asp Ser Ser Ala Tyr Asp Tyr Ala Ala Ile
1               5                   10                  15

Ile Val Lys Arg Pro Pro Tyr Val Leu Leu
            20                  25
```

<210> SEQ ID NO 39
<211> LENGTH: 20
<212> TYPE: PRT
<213> ORGANISM: Artificial
<220> FEATURE:
<223> OTHER INFORMATION: synthetic construct
<220> FEATURE:
<221> NAME/KEY: D/E
<222> LOCATION: (1)..(1)
<223> OTHER INFORMATION: "Xaa" can be aspartate or glutamate
<220> FEATURE:
<221> NAME/KEY: X
<222> LOCATION: (2)..(5)
<223> OTHER INFORMATION: Xaa may be any naturally occurring amino acid
<220> FEATURE:
<221> NAME/KEY: X
<222> LOCATION: (11)..(16)
<223> OTHER INFORMATION: Xaa may be any naturally occurring amino acid

<400> SEQUENCE: 39

```
Xaa Xaa Xaa Xaa Xaa Asp Tyr Ala Ala Ile Xaa Xaa Xaa Xaa Xaa Xaa
1               5                   10                  15

Tyr Val Leu Leu
            20
```

<210> SEQ ID NO 40
<211> LENGTH: 20
<212> TYPE: PRT
<213> ORGANISM: Homo sapiens

<400> SEQUENCE: 40

```
Asp Ser Ser Ala Tyr Asp Tyr Ala Ala Ile Ile Val Lys Arg Pro Pro
1               5                   10                  15

Tyr Val Leu Leu
            20
```

<210> SEQ ID NO 41
<211> LENGTH: 20
<212> TYPE: PRT
<213> ORGANISM: Artificial
<220> FEATURE:
<223> OTHER INFORMATION: synthetic construct
<220> FEATURE:
<221> NAME/KEY: X
<222> LOCATION: (2)..(5)
<223> OTHER INFORMATION: Xaa may be any naturally occurring amino acid
<220> FEATURE:
<221> NAME/KEY: X
<222> LOCATION: (11)..(16)
<223> OTHER INFORMATION: Xaa may be any naturally occurring amino acid

<400> SEQUENCE: 41

```
Asp Xaa Xaa Xaa Xaa Asp Tyr Ala Ala Ile Xaa Xaa Xaa Xaa Xaa Xaa
1               5                   10                  15

Tyr Val Leu Leu
            20
```

<210> SEQ ID NO 42
<211> LENGTH: 41
<212> TYPE: DNA
<213> ORGANISM: Artificial
<220> FEATURE:
<223> OTHER INFORMATION: primer

<400> SEQUENCE: 42
ccacctgttc ctgtatgtgc tgctatgaag atctcgagct c                41

<210> SEQ ID NO 43
<211> LENGTH: 41
<212> TYPE: DNA
<213> ORGANISM: Artificial
<220> FEATURE:
<223> OTHER INFORMATION: primer

<400> SEQUENCE: 43
ggtggacaag gacatacacg acgatacttc tagagctcga g                41

<210> SEQ ID NO 44
<211> LENGTH: 44
<212> TYPE: DNA
<213> ORGANISM: Artificial
<220> FEATURE:
<223> OTHER INFORMATION: primer

<400> SEQUENCE: 44
cctgttcctg aagaggccat atgtgctgct atagagatct cgag             44

<210> SEQ ID NO 45
<211> LENGTH: 47
<212> TYPE: DNA
<213> ORGANISM: Artificial
<220> FEATURE:
<223> OTHER INFORMATION: primer

<400> SEQUENCE: 45
cgacaaggac ttctccggcg gtatacacga cgatatctct agagctc          47

<210> SEQ ID NO 46
<211> LENGTH: 8
<212> TYPE: PRT
<213> ORGANISM: Artificial
<220> FEATURE:
<223> OTHER INFORMATION: synthetic construct
<220> FEATURE:
<221> NAME/KEY: biotin
<222> LOCATION: (1)..(1)

<400> SEQUENCE: 46

```
Lys Arg Pro Pro Ala Val Leu Leu
1               5
```

<210> SEQ ID NO 47
<211> LENGTH: 8
<212> TYPE: PRT
<213> ORGANISM: Mouse mammary tumor virus
<220> FEATURE:
<221> NAME/KEY: biotin
<222> LOCATION: (1)..(1)

```
<400> SEQUENCE: 47

Lys Arg Pro Pro Tyr Val Leu Leu
1               5

<210> SEQ ID NO 48
<211> LENGTH: 8
<212> TYPE: PRT
<213> ORGANISM: Mouse mammary tumor virus

<400> SEQUENCE: 48

Lys Arg Pro Pro Tyr Val Leu Leu
1               5

<210> SEQ ID NO 49
<211> LENGTH: 4
<212> TYPE: PRT
<213> ORGANISM: Mouse mammary tumor virus
<220> FEATURE:
<221> NAME/KEY: dsRed
<222> LOCATION: (1)..(1)

<400> SEQUENCE: 49

Tyr Val Leu Leu
1

<210> SEQ ID NO 50
<211> LENGTH: 22
<212> TYPE: PRT
<213> ORGANISM: Epstein-Barr virus

<400> SEQUENCE: 50

Arg His Ser Asp Tyr Gln Pro Leu Gly Thr Gln Asp Gln Ser Leu Tyr
1               5                   10                  15

Leu Gly Leu Gln His Gly
            20

<210> SEQ ID NO 51
<211> LENGTH: 27
<212> TYPE: PRT
<213> ORGANISM: Kaposi's sarcoma-associated herpesvirus

<400> SEQUENCE: 51

Asp Ser Asn Lys Thr Val Pro Gln Gln Leu Gln Asp Tyr Tyr Ser Leu
1               5                   10                  15

His Asp Leu Cys Thr Glu Asp Tyr Thr Gln Pro
            20                  25

<210> SEQ ID NO 52
<211> LENGTH: 24
<212> TYPE: PRT
<213> ORGANISM: Hantavirus sp.

<400> SEQUENCE: 52

Lys Gln Gly Cys Tyr Arg Thr Leu Gly Val Phe Arg Tyr Lys Ser Arg
1               5                   10                  15

Cys Tyr Val Gly Leu Val Trp Gly
            20

<210> SEQ ID NO 53
<211> LENGTH: 24
<212> TYPE: PRT
<213> ORGANISM: Hantavirus sp.
```

```
<400> SEQUENCE: 53

Arg Lys Gly Cys Tyr Arg Thr Leu Gly Val Phe Arg Tyr Lys Ser Arg
1               5                   10                  15
Cys Tyr Val Gly Leu Val Trp Gly
            20

<210> SEQ ID NO 54
<211> LENGTH: 24
<212> TYPE: PRT
<213> ORGANISM: Hantavirus sp.

<400> SEQUENCE: 54

Lys Arg Gly Cys Tyr Arg Thr Leu Gly Val Phe Arg Tyr Lys Ser Arg
1               5                   10                  15
Cys Tyr Val Gly Leu Val Trp Ser
            20

<210> SEQ ID NO 55
<211> LENGTH: 24
<212> TYPE: PRT
<213> ORGANISM: Hantavirus sp.

<400> SEQUENCE: 55

Gln Arg Gly Cys Tyr Arg Thr Leu Gly Val Phe Arg Tyr Lys Ser Arg
1               5                   10                  15
Cys Tyr Val Gly Leu Val Trp Asn
            20

<210> SEQ ID NO 56
<211> LENGTH: 24
<212> TYPE: PRT
<213> ORGANISM: Hantavirus sp.

<400> SEQUENCE: 56

Lys Pro Gly Cys Tyr Arg Thr Leu Gly Val Phe Arg Tyr Lys Ser Arg
1               5                   10                  15
Cys Tyr Val Gly Leu Val Trp Gly
            20

<210> SEQ ID NO 57
<211> LENGTH: 24
<212> TYPE: PRT
<213> ORGANISM: Hantavirus sp.

<400> SEQUENCE: 57

Lys Lys Gly Cys Tyr Arg Thr Leu Gly Val Phe Arg Tyr Lys Ser Arg
1               5                   10                  15
Cys Tyr Val Gly Leu Val Trp Cys
            20

<210> SEQ ID NO 58
<211> LENGTH: 24
<212> TYPE: PRT
<213> ORGANISM: Hantavirus sp.

<400> SEQUENCE: 58

Lys Arg Gly Cys Tyr Arg Thr Leu Gly Val Phe Arg Tyr Lys Ser Arg
1               5                   10                  15
Cys Tyr Val Gly Leu Val Trp Cys
            20
```

-continued

```
<210> SEQ ID NO 59
<211> LENGTH: 24
<212> TYPE: PRT
<213> ORGANISM: Hantavirus sp.

<400> SEQUENCE: 59

His Arg Gly Cys Tyr Arg Thr Leu Gly Val Phe Arg Tyr Arg Ser Arg
1               5                   10                  15

Cys Tyr Val Gly Leu Val Trp Gly
            20

<210> SEQ ID NO 60
<211> LENGTH: 24
<212> TYPE: PRT
<213> ORGANISM: Hantavirus sp.

<400> SEQUENCE: 60

Arg Lys Gly Cys Tyr Arg Thr Leu Gly Val Phe Arg Tyr Lys Ser Arg
1               5                   10                  15

Cys Tyr Val Gly Leu Val Trp Cys
            20

<210> SEQ ID NO 61
<211> LENGTH: 24
<212> TYPE: PRT
<213> ORGANISM: Hantavirus sp.

<400> SEQUENCE: 61

Gly Lys Gly Cys Tyr Arg Thr Leu Gly Val Phe Arg Tyr Lys Ser Arg
1               5                   10                  15

Cys Tyr Val Gly Leu Val Trp Cys
            20

<210> SEQ ID NO 62
<211> LENGTH: 24
<212> TYPE: PRT
<213> ORGANISM: Hantavirus sp.

<400> SEQUENCE: 62

Lys Arg Gly Cys Tyr Arg Thr Leu Ser Val Phe Arg Tyr Arg Ser Arg
1               5                   10                  15

Cys Phe Val Gly Leu Val Trp Cys
            20

<210> SEQ ID NO 63
<211> LENGTH: 24
<212> TYPE: PRT
<213> ORGANISM: Hantavirus sp.

<400> SEQUENCE: 63

Met Gln Gly Cys Tyr Arg Thr Leu Ser Leu Phe Arg Tyr Arg Ser Arg
1               5                   10                  15

Phe Phe Val Gly Leu Val Trp Cys
            20

<210> SEQ ID NO 64
<211> LENGTH: 24
<212> TYPE: PRT
<213> ORGANISM: Hantavirus sp.

<400> SEQUENCE: 64

Lys Arg Gly Leu Tyr Arg Thr Leu Ser Met Phe Arg Tyr Lys Ser Lys
1               5                   10                  15
```

Cys Tyr Val Gly Leu Val Trp Cys
            20

<210> SEQ ID NO 65
<211> LENGTH: 24
<212> TYPE: PRT
<213> ORGANISM: Hantavirus sp.

<400> SEQUENCE: 65

Thr Pro Gly Cys Tyr Arg Thr Leu Asn Leu Phe Arg Tyr Lys Ser Arg
1               5                   10                  15

Cys Tyr Ile Phe Thr Met Trp Ile
            20

<210> SEQ ID NO 66
<211> LENGTH: 24
<212> TYPE: PRT
<213> ORGANISM: Hantavirus sp.

<400> SEQUENCE: 66

Gly Pro Gly Cys Tyr Arg Thr Leu Asn Leu Phe Arg Tyr Lys Ser Arg
1               5                   10                  15

Cys Tyr Ile Leu Thr Met Trp Thr
            20

<210> SEQ ID NO 67
<211> LENGTH: 24
<212> TYPE: PRT
<213> ORGANISM: Hantavirus sp.

<400> SEQUENCE: 67

Ser Pro Gly Cys Tyr Arg Thr Leu Asn Leu Phe Arg Tyr Lys Ser Arg
1               5                   10                  15

Cys Tyr Ile Phe Thr Val Trp Val
            20

<210> SEQ ID NO 68
<211> LENGTH: 24
<212> TYPE: PRT
<213> ORGANISM: Hantavirus sp.

<400> SEQUENCE: 68

Gly Pro Gly Cys Tyr Arg Thr Leu Asn Leu Phe Arg Tyr Lys Ser Arg
1               5                   10                  15

Cys Tyr Ile Leu Thr Met Trp Leu
            20

<210> SEQ ID NO 69
<211> LENGTH: 29
<212> TYPE: PRT
<213> ORGANISM: Homo sapiens

<400> SEQUENCE: 69

Ala Ala Thr Ala Ser Glu Lys Ser Asp Gly Ile Tyr Thr Gly Leu Ser
1               5                   10                  15

Thr Arg Thr Gln Glu Thr Tyr Glu Thr Leu Lys His Glu
            20                  25

<210> SEQ ID NO 70
<211> LENGTH: 26
<212> TYPE: PRT
<213> ORGANISM: Homo sapiens

```
<400> SEQUENCE: 70

Glu Thr Ala Asp Gly Gly Tyr Met Thr Leu Asn Pro Arg Ala Pro Thr
1               5                   10                  15

Asp Asp Asp Lys Asn Ile Tyr Leu Thr Leu
            20                  25

<210> SEQ ID NO 71
<211> LENGTH: 28
<212> TYPE: PRT
<213> ORGANISM: Homo sapiens

<400> SEQUENCE: 71

Asp Tyr Glu Thr Ala Asp Gly Gly Tyr Met Thr Leu Asn Pro Arg Ala
1               5                   10                  15

Pro Thr Asp Asp Asp Lys Asn Ile Tyr Leu Thr Leu
            20                  25

<210> SEQ ID NO 72
<211> LENGTH: 26
<212> TYPE: PRT
<213> ORGANISM: Homo sapiens

<400> SEQUENCE: 72

Asp Ala Gly Asp Glu Tyr Glu Asp Glu Asn Leu Tyr Glu Gly Leu Asn
1               5                   10                  15

Leu Asp Asp Cys Ser Met Tyr Glu Asp Ile
            20                  25

<210> SEQ ID NO 73
<211> LENGTH: 29
<212> TYPE: PRT
<213> ORGANISM: Homo sapiens

<400> SEQUENCE: 73

Asp Ser Lys Ala Gly Met Glu Glu Asp His Thr Tyr Glu Gly Leu Asp
1               5                   10                  15

Ile Asp Gln Thr Ala Thr Tyr Glu Asp Ile Val Thr Leu
            20                  25

<210> SEQ ID NO 74
<211> LENGTH: 27
<212> TYPE: PRT
<213> ORGANISM: Homo sapiens

<400> SEQUENCE: 74

Asp Ala Pro Ala Tyr Gln Gln Gly Gln Asn Gln Leu Tyr Asn Glu Leu
1               5                   10                  15

Asn Leu Gly Arg Arg Glu Glu Tyr Asp Val Leu
            20                  25

<210> SEQ ID NO 75
<211> LENGTH: 27
<212> TYPE: PRT
<213> ORGANISM: Homo sapiens

<400> SEQUENCE: 75

Asp Ala Pro Ala Tyr Gln His Gly Gln Asn Pro Val Tyr Asn Glu Leu
1               5                   10                  15

Asn Val Gly Arg Arg Glu Glu Tyr Ala Val Leu
            20                  25
```

```
<210> SEQ ID NO 76
<211> LENGTH: 31
<212> TYPE: PRT
<213> ORGANISM: Homo sapiens

<400> SEQUENCE: 76

Asp Ala Pro Ala Tyr Gln Gln Gly Gln Asn Gln Leu Tyr Asn Glu Leu
1               5                   10                  15

Asn Leu Gly Arg Arg Glu Glu Tyr Asp Val Leu Asp Lys Arg Arg
            20                  25                  30

<210> SEQ ID NO 77
<211> LENGTH: 27
<212> TYPE: PRT
<213> ORGANISM: Homo sapiens

<400> SEQUENCE: 77

Glu Thr Ala Ala Asn Leu Gln Asp Pro Asn Gln Leu Tyr Asn Glu Leu
1               5                   10                  15

Asn Leu Gly Arg Arg Glu Glu Tyr Asp Val Leu
            20                  25

<210> SEQ ID NO 78
<211> LENGTH: 31
<212> TYPE: PRT
<213> ORGANISM: Homo sapiens

<400> SEQUENCE: 78

Asp Val Pro Val Ser Pro Gln Gly His Thr Gln Leu Tyr Asn Glu Leu
1               5                   10                  15

Asn Ile Gly Arg Arg Glu Glu Tyr Asp Val Leu Asp Lys Arg Arg
            20                  25                  30

<210> SEQ ID NO 79
<211> LENGTH: 29
<212> TYPE: PRT
<213> ORGANISM: Homo sapiens

<400> SEQUENCE: 79

Thr Ala Ala Asn Leu Gln Asp Pro Asn Gln Leu Tyr Asn Glu Leu Asn
1               5                   10                  15

Leu Gly Arg Arg Glu Glu Tyr Asp Val Leu Glu Lys Lys
            20                  25

<210> SEQ ID NO 80
<211> LENGTH: 29
<212> TYPE: PRT
<213> ORGANISM: Homo sapiens

<400> SEQUENCE: 80

Gln Gln Arg Arg Arg Asn Pro Gln Glu Gly Val Tyr Asn Ala Leu Gln
1               5                   10                  15

Lys Asp Lys Met Ala Glu Ala Tyr Ser Glu Ile Gly Thr
            20                  25

<210> SEQ ID NO 81
<211> LENGTH: 28
<212> TYPE: PRT
<213> ORGANISM: Homo sapiens

<400> SEQUENCE: 81

Glu Arg Pro Pro Pro Val Pro Asn Pro Asp Tyr Glu Pro Ile Arg Lys
```

-continued

```
                1               5                  10                  15
Gly Gln Arg Asp Leu Tyr Ser Gly Leu Asn Gln Arg
                20                  25

<210> SEQ ID NO 82
<211> LENGTH: 29
<212> TYPE: PRT
<213> ORGANISM: Homo sapiens

<400> SEQUENCE: 82

Asp Thr Gln Ala Leu Leu Arg Asn Asp Gln Val Tyr Gln Pro Leu Arg
1               5                   10                  15

Asp Arg Asp Asp Ala Gln Tyr Ser His Leu Gly Gly Asn
                20                  25

<210> SEQ ID NO 83
<211> LENGTH: 29
<212> TYPE: PRT
<213> ORGANISM: Homo sapiens

<400> SEQUENCE: 83

Asp Lys Gln Thr Leu Leu Pro Asn Asp Gln Leu Tyr Gln Pro Leu Lys
1               5                   10                  15

Asp Arg Glu Asp Asp Gln Tyr Ser His Leu Gln Gly Asn
                20                  25

<210> SEQ ID NO 84
<211> LENGTH: 29
<212> TYPE: PRT
<213> ORGANISM: Homo sapiens

<400> SEQUENCE: 84

Asp Lys Gln Thr Leu Leu Asn Asn Asp Gln Leu Tyr Gln Pro Leu Lys
1               5                   10                  15

Glu Arg Glu Asp Asp Gln Tyr Ser His Leu Arg Lys Lys
                20                  25

<210> SEQ ID NO 85
<211> LENGTH: 29
<212> TYPE: PRT
<213> ORGANISM: Homo sapiens

<400> SEQUENCE: 85

Glu Val Gln Ala Leu Leu Lys Asn Glu Gln Leu Tyr Gln Pro Leu Arg
1               5                   10                  15

Asp Arg Glu Asp Thr Gln Tyr Ser Arg Leu Gly Gly Asn
                20                  25

<210> SEQ ID NO 86
<211> LENGTH: 29
<212> TYPE: PRT
<213> ORGANISM: Homo sapiens

<400> SEQUENCE: 86

Ala Ile Ala Ser Arg Glu Lys Ala Asp Ala Val Tyr Thr Gly Leu Asn
1               5                   10                  15

Thr Arg Ser Gln Glu Thr Tyr Glu Thr Leu Lys His Glu
                20                  25

<210> SEQ ID NO 87
<211> LENGTH: 30
<212> TYPE: PRT
```

<213> ORGANISM: Homo sapiens

<400> SEQUENCE: 87

Ala Ala Ile Thr Ser Tyr Glu Lys Ser Asp Gly Val Tyr Thr Gly Leu
1               5                   10                  15

Ser Thr Arg Asn Gln Glu Thr Tyr Glu Thr Leu Lys His Glu
            20                  25                  30

<210> SEQ ID NO 88
<211> LENGTH: 29
<212> TYPE: PRT
<213> ORGANISM: Homo sapiens

<400> SEQUENCE: 88

Asp Ile Ala Ser Arg Glu Lys Ser Asp Ala Val Tyr Thr Gly Leu Asn
1               5                   10                  15

Thr Arg Asn Gln Glu Thr Tyr Glu Thr Leu Lys His Glu
            20                  25

<210> SEQ ID NO 89
<211> LENGTH: 8
<212> TYPE: PRT
<213> ORGANISM: Artificial
<220> FEATURE:
<223> OTHER INFORMATION: synthetic construct

<400> SEQUENCE: 89

Lys Arg Pro Pro Tyr Leu Val Val
1               5

<210> SEQ ID NO 90
<211> LENGTH: 28
<212> TYPE: PRT
<213> ORGANISM: Cercopithecine herpesvirus 15

<400> SEQUENCE: 90

Pro Tyr Asp Ala Glu Asp Gly Gly Asp Gly Pro Tyr Gln Pro Leu
1               5                   10                  15

Arg Gly Gln Asp Pro Asn Gln Leu Tyr Ala Arg Leu
            20                  25

<210> SEQ ID NO 91
<211> LENGTH: 46
<212> TYPE: PRT
<213> ORGANISM: Cercopithecine herpesvirus 15

<400> SEQUENCE: 91

Gly Pro Tyr Gln Pro Leu Arg Gly Gln Asp Pro Asn Gln Leu Tyr Ala
1               5                   10                  15

Arg Leu Gly Gly Gly Gly Asn Gly Thr Leu Pro Pro Pro Tyr
            20                  25                  30

Ser Pro Gln Arg Glu Thr Ser Leu His Leu Tyr Glu Glu Ile
        35                  40                  45

<210> SEQ ID NO 92
<211> LENGTH: 28
<212> TYPE: PRT
<213> ORGANISM: Cercopithecine herpesvirus 15

<400> SEQUENCE: 92

Glu Asp Pro Tyr Trp Gly Asn Gly Asp Arg His Ser Asp Tyr Gln Pro
1               5                   10                  15

Leu Gly Thr Gln Asp Gln Ser Leu Tyr Leu Gly Leu
            20                  25

<210> SEQ ID NO 93
<211> LENGTH: 31
<212> TYPE: PRT
<213> ORGANISM: Human herpesvirus 4

<400> SEQUENCE: 93

Pro Pro Tyr Glu Asp Leu Asp Trp Gly Asn Gly Asp Arg His Ser Asp
1               5                   10                  15

Tyr Gln Pro Leu Gly Asn Gln Asp Pro Ser Leu Tyr Leu Gly Leu
            20                  25                  30

<210> SEQ ID NO 94
<211> LENGTH: 31
<212> TYPE: PRT
<213> ORGANISM: Human herpesvirus 4

<400> SEQUENCE: 94

Tyr Asp Ala Pro Ser His Arg Pro Pro Ser Tyr Gly Gly Ser Gly Gly
1               5                   10                  15

Tyr Ala Thr Leu Gly Gln Gln Glu Pro Ser Leu Tyr Ala Gly Leu
            20                  25                  30

<210> SEQ ID NO 95
<211> LENGTH: 41
<212> TYPE: PRT
<213> ORGANISM: Human herpesvirus 4

<400> SEQUENCE: 95

Asp Arg Asp Gly Asp Pro Val Pro Pro Asp Tyr Asp Ala Pro Ser His
1               5                   10                  15

Arg Pro Pro Ser Tyr Gly Gly Ser Gly Gly Tyr Ala Thr Leu Gly Gln
            20                  25                  30

Gln Glu Pro Ser Leu Tyr Ala Gly Leu
        35                  40

<210> SEQ ID NO 96
<211> LENGTH: 48
<212> TYPE: PRT
<213> ORGANISM: Cercopithecine herpesvirus 12

<400> SEQUENCE: 96

Leu Ser Lys Leu Thr Ala Leu Val Ala Val Ala Thr Trp Phe Ala Ile
1               5                   10                  15

Leu Met Thr Tyr Leu Val Leu Pro Ser Ala Asn Asn Ile Ile Val Leu
            20                  25                  30

Ser Leu Leu Val Ala Ala Glu Gly Ile Gln Ser Ile Tyr Leu Leu Val
        35                  40                  45

<210> SEQ ID NO 97
<211> LENGTH: 38
<212> TYPE: PRT
<213> ORGANISM: Human herpesvirus 4

<400> SEQUENCE: 97

Glu Ser Asn Glu Glu Pro Pro Pro Tyr Glu Asp Pro Tyr Trp Gly
1               5                   10                  15

Asn Gly Asp Arg His Ser Asp Tyr Gln Pro Leu Gly Thr Gln Asp Gln
            20                  25                  30

```
Ser Leu Tyr Leu Gly Leu
        35

<210> SEQ ID NO 98
<211> LENGTH: 28
<212> TYPE: PRT
<213> ORGANISM: Human herpesvirus 4

<400> SEQUENCE: 98

Glu Asp Ser Asp Trp Gly Asn Gly Asp Arg His Ser Asp Tyr Gln Pro
1               5                   10                  15

Leu Gly Asn Gln Asp Pro Ser Leu Tyr Leu Gly Leu
            20                  25

<210> SEQ ID NO 99
<211> LENGTH: 23
<212> TYPE: PRT
<213> ORGANISM: Mouse mammary tumor virus

<400> SEQUENCE: 99

Pro Ala Tyr Asp Tyr Ala Ala Ile Val Lys Arg Pro Pro Tyr Val Leu
1               5                   10                  15

Leu Pro Val Asp Ile Gly Asp
            20
```